(12) United States Patent
Lantz et al.

(10) Patent No.: US 11,655,289 B2
(45) Date of Patent: May 23, 2023

(54) PHARMACEUTICAL COMPOSITIONS CONTAINING ANTI-BETA AMYLOID ANTIBODIES

(71) Applicant: Biogen MA Inc., Cambridge, MA (US)

(72) Inventors: Steven Andrew Lantz, Jamaica Plain, MA (US); Kapil Gupta, Concord, MA (US); Shantanu Sule, Arlington, MA (US); Adnan Zunic, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 19 days.

(21) Appl. No.: 16/639,338

(22) PCT Filed: Aug. 22, 2018

(86) PCT No.: PCT/US2018/047508
§ 371 (c)(1),
(2) Date: Feb. 14, 2020

(87) PCT Pub. No.: WO2019/040612
PCT Pub. Date: Feb. 28, 2019

(65) Prior Publication Data
US 2021/0188954 A1 Jun. 24, 2021

Related U.S. Application Data

(60) Provisional application No. 62/548,583, filed on Aug. 22, 2017.

(51) Int. Cl.
*A61K 39/395* (2006.01)
*C07K 16/18* (2006.01)
*A61K 47/18* (2017.01)
*A61K 47/20* (2006.01)
*A61K 47/22* (2006.01)
*A61K 47/26* (2006.01)
*A61K 39/00* (2006.01)

(52) U.S. Cl.
CPC .......... *C07K 16/18* (2013.01); *A61K 39/3955* (2013.01); *A61K 39/39591* (2013.01); *A61K 47/183* (2013.01); *A61K 47/20* (2013.01); *A61K 47/22* (2013.01); *A61K 47/26* (2013.01); *A61K 2039/505* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,876,950 A | 3/1999 | Siadak et al. |
| 6,180,370 B1 | 1/2001 | Queen |
| 6,187,309 B1 | 2/2001 | McMichael et al. |
| 6,294,171 B2 | 9/2001 | McMichael |
| 6,436,401 B1 | 8/2002 | McMichael |
| 6,586,656 B2 | 7/2003 | McLonlogue et al. |
| 6,703,015 B1 | 3/2004 | Solomon et al. |
| 6,710,226 B1 | 3/2004 | Schenk |
| 6,713,058 B2 | 3/2004 | McMichael |
| 6,743,427 B1 | 6/2004 | Schenk |
| 6,750,324 B1 | 6/2004 | Schenk et al. |
| 6,761,888 B1 | 7/2004 | Schenk |
| 6,787,637 B1 | 9/2004 | Schenk |
| 6,875,432 B2 | 4/2005 | Liu et al. |
| 6,913,745 B1 | 7/2005 | Schenk |
| 7,582,733 B2 | 9/2009 | Basi et al. |
| 7,666,413 B2 | 2/2010 | Liu et al. |
| 7,700,751 B2 | 4/2010 | Basi et al. |
| 7,727,957 B2 | 6/2010 | Schenk et al. |
| 7,763,249 B2 | 7/2010 | Suginura et al. |
| 7,893,214 B2 | 2/2011 | Schenk |
| 7,964,192 B1 | 6/2011 | Schenk |
| 8,003,097 B2 | 8/2011 | Schroeter et al. |
| 8,022,268 B2 | 9/2011 | Grimm et al. |
| 8,034,339 B2 | 10/2011 | Schenk |
| 8,106,164 B2 | 1/2012 | Gellerfors et al. |
| 8,128,928 B2 | 3/2012 | Basi et al. |
| 8,142,776 B2 | 3/2012 | Liu et al. |
| 8,173,127 B2 | 5/2012 | Chain |
| 8,263,558 B2 | 9/2012 | Holzman et al. |
| 8,337,848 B2 | 12/2012 | Kidd et al. |
| 8,378,081 B2 | 2/2013 | Matsubara et al. |
| 8,389,226 B2 | 3/2013 | Ray et al. |
| 8,497,246 B2 | 7/2013 | Pardridge et al. |

(Continued)

FOREIGN PATENT DOCUMENTS

| CN | 102258464 A | 11/2011 |
|---|---|---|
| CN | 105979962 A | 9/2016 |

(Continued)

OTHER PUBLICATIONS

Blennow et al. "Fluid Biomarkers in Alzheimer Disease", Cold Spring Harbor Perspectives in Medicine, 2012, a006221, 24 pages.
ClinicalTrials.gov [online], "Multiple Dose Study of Aducanumab (BIIB037) (Recombinant, Fully Human Anti-AB IgG1 mAb) in Participants with Prodromal or Mild Alzheimer's Diseases (PRIME)", last updated on Nov. 12, 2019, [retrieved on Apr. 7, 2020], retrieved from URL<https://clinicaltrials.gov/ct2/show/NCT01677572>, 15 pages.

(Continued)

*Primary Examiner* — Yunsoo Kim

(74) *Attorney, Agent, or Firm* — Choate, Hall & Stewart LLP; Stephanie L. Schonewald; Tracy L. Vrablik

(57) ABSTRACT

Pharmaceutical compositions containing anti-beta amyloid (Aβ) antibodies or AD-binding fragments thereof are provided. These pharmaceutical compositions find use in the treatment of abnormal accumulation or deposition of Aβ in the central nervous system, mild cognitive impairment, and AD-associated disorders such as Alzheimer's disease.

18 Claims, 14 Drawing Sheets

Specification includes a Sequence Listing.

(56) References Cited

U.S. PATENT DOCUMENTS

| | | | |
|---|---|---|---|
| 8,703,126 B2 | 4/2014 | Liu et al. | |
| 8,753,610 B2 | 6/2014 | Pardridge et al. | |
| 8,906,367 B2 | 12/2014 | Nitsch et al. | |
| 9,670,272 B2 | 6/2017 | Nitsch et al. | |
| 9,828,420 B2 | 11/2017 | Nitsch et al. | |
| 9,910,049 B2 | 3/2018 | Jara et al. | |
| 10,131,708 B2 | 11/2018 | Nitsch et al. | |
| 10,166,293 B2 | 1/2019 | Liu et al. | |
| 10,202,445 B2 | 2/2019 | Nitsch et al. | |
| 10,537,638 B2 | 1/2020 | Crotts et al. | |
| 10,842,871 B2 | 11/2020 | Ferrero et al. | |
| 11,008,394 B2 | 5/2021 | Morichika et al. | |
| 2002/0002136 A1* | 1/2002 | Hebert | A61K 38/063 514/6.9 |
| 2002/0086847 A1 | 7/2002 | Chain | |
| 2003/0028904 A1 | 2/2003 | Gumienny et al. | |
| 2003/0232758 A1 | 12/2003 | St. George-Hyslop | |
| 2004/0197324 A1 | 10/2004 | Liu et al. | |
| 2004/0219146 A1 | 11/2004 | Schenk | |
| 2004/0265301 A1 | 12/2004 | Schenk et al. | |
| 2005/0009150 A1 | 1/2005 | Basi et al. | |
| 2005/0013815 A1 | 1/2005 | Schenk | |
| 2005/0048049 A1 | 3/2005 | Schenk | |
| 2005/0118651 A1 | 6/2005 | Basi et al. | |
| 2005/0249725 A1 | 11/2005 | Schenk et al. | |
| 2005/0249727 A1 | 11/2005 | Schenk | |
| 2005/0260697 A1 | 11/2005 | Wang et al. | |
| 2005/0276823 A1* | 12/2005 | Cini | A61K 47/183 424/400 |
| 2006/0062859 A1 | 3/2006 | Blum | |
| 2006/0165682 A1 | 7/2006 | Basi et al. | |
| 2006/0193850 A1 | 8/2006 | Warne et al. | |
| 2006/0210557 A1 | 9/2006 | Luisi et al. | |
| 2006/0235207 A1 | 10/2006 | Tsuchiya et al. | |
| 2006/0240485 A1 | 10/2006 | Hock | |
| 2006/0257396 A1 | 11/2006 | Jacobsen | |
| 2007/0031416 A1 | 2/2007 | Shoji et al. | |
| 2007/0190046 A1 | 8/2007 | DeMaattos et al. | |
| 2008/0050367 A1 | 2/2008 | Basi et al. | |
| 2008/0281082 A1 | 11/2008 | Basi et al. | |
| 2008/0292625 A1 | 11/2008 | Schroeter et al. | |
| 2008/0300204 A1 | 12/2008 | Federoff et al. | |
| 2009/0035295 A1 | 2/2009 | Hillen et al. | |
| 2009/0041771 A1 | 2/2009 | St. George-Hyslop | |
| 2009/0060906 A1 | 3/2009 | Barry et al. | |
| 2009/0069268 A1 | 3/2009 | Shepard et al. | |
| 2009/0069544 A1 | 3/2009 | Basi et al. | |
| 2009/0104629 A1 | 4/2009 | Fiala | |
| 2009/0191190 A1 | 7/2009 | Barghorn et al. | |
| 2009/0191231 A1 | 7/2009 | Schenk et al. | |
| 2009/0214515 A1 | 8/2009 | Holzman et al. | |
| 2009/0238831 A1 | 9/2009 | Hillen et al. | |
| 2009/0246145 A1 | 10/2009 | Small | |
| 2010/0120787 A1 | 5/2010 | Sutcliffe et al. | |
| 2010/0202968 A1 | 8/2010 | Nitsch et al. | |
| 2010/0209417 A1 | 8/2010 | Lee et al. | |
| 2010/0209422 A1 | 8/2010 | Ravetch et al. | |
| 2010/0221187 A1 | 9/2010 | Lieberburg et al. | |
| 2010/0239591 A1 | 9/2010 | Kidd et al. | |
| 2010/0266596 A1 | 10/2010 | Cox | |
| 2010/0279433 A1 | 11/2010 | Holtzman et al. | |
| 2010/0297108 A1 | 11/2010 | Henco et al. | |
| 2011/0044985 A1 | 2/2011 | Rosenthal et al. | |
| 2011/0044986 A1 | 2/2011 | Biere-Citron et al. | |
| 2011/0052498 A1 | 3/2011 | Lannfelt et al. | |
| 2011/0059092 A1 | 3/2011 | Vannechelen et al. | |
| 2011/0135660 A1 | 6/2011 | Schenk et al. | |
| 2011/0152341 A1 | 6/2011 | Schilling et al. | |
| 2011/0182809 A1 | 7/2011 | Nitsch et al. | |
| 2011/0200609 A1 | 8/2011 | Glabe et al. | |
| 2011/0212109 A1 | 9/2011 | Barghorn et al. | |
| 2011/0229413 A1 | 9/2011 | Lieberburg et al. | |
| 2011/0237537 A1 | 9/2011 | Lombard et al. | |
| 2011/0287005 A1 | 11/2011 | Hillen et al. | |
| 2011/0306756 A1 | 12/2011 | Schenk | |
| 2012/0027755 A1 | 2/2012 | Lannfelt et al. | |
| 2012/0082667 A1 | 4/2012 | Yokoseki et al. | |
| 2012/0156193 A1 | 6/2012 | Yokoseki et al. | |
| 2012/0177664 A1 | 7/2012 | Yokoseki et al. | |
| 2013/0164367 A1 | 6/2013 | Oddo et al. | |
| 2013/0216555 A1 | 8/2013 | Nitsch et al. | |
| 2013/0266514 A1 | 10/2013 | Nitsch et al. | |
| 2013/0266585 A1 | 10/2013 | Nitsch et al. | |
| 2013/0266586 A1 | 10/2013 | Nitsch et al. | |
| 2013/0344088 A1* | 12/2013 | Cosenza | A61K 9/0019 424/172.1 |
| 2014/0272950 A1 | 9/2014 | Wang et al. | |
| 2014/0274764 A1 | 9/2014 | Zhu et al. | |
| 2014/0323424 A1 | 10/2014 | Lombard et al. | |
| 2015/0030589 A1 | 1/2015 | Goldbach et al. | |
| 2015/0147343 A1 | 5/2015 | Nitsch et al. | |
| 2015/0315267 A1 | 11/2015 | Bussiere et al. | |
| 2016/0177390 A1 | 6/2016 | Feng et al. | |
| 2016/0289310 A1 | 10/2016 | Nitsch et al. | |
| 2017/0283491 A1 | 10/2017 | Nitsch et al. | |
| 2018/0134773 A1 | 5/2018 | Nitsch et al. | |
| 2018/0333487 A1 | 11/2018 | Ferrero et al. | |
| 2019/0079077 A1 | 3/2019 | Co et al. | |
| 2019/0231875 A1 | 8/2019 | Liu et al. | |
| 2019/0263896 A1 | 8/2019 | Nitsch et al. | |

FOREIGN PATENT DOCUMENTS

| | | |
|---|---|---|
| EP | 1 033 996 | 9/2000 |
| EP | 1 172 378 | 1/2002 |
| EP | 1 185 296 | 3/2002 |
| EP | 1 185 298 | 3/2002 |
| EP | 1 212 088 | 6/2002 |
| EP | 1 358 213 | 11/2003 |
| EP | 1 613 347 | 1/2006 |
| EP | 1 679 080 | 7/2006 |
| EP | 1 690 547 | 8/2006 |
| EP | 1 720 909 | 11/2006 |
| EP | 1 741 783 | 1/2007 |
| EP | 1 766 396 | 3/2007 |
| EP | 1 861 422 | 5/2007 |
| EP | 1 994 937 | 11/2008 |
| EP | 2 045 267 | 4/2009 |
| EP | 2 108 376 | 10/2009 |
| EP | 2 204 381 | 7/2010 |
| EP | 2 210 901 | 7/2010 |
| EP | 2 305 282 | 4/2011 |
| EP | 2 305 709 | 4/2011 |
| EP | 2 361 629 | 8/2011 |
| EP | 2 364 719 | 9/2011 |
| JP | 2003-509020 | 3/2003 |
| JP | 2006-265189 | 10/2006 |
| JP | 2007-536895 | 12/2007 |
| JP | 2008-524247 | 7/2008 |
| JP | 2008/528612 A | 7/2008 |
| JP | 2008/528638 A | 7/2008 |
| JP | 2008-309778 | 12/2008 |
| JP | 2009-519708 | 5/2009 |
| JP | 2010/514454 A | 5/2010 |
| JP | 2012/533548 A | 12/2012 |
| JP | 2015/510871 A | 4/2015 |
| JP | 2016/501247 A | 1/2016 |
| JP | 2016/65079 A | 4/2016 |
| JP | 2016/513635 A | 5/2016 |
| SG | 177954 | 2/2012 |
| WO | WO 93/14125 | 7/1993 |
| WO | WO 98/028007 | 7/1998 |
| WO | WO 99/50300 | 10/1999 |
| WO | WO 01/18169 | 3/2001 |
| WO | WO 01/31056 | 5/2001 |
| WO | WO 01/98361 | 12/2001 |
| WO | WO 2002030463 | 4/2002 |
| WO | WO 03/069332 | 8/2003 |
| WO | WO 03/074081 | 9/2003 |
| WO | WO 03/077858 | 9/2003 |
| WO | WO 2004/032868 | 4/2004 |
| WO | WO-2004/091658 A1 | 10/2004 |
| WO | WO 2004/095031 | 11/2004 |
| WO | WO 2004/108895 | 12/2004 |

(56) References Cited

FOREIGN PATENT DOCUMENTS

| | | |
|---|---|---|
| WO | WO 2005/018424 | 3/2005 |
| WO | WO 2005/025616 | 3/2005 |
| WO | WO 2005/047860 | 5/2005 |
| WO | WO 2005/060641 | 7/2005 |
| WO | WO 2005/123775 | 12/2005 |
| WO | WO 2006/020581 | 2/2006 |
| WO | WO 2006/050041 | 5/2006 |
| WO | WO 2006/066171 | 6/2006 |
| WO | WO 2006/103116 | 10/2006 |
| WO | WO 2006/116192 | 11/2006 |
| WO | WO 2006/118959 | 11/2006 |
| WO | WO 2007/011907 | 1/2007 |
| WO | WO 2007/012061 | 1/2007 |
| WO | WO 2007/021255 | 2/2007 |
| WO | WO 2007/067959 | 6/2007 |
| WO | WO 2007/068412 | 6/2007 |
| WO | WO 2008/081008 | 7/2008 |
| WO | WO 2008/086395 | 7/2008 |
| WO | WO 2008/103472 | 8/2008 |
| WO | WO 2008/110372 | 9/2008 |
| WO | WO 2008/131298 | 10/2008 |
| WO | WO 2008/148884 | 12/2008 |
| WO | WO 2009/033743 | 3/2009 |
| WO | WO 2009/040134 | 4/2009 |
| WO | WO 2009/094592 | 7/2009 |
| WO | WO 2010/004434 | 1/2010 |
| WO | WO 2010/032059 | 3/2010 |
| WO | WO 2010/069603 | 6/2010 |
| WO | WO-2011/008770 A2 | 1/2011 |
| WO | WO 2011/064225 | 6/2011 |
| WO | WO 2011/072091 | 6/2011 |
| WO | WO 2011/104381 | 9/2011 |
| WO | WO 2012/005838 | 1/2012 |
| WO | WO 2012/021469 | 2/2012 |
| WO | WO 2012/049570 | 4/2012 |
| WO | WO 2012/080518 | 6/2012 |
| WO | WO 2012/174262 | 12/2012 |
| WO | WO 2013/020723 | 2/2013 |
| WO | WO 2013/061163 | 5/2013 |
| WO | WO 2013/140349 | 9/2013 |
| WO | WO 2014/041069 | 3/2014 |
| WO | WO 2014/089500 | 6/2014 |
| WO | WO 2014/182631 | 11/2014 |
| WO | WO 2015/092077 | 6/2015 |
| WO | WO 2015/120233 | 8/2015 |
| WO | WO 2015/175769 | 11/2015 |
| WO | WO 2015/191825 | 12/2015 |
| WO | WO 2016/016278 | 2/2016 |
| WO | WO 2016/087944 | 6/2016 |

OTHER PUBLICATIONS

Shen et al., "Design and Analysis of Dose Escalation Studies to Mitigate Dose-Limiting Adverse Effects", Drug Information Journal, 2006, 40(1):69-78.
U.S. Appl. No. 12/522,031, U.S. Pat. No. 8,906,367, filed Mar. 1, 2010, Nitsch.
U.S. Appl. No. 13/827,673, filed Mar. 14, 2013, Nitsch.
U.S. Appl. No. 13/838,526, filed Mar. 15, 2013, Nitsch.
U.S. Appl. No. 13/841,485, filed Mar. 15, 2013, Nitsch.
U.S. Appl. No. 14/322,096, filed Jul. 2, 2014, Nitsch.
U.S. Appl. No. 15/066,304, U.S. Pat. No. 9,828,420, filed Mar. 10, 2016, Nitsch.
U.S. Appl. No. 15/791,632, U.S. Pat. No. 10,131,708, filed Oct. 24, 2017, Nitsch.
U.S. Appl. No. 16/154,920, filed Oct. 9, 2018, Nitsch.
U.S. Appl. No. 16/807,774, filed Mar. 3, 2020, Nitsch.
U.S. Appl. No. 17/072,593, filed Oct. 16, 2020, Nitsch.
U.S. Appl. No. 13/003,245, filed Apr. 4, 2011, Nitsch.
U.S. Appl. No. 14/650,200, filed Jun. 5, 2015, Bussiere.
U.S. Appl. No. 14/904,388, filed Jan. 11, 2016, Feng.
U.S. Appl. No. 15/531,960, U.S. Pat. No. 10,842,871, filed May 31, 2017, Ferrero.
U.S. Appl. No. 17/079,122, filed Oct. 23, 2020, Ferrero.
U.S. Appl. No. 16/307,364, filed Dec. 5, 2018, Boot.
U.S. Appl. No. 13/41,485, filed Mar. 15, 2013, Nitsch.
U.S. Appl. No. 15/531,960, filed May 31, 2017, Ferrero.
Kerwin, B.A., Polysorbates 20 and 80 Used in the Formulation of Protein Biotherapeutics: Structure and Degradation Pathways, Jrnl. Pharm. Sci., 97(8):2924-2935 (2008).
Lange, C. and Rudolph, R., Suppression of Protein Aggregation by L-Arginine, Curr. Pharm. Biotech., 10(4):408-14 (2009).
Aducanumab [online]. ALZFORUM, by Biomedical Research Forum, LLC, first available online Jan. 29, 2014, [Retrieved on Mar. 3, 2016], Retrieved from the Internet: URL <http://www.alzforum.org/therapeutics/aducanumab>, 6 pages.
Biogen Antibody Buoyed by Phase 1 Data and Hungry Investors [online] ALZFORUM, by Biomedical Research Forum, LLC, first available online Mar. 25, 2015, [Retrieved on Jun. 12, 2015], 9 pages.
Human-Derived SOD1 Antibodies Show Promise in ALS Mice, [online] ALZFORUM, by Biomedical Research Forum, LLC, first available online Apr. 17, 2013, [Retrieved on Jul. 28, 2014], Retrieved from the Internet: URL <http://www.alzforum.org/news/conference-coverage/human-derived-sod1-antibodies-show-promis-als-mice> 1 pages.
Multiple Dose Study of BIIB037 in Subjects With Prodromal or Mild Alzheimer's Disease, [online] ClinicalTrials.gov, U.S. National Library of Medicine, first available online Aug. 30, 2012, [Retrieved on Jul. 28, 2014], Retrieved from the Internet: URL <https://clinicaltrials.gov/ct2/show/study/NCT01677572> 1 page.
The advantages of using recombinant antibodies [online] Absolute Antibody, [Retrieved on Jun. 28, 2016], Retrieved from the Internet: URL <http://absoluteantibody.com/about-us/advantages-of-recombinant-antibodies/>, 1 page.
The Dictionary of Immunology, Academic Press, Fourth Edition, Harcourt Brace & Company, (1995), 3 pages.
Abcam, "Anti-pan Synuclein antibody (ab6176)," Abcam Inc., United States, available online on or before Jun. 26, 2012, Retrieved from the Internet: URL <http://www.abcam.com/pan-synuclein-antibody-ab6176,html>, 2 pages.
Adderson et al., "Molecular Analysis of Polyreactive Monoclonal Antibodies from Rheumatic Carditis: Human Anti-N-Acetyl glucosamine/Anti-Myosin Antibody V Region Genes," J Immunol, 161:2020-2031, Aug. 15, 1998, 13 pages.
Alloul et al., "Alzheimer's disease: a review of the disease, its epidemiology and economic impact," Arch Gerontol Geriatr, 27:198-221, Nov. 2, 1998, 33 pages.
Andreasen et al., "First Administration of the Fc-Attenuated Anti-[beta] Amyloid Antibody GSK933776 to Patients with Mild Alzheimer's Disease: A Randomized, Placebo-Controlled Study," PLOS One 10(3):e0098153 (2015).
Baba et al., "Aggregation of a-Synuclein in Lewy Bodies of Sporadic Parkinson's Disease and Dementia with Lewy Bodies," Am J Pathol 152(4):879-884, Apr. 1998, 6 pages.
Bard et al., "Epitope and isotype specificities of antibodies to β-amyloid peptide for protection against Alzheimer's disease-like neuropathology," PNAS 100(4):2023-2028, Feb. 2003, 6 pages.
Bard et al., "Peripherally administered antibodies against amyloid β-peptide enter the central nervous system and reduce pathology in a mouse model of Alzheimer disease," Nat Med 6(8):916-919, Aug. 2000, 4 pages.
Basi et al., "Structural Correlates of Antibodies Associated with Acute Reversal of Amyloid 13-related Behavioral Deficits in a Mouse Model of Alzheimer Disease," J Biol Chem, 285(5):3417-3427, Jan. 2010, 12 pages.
Bayer and Wirths, "Intraneuronal Aβ as a trigger for neuron loss: Can this be translated into human pathology?" Biochem Soc Trans, 39(4):857-861, Jan. 1, 2011, 5 pages.
BD Transduction Laboratories, "Technical Data Sheet: Purified Mouse Anti-a-Synuclein," BD Biosciences, available online on or before Jun. 27, 2012, [Retrieved on Mar. 3, 2016], Retrieved from the Internet: URL<http://www.bdbiosciences.com/ds/pm/tds/610787.pdf>, 2 pages.

(56) References Cited

OTHER PUBLICATIONS

Becker et al., "Stimulation of endogenous neurogenesis by anti-EFRH immunization in a transgenic mouse model of Alzheimer's disease," Proc. Natl. Acad. Sci. USA 104(5):1691-1696, Jan. 2007, 6 pages.

Bernasconi et al., "Maintenance of Serological Memory by Polyclonal Activation of Human Memoiy B Cells," Science 298:2199-2202, Dec. 2002, 3 pages.

Biscaro et al., "Aβ immunotherapy Protects Morphology and Survival of Adult-Born Neurons in Doubly Transgenic APP/PS1 Mice," J Neurosci 29(45): 14108-14119, Nov. 2009, 12 pages.

Bohrmann et al., "Gantenerumab: A Novel Human Anti-A13 Antibody Demonstrates Sustained Cerebral Amyloid-13 Binding and Elicits Cell-Mediated Removal of Human Amyloid-β," J Alzheimer's Dis, 28(l):49-69, 2012, 21 pages.

BusinessWire [online], "Biogen Presents New Data from Phase 1B Study of Investigational Alzheimer's Disease Treatment Aducanumab (BIIB037) at Alzheimer's Association International Conference® 2015," Jul. 22, 2015, [Retrieved on Mar. 3, 2016], Retrieved from the Internet: URL<http://www.businesswire.com/news/home/20150722005352/en/Biogen-Presents-Data-Phase-1B-Study-Investigational>, 5 pages.

Buttini et al., "β-Amyloid Immunotherapy Presents Synaptic Degeneration in a Mouse Model of Alzheimer's Disease," J Neurosci 25:9096-9101, Oct. 2005, 6 pages.

Buxbaum, "The systemic amyloidosis," Current Opinion in Rheumatology, 16:67-75 (2004).

Buxbaum et al. "Molecular dissection of NRG1-ERBB4 signaling implicates PTPRZ1 as a potential schizophrenia susceptibility gene," Mol. Psychiatry 2008;13:162-172.

Campbell, "β-amyloid: friend or foe," Med Hypot, 56(3):388-391, Mar. 2001, 4 pages.

Casset et al., "A peptide mimetic of an anti-CD4 monoclonal antibody by rational design," Biochem and Biophys Res Comm 307:198-205, Jul. 2003, 8 pages.

Chen et al., "Selection and Analysis of an Optimized Ant-VEGF Antibody: Crystal Structure of an Affinity-matured Fab in Complex with Antigen," J Mol Biol 293:865-881, Nov. 1999, 17 pages.

Choi et al. "Fine epitope mapping of monoclonal antibodies specific to human alpha-synuclein," Neuroscience Letters, 397(1-2):53-58, Apr. 2006, 6 pages.

ClinicalTrials.gov [online], "221AD301 Phase 3 Study of Aducanumab (BIIB037) in Early Alzheimer's Disease (ENGAGE)," Last updated Apr. 24, 2019, [Retrieved on May 19, 2019], retrieved from: URL<https://www.clinicaltrials.gov/ct2/show/study/NCT02477800>, 6 pages.

Cohn, "Introduction to Surrogate Markers," Circulation, 109[suppll IV]: IV-20-IV-21 (2004).

Das et al. "Amyloid-β Immunization Effectively Reduces Amyloid Deposition in FcRy Knock-Out Mice," J Neurosci, 23(24):8532-8538, Sep. 2003, 7 pages.

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol 169:3076-3084, Sep. 2002, 9 pages.

DeMattos et al., "Peripheral anti-Aβ antibody alters CNS and plasma Aβ clearance and decreases brain Aβ burden in a mouse model of Alzheimer's disease," Proc Natl Acad Sci USA, 98:8850-8855, Jul. 2001, 6 pages.

Department Of Health And Human Services, Food And Drug Administration, Memorandum of Meeting Minutes with Biogen Idec, with cover letter and signature page by Director Russell G. Katz, dated Nov. 19, 2009; received Dec. 2, 2009, 9 pages.

DiFrancesco et al., "Anti-Aβ autoantibodies in amyloid related imaging abnormalities (ARIA): candidate biomarker for immunotherapy in Alzheimer's disease and cerebral amyloid angiopathy," Frontiers in Neurology, 2015, 6:1-6.

Du et al., "Human anti-β-amyloid antibodies block β-amyloid fibril formation and prevent β-amyloid-induced neurotoxicity," Brain 126:1935-1939, Sep. 2003, 5 pages.

Dunn et al., "The Immunobiology of Cancer Immunosurveillance and Immunoediting," Immunity 21:137-1498, Aug. 2004, 12 pages.

Dunstan et al., "The role of brain macrophages on the clearance of amyloid plaques following the treatment of Tc2576 with BIIB037," Alzheimer's & Dementia: The Journal of the Alzheimer's Association, 7(4):S700, Jul. 2011, 3 pages.

El-Agnaf et al., "a-Synuclein implicated in Parkinson's disease is present in extracellular biological fluids, including human plasma," Faseb J., 17( 13): 1945-1947, Oct. 2003, 3 pages.

El-Agnaf et al., "Detection of oligomeric forms of a-synuclein protein in human plasma as a potential biomarker for Parkinson's disease," Faseb J., 20:419-425, 2006, 7 pages.

Emadi et al., "Inhibiting Aggregation of a-Synuclein with Human Single Chain Antibody Fragments," Biochem, 43(10):2871-2878, Mar. 2004, 10 pages.

Emadi et al., "Isolation of a human single chain antibody fragment against oligomeric a-synuclein that inhibits aggregation and prevents a-synuclein-induced toxicity" J. Mol Biol, 368(4):1132-1144, May 2007, 13 pages.

Email from Edward Stuart, CEO of Neuroimmune Therapeutics AG, to Leslie Coney, Biogen IDEC, dated Nov. 1, 2007, 1 page.

Email from Jan Grimm of Neuroimmune, to Ken Rhodes of Biogen IDEC, dated Oct. 13, 2009, 1 page.

Emmanouilidou et al., "Assessment of a-Synuclein Secretion in Mouse and Human Brain Parenchyma," PLoS ONE, 6(6):e22225, doi: 10.1371/journal.pone.0022225, Jul. 2011, 9 pages.

Esposito et al., "Neuronal Differentiation in the Adult Hippocampus Recapitulates Embryonic Development," J. Neurosci. 25(44):10074-10086, Nov. 2005, 13 pages.

European Office Action in European Application No. 09786187.6, dated Nov. 11, 2016, 8 pages.

European Search Report and Written Opinion in European Application No. 11185486, dated Mar. 7, 2012, 11 pages.

European Search Report and Written Opinion in European Application No. 12802721, dated Feb. 2, 2015, 16 pages.

Extended Search Report and Written Opinion in European Application No. 12846452, dated May 21, 2015, 4 pages.

European Extended Search Report in European Application No. 14822788.7, dated Dec. 15, 2016, 8 pages.

European Search Report in European Application No. 17169749.3, dated Aug. 1, 2017, 14 pages.

Ferrero et al., "First-in-human, double-blind, placebo-controlled, single-dose escalation study of aducanumab (BIIB037) in mild-to-moderate Alzheimer's disease," Alzheimer's & Dementia: Translational Research & Clinical Interventions, 2016, 2(3):169-176.

Ge et al., "GABA regulates synaptic integration of newly generated neurons in the adult brain," Nature 439(2):589-593, Jul. 2006, 10 pages.

Gelfanova et al., "Quantitative analysis of amyloid-beta peptides in cerebrospinal fluid using immunoprecipitation and MALDI-Tof mass spectrometry," Briefings in Functional Genomics and Proteomics, 6(2):149-158, Jun. 1, 2007, 10 pages.

George et al., "a-Synuclein transgenic mice exhibit reduced anxiety-like behavior," Exp Neural, 210:788-792, Apr. 2008, 5 pages.

George, "The Synucleins," Genome Biol, 3(l):reviews 3002.1-3002.6, Dec. 2001, 6 pages.

Geylis and Steinitz, "Immunotherapy of Alzheimer's disease (AD): From murine models to anti-amyloid beta (Aβ) human monoclonal antibodies," Autoimmunity Reviews 5:33-39, Jan. 2006, 7 pages.

Geylis et al., "Human monoclonal antibodies against amyloid-beta from healthy adults," Neurobiol of Aging, 26:597-606, May 2005, 10 pages.

Giasson et al., "A Panel of Epitope-Specific Antibodies Detects Protein Domains Distributed Throughout Human a-Synuclein in Lewy Bodies of Parkinson's Disease," J Neurosci Res, 59:528-533, 2000, 6 pages.

Giasson et al., "Neuronal a-Synucleinopathy with Severe Movement Disorder in Mice Expressing A53T Human a-Synuclein," Neuron, 34:521-533, May 2002, 13 pages.

(56) References Cited

OTHER PUBLICATIONS

Giraudon et al., "Semaphorin CD100 from Activated T Lymphocytes Induces Process Extension Collapse in Oligodendrocytes and Death of Immature Neural Cells," J Immunol, 172:1246-1255, Jan. 2004, 11 pages.
Gregory et al., "What is the dominant Aβ species in human brain tissue? A review," Neurotoxicity research, 2005, 7(1-2):29-41.
Gupta et al., "A Novel human-derived antibody against NY-ESO-1 improves the efficacy of chemotherapy," Cancer Immunity, 13:1-9 (Jan. 2013).
Haass et al., "Amyloid β-peptide is produced by cultured cells during normal metabolism," Nature, 359:322-325, Sep. 1992, 4 pages.
Hampel et al., "Biological markers of amyloid β-related mechanisms in Alzheimer's disease," Experimental neurology, 2010, 223(2):334-346.
Hantman and Perl, "Molecular and Genetic Features of a Labeled Class of Spinal Substantia Gelatinosa Neurons in a Transgenic Mouse," J Comp Neurol, 492:90-100, Wiley-Liss, Inc., 2005, 11 pages.
Hasan Mohajeri et al., "Passive immunization against beta-amyloid peptide protects central nervous system (CNS) neurons from increased vulnerability associated with an Alzheimer's disease-causing mutation," Journal of Biological Chemistry, American Society for Biochemistry and Molecular Biology U.S., 277(36):33012-33017 (Sep. 2002).
Hashimoto et al., "A novel approach for Aβ1-40 quantification using immuno-PCR," J Neurosci Meth, 205(2):364-367, Jan. 25, 2012, 4 pages.
Ho et al., "In vivo imaging of adult human hippocampal neurogenesis: progress, pitfalls and promise," Mol Psychiatry, 18(4):404-416, Nature Publishing Group, Feb. 2013, 14 pages.
Hock, "Biochemical Aspects of Dementias," Dialogues in Clinical Neuroscience, 2003, 5(1):27-33.
Hock and Nitsch, "Clinical Observations with AN-1792 Using TAPIR Analyses," Neurodeg Dis 2:273-276, 2005, 4 pages.
Hock et al., "Antibodies against β-Amyloid Slow Cognitive Decline in Alzheimer's Disease," Neuron, 38(4):547-554, May 2003, 8 pages.
Hock et al., "Generation of antibodies specific for β-amyloid by vaccination of patients with Alzheimer disease," Nat Med, 8(11):1270-1275, 2002, 6 pages.
Holcomb et al., "Accelerated Alzheimer-type phenotype in transgenic mice carrying both mutant amyloid precursor protein and presenilin I transgenes," Nat. Med. 4(1):97-100, Nature Publishing Group, Jan. 1998, 4 pages.
Holm et al., "Functional mapping and single chain construction of the anti-cytokeratin 8 monoclonal antibody TS1," Mol Immunol 44:1075-1084, 2007, 10 pages.
Hsiao et al., "Correlative Memory Deficits, Aβ Elevation, and Amyloid Plaques in Transgenic Mice," Science 274(5284):99-102, American Associate for the Advancement of Science, Oct. 1996, 4 pages.
Hyman et al., "Autoantibodies to Amyloid-β and Alzheimer's Disease," Ann Neurol 49:808-810, 2001, 5 pages.
International Preliminary Report on Patentability and Written Opinion in International Application No. PCT/EP2008/000053, dated Jul. 7, 2009, 10 pages.
International Preliminary Report on Patentability and Written Opinion in International Application No. PCT/EP2017/056031, dated Sep. 18, 2018, 8 pages.
International Preliminary Report on Patentability and Written Opinion in International Application No. PCT/IB2009/006666, dated Jan. 11, 2011, 10 pages.
International Preliminary Report on Patentability and Written Opinion in International Application No. PCT/IB2015/002465, dated Jun. 6, 2017, 9 pages.
International Preliminary Report on Patentability and Written Opinion in International Application No. PCT/US2013/073700, dated Jun. 9, 2015, 10 pages.
International Preliminary Report on Patentability and Written Opinion in International Application No. PCT/US2014/045994, dated Jan. 12, 2016, 15 pages.
International Preliminary Report on Patentability and Written Opinion in International Application No. PCT/US2015/030753, dated Nov. 15, 2016, 7 pages.
International Preliminary Report on Patentability and Written Opinion in International Application No. PCT/US2015/035282, dated Dec. 15, 2016, 12 pages.
International Preliminary Report on Patentability and Written Opinion in International Application No. PCT/EP2017/063711, dated Dec. 11, 2018, 14 pages.
International Search Report and Written Opinion in International Application No. PCT/US2012/062430, dated Jan. 24, 2013, 10 pages.
International Search Report and Written Opinion in International Application No. PCT/EP2009/009186, dated Mar. 12, 2010, 11 pages.
International Search Report and Written Opinion in International Application No. PCT/EP2017/056031, dated May 10, 2017, 11 pages.
International Search Report and Written Opinion in International Application No. PCT/EP2017/063711, dated Oct. 23, 2017, 21 pages.
International Search Report and Written Opinion in International Application No. PCT/IB2009/006666, dated Feb. 22, 2010, 16 pages.
International Search Report and Written Opinion in International Application No. PCT/IB2015/002465, dated Jun. 9, 2016, 18 pages.
International Search Report and Written Opinion in International Application No. PCT/US2012/043701, dated Sep. 26, 2012, 11 pages.
International Search Report and Written Opinion in International Application No. PCT/US2013/073700, dated Mar. 3, 2014, 13 pages.
International Search Report and Written Opinion in International Application No. PCT/US2014/045994, dated Nov. 3, 2014, 19 pages.
International Search Report and Written Opinion in International Application No. PCT/US2015/030753, dated Aug. 27, 2015, 11 pages.
International Search Report and Written Opinion in International Application No. PCT/US2015/035282, dated Sep. 29, 2015, 18 pages.
International Search Report and Written Opinion in International Application No. PCT/US2018/047508, dated Oct. 20, 2018, 17 pages.
Invitrogen Corp, "Mouse anti-a-Synuclein: For In Vitro Diagnostic Use," Product information, revision date Aug. 2008, accessed on Jul. 2, 2012, 3 pages.
Iwai et al., "Non-Aβ Component of Alzheimer's Disease Amyloid (NAG) Is Amyloidogenic," Biochemistry, 34:10139-10145, 1995, 8 pages.
Jakes et al., "Epitope mapping of LB509, a monoclonal antibody directed against human a-synuclein," Neurosci Lett, 269:13-16, 1999, 4 pages.
Janus et al., "Aβ peptide immunization reduces behavioral impairment and plaques in a model of Alzheimer's disease," Nature 408: 979-982, Dec. 2000, 4 pages.
Janus et al., "Spatial learning in transgenic mice expressing human presenilin 1 (PS1) transgenes," Neurobiol Aging, 21(4):541-549, 2000, 9 pages.
Jawhar et al., "Pyroglutamate amyloid-β (Aβ): a hatchet man in Alzheimer disease," J Biol Chem, 286(45):38825-38832, Nov. 11, 2011, 9 pages.
Jensen et al., "Residues in the synuclein consensus motif of the a-synuclein fragment, NAG, participate in transglutaminase-catalyzed cross-linking to Alzheimer-disease amyloid 13A4 peptide," Biochem J, 310:91-94, Aug. 1995, 4 pages.
Jin et al., "Vascular endothelial growth factor (VEGF) stimulates neurogenesis in vitro and in vivo," Proc Natl Acad Sci USA 99(18): 11946-11950, National Academy of Sciences, Sep. 2002, 5 pages.

(56) References Cited

OTHER PUBLICATIONS

Kadir et al., "Position emission tomography imaging and clinical progression in relation to molecular pathology in the first Pittsburgh Compound B positron emission tomography patient with Alzheimer's disease," Brain, 134(1):301-317, Jan. 1, 2011, 17 pages.

Kahle et al., "Selective Insolubility of a-Synuclein in Human Lewy Body Diseases Is Recapitulated in a Transgenic Mouse Model," Am J Pathol, 159(6):2215-2225, Dec. 2001, 11 pages.

Kahle et al., "Subcellular Localization of Wild-Type and Parkinson's Disease-Associated Mutant a-Synuclein in Human and Transgenic Mouse Brain," J Neurosci, 20(17):6365-6373, Sep. 2000, 9 pages.

Kastanenka et al., "Amelioration of calcium dyshomeostasis by immunotherapy with BIIB037 in Tg2576 mice," Alzheimer's & Dementia: The Journal of The Alzheimer's Association, 9(4):P508, Jul. 2013.

Kawarabayashi et al., "Age-Dependent Changes in Brain, CSF, and Plasma Amyloid 13 Protein in the Tg2576 Transgenic Mouse Model of Alzheimer's Disease," J Neurosci, 21 (2):372-381, Jan. 2001, 10 pages.

Knobloch et al., "Intracellular Aβ and cognitive deficits precede β-amyloid deposition in transgenic arcAβ mice," Neurobiol Aging 28(9):1297-1306, Sep. 2007, 10 pages.

Knowles et al., "The p75 neurotrophin receptor promotes amyloid-β (1-42)-induced neuritic dystrophy in vitro and in vivo," Journal of Neuroscience, 2009, 29(34):10627-10637.

Kohler and Milstein, "Continuous cultures of fused cells secreting antibody of predefined specificity," Nature 256:495-497, 1975, 5 pages.

Kumanogoh et al., "Requirement for the Lymphocyte Semaphorin, CD100, in the Induction of Antigen-Specific T Cells and the Maturation of Dendritic Cells," J Immunol, 169:1175-1181, Aug. 2002, 7 pages.

Lai et al., "A First-In-Human Study of Ban2401, A Novel Monoclonal, Antibody Against Beta-Amyloid Protofibrils", Oral Sessions: 04-05: Therapeautics: Clinical Trials III, Jul. 2013, 9(4):P689.

Larrick et al., "Recombinant antibodies," Hum Antibod Hybridoma, 2:172-189 (1991), abstract.

Laske et al., Higher BDNF serum levels predict slower cognitive decline in Alzheimer's disease patients, International Journal of Neuropsychopharmacology, 14(3):399-404 (Apr. 2011).

Laurén et al., "Cellular prion protein mediates impairment of synaptic plasticity by amyloid-beta oligomers," Nature 457: 1128-1132, Macmillan Publishers Limited, 2009, 13 pages.

Lee et al., "Enzyme-linked immunosorbent assays for alpha-synuclein with species and multimeric state specificities," J Neurosci Meth, 199(2):249-257, 2011, 9 pages.

Lee et al., "Stereological analysis of microvascular parameters in a double transgenic model of Alzheimer's disease," Brain Res Bull 65(4) :3 17-322, Elsevier Science, 2005, 6 pages.

Lee et al., "Targeting Amyloid-beta Peptide (Abeta) Oligomers by Passive Immunization with a Conformation -selective Monoclonal Antibody Improves Learning and Memory in abeta Precursor Protein (APP) Transgenic Mice," Journal of Biological Chemistry, American Society for Biochemistry and Molecular Biology, 281(7):4292-4299, Feb. 2006.

Lehman et al., "Amino acid sequence of the variable region of a human μ chain: Location of a possible JH segment," Proc Natl Acad Sci USA, 77(6):3239-3243, Jun. 1980, 5 pages.

Lim et al., "APOE and BDNF polymorphisms moderate amyloid β-related cognitive decline in preclinical Alzheimer's disease," Mol Psychi, 1-7, Oct. 7, 2014, 7 pages.

Lim et al., "BDNF Val66Met, Ab amyloid, and cognitive decline in preclinical Alzheimer's disease," Neurobiol of Aging, 34(ll):2457-2464, Jun. 13, 2013, 8 pages.

Lim et al., "Effect of BDNF Val66Met on Memory Decline and Hippocampal Atrophy in Prodromal Alzheimer's Disease: A Preliminary Study," PLoS One, 9(1):1-5, Jan. 27, 2014, 5 pages.

Lippa et al., "Antibodies to a-Synuclein Detect Lewy Bodies in Many Down's Syndrome Brains with Alzheimer's Disease," Ann Neural, 45(3):353-357, Mar. 1999, 7 pages.

Liu et al., "Amyloid β peptide alters intracellular vesicle trafficking and cholesterol homeostasis," Proc Natl Acad Sci USA, 95:13266-13271, Oct. 1998, 6 pages.

Lobello et al., "Targeting Beta Amyloid: A Clinical Review of Immunotherapeutic Approaches in Alzheimer's Disease," International Journal of Alzheimer's Disease 6(4):S305-14 (2012).

Lopez-Toledano and Shelanksi, "Neurogenic Effect of β-Amyloid Peptide in the Development of Neural Stem Cells," J Neurosci, 24:5439-5444, Jun. 2004, 6 pages.

Lewczuk et al., "Amyloid β peptides in cerebrospinal fluid as profiled with surface enhanced laser desorption/ionization time-of-flight mass spectrometry: evidence of novel biomarkers in Alzheimer's disease," Biol Psych, 55(5):524-530, Mar. 1, 2004, 7 pages.

Lu et al., "BDNF-based synaptic repair as a disease-modifying strategy for neurodegenerative diseases," Nature Reviews Neuroscience, 14:401-416 (May 2013).

Lynch et al., "An ScFv Intrabody Against the Non-Amyloid Component of Alpha Synuclein Reduces Intracellular Aggregation and Toxicity," NIH Public Access Author Manuscript; final publication in J. Mol Biol. 377(1):136-147, Mar. 2007, 17 pages.

MacCallum et al., "Antibody-antigen Interactions: Contact Analysis and Binding Site Topography," J Mol Biol 262:732-745, 1996, 14 pages.

Maguire-Zeiss et al., "Identification of human alpha-synuclein specific single chain antibodies," Biochem Biophys Res Commun, 349(4):1198-1205, 2006, 25 pages.

Masliah et al., "Dopaminergic loss and inclusion body formation in alpha-synuclein mice: implications for neurodegenerative disorders," Science, 287(5456):1265-1269, Feb. 2000, 5 pages.

Masliah et al., "Effects of a-Synuclein Immunization in a Mouse Model of Parkinson's Disease," Neuron, 46:857-868, 2005, 12 pages.

Masters et al., "Amyloid plaque core protein in Alzheimer disease and Down syndrome," Proc Natl Acad Sci USA 82:4245-4249, Jun. 1985, 5 pages.

Masuda et al., "Inhibition of a-synuclein fibril assembly by small molecules: Analysis using epitope specific antibodies," FEBS Lett, 583(4):787-791, Feb. 2009, 5 pages.

Mcheyzer-Williams and Ahmed, "B cell memory and the long-lived plasma cell," Curr Opin Immunol, 11:172-179, Apr. 1999, 10 pages.

McLaurin et al., "Therapeutically effective antibodies against amyloid-13 peptide target amyloid-β residues 4-10 and inhibit cytotoxicity and fibrillogenesis," Nat Med, 8: 1263-1269, Oct. 2002, 7 pages.

Meyer-Luehmann et al., "A reporter of local dendritic translocation shows plaque-related loss of neural system function in APP-transgenic mice," Journal of Neuroscience, 2009, 29(40):12636-12640.

Miller and Messer, "Intrabody Applications in Neurological Disorders: Progress and Future Prospects," Molecular Therapy, 12(3):394-401, Sep. 2005, 8 pages.

Mollenhauer et al., "Direct quantification of CSF a-synuclein by ELISA and first cross-sectional study in patients with neurodegeneration," Exp Neural, 213(2):315-325, Oct. 2008, 11 pages.

Mollenhauer et al., "Quantification of alpha-synuclein in cerebrospinal fluid as a biomarker candidate: review of the literature and considerations for future studies," Biomarkers in Medicine, 4(5):683-699, 2010, 17 pages.

Morar-Mitrica et al., "Development of a stable low-dose aglycosylated antibody formulation to minimize protein loss during intravenous administration," MAbs, 2015, 7(4):792-803.

Moreth et al., "Passive anti-amyloid immunotherapy in Alzheimer's disease: What are the most promising targets?," Immunity and Ageing, Biomed Central, London, GB, 10(1):18, May 2013.

Morgan et al., "Aβ peptide vaccination prevents memory loss in an animal model of Alzheimer's disease," Nature, 408:982-985, Dec. 2000, 13 pages.

Mougenot et al., "Production of a monoclonal antibody, against human a-synuclein, in a subpopulation of C57BL/6J mice, presenting a deletion of the a-synuclein locus," J Neurosci Meth, 192(2):268-276, 2010, 9 pages.

(56) References Cited

OTHER PUBLICATIONS

Mruthinti et al., "Autoimmunity in Alzheimer's disease: increased levels of circulating IgGs binding Aβ and RAGE peptides," Neurobiol Aging, 25:1023-1032, 2004, 10 pages.

Mueggler et al., "Compromised Hemodynamic Response in Amyloid Precursor Protein Transgenic Mice," J Neurosci, 22:7218-7224, Aug. 2002, 7 pages.

Muller et al., "TransMabs: cell penetrating antibodies, the next generation," Expert Opin Biol Ther, 5(2):237-241, Apr. 2005, 5 pages.

GenBank Accession No. S56746, GI No. 1362748, "alpha-synuclein, NAC—human (fragment)," dated Jul. 17, 2007, 1 page.

GenBank Accession No. P37840.1, GI No. 586067, "RecName: Full=Alpha-synuclein; AltName: Full=Non-A beta component of AD amyloid; AltName: Full=Non-A4 component of amyloid precursor; Short-NACP," dated Jun. 15, 2012, 11 pages.

Neff et al., "Immunotherapy and naturally occurring autoantibodies in neurodegenerative disorders," Autoimmunity Reviews, 7:501-507, Jun. 2008, 7 pages.

Novak et al., "Efficacy and Safety of Monthly Subcutaneous Bapineuzumab", Alzheimer's and Dementia, Jul. 2014, 10(4):P25, Abstract IC-P-041.

O'Nuallain et al., "Conformational Abs recognizing a generic amyloid fibril epitope," Proceedings National Academy of Sciences, 99(3):1485-1490, Feb. 2002.

Orgogozo et al., "Subacute meningoencephalitis in a subset of patients with AD after Aβ 42 immunization," Neurology, 61(1):46-54, Jul. 2003, 11 pages.

Padlan et al., "Structure of an antibody-antigen complex: Crystal structure of the HyHEL-10 Fab-lysozyme complex," Proc Natl Acad Sci USA, 86(15):5938-5942, Aug. 1989, 5 pages.

Palop et al., "Aberrant Excitatory Neuronal Activity and Compensatory Remodeling of Inhibitory Hippocampal Circuits in Mouse Models of Alzheimer's Disease," Neuron 55(5):697-711, Cell Press, Sep. 2007, 15 pages.

Pang, "Mass Spectrometry-Based Structural Probing of Amyloid β-Protein," http://gradworks.umi.com/34/97/3497449.html, 202 pages.

Papachroni et al., "Autoantibodies to alpha-synuclein in inherited Parkinson's disease," J Neurochem, 101 :749-756, May 2007, 8 pages.

Patrias et al., "Specific antibodies to soluble alpha-synuclein conformations in intravenous immunoglobulin preparations," Clin. Exp. Immunol., 161 :527-535, Sep. 2010, 9 pages.

Paul, Editor, Fundamental Immunology, Third Edition, Raven Press, New York, pp. 292-295, 1993, 6 pages.

Perrin et al., "Epitope mapping and specificity of the anti-a-synuclein monoclonal antibody Syn-1 in mouse brain and cultured cell lines," Neurosci. Lett., 349(2):133-135, 2003, 3 pages.

Peters and Kaiserman-Abramof, "The Small Pyramidal Neuron of the Rat Cerebral Cortex. The Perikaryon, Dendrites and Spines," Am J Anat, 127:321-356, 1970, 35 pages.

Pfeifer et al., "Cerebral Hemorrhage After Passive Anti-Aβ Immunotherapy," Science, 298:1379, 2002, 3 pages.

Piantadosi et al., "Abstracts from the Program of the Second Annual Meeting of the American Society for Experimental Neurotherapeutics, Washington, DC, Mar. 23-25, 2000." American Society for Experimental Neurotherapeutics Abstracts, Arch Neurol., 57:1233-1239 (2000).

Piazza et al., "Amyloid-Related Imaging Abnormalities (ARIA) in Immunotherapy Trials for Alzheimer's Disease: Need for Prognostic Biomarkers?," Journal of Alzheimer's Disease, 2016, 52(2):417-420.

Plant et al., "The production of amyloid beta peptide is a critical requirement for the viability of central neurons," J Neurosci, 23(13):5531-5535, Society for Neuroscience, Jul. 2003, 5 pages.

Plümpe et al., "Variability of double cortin-associated dendrite maturation in adult hippocampal neurogenesis is independent of the regulation of precursor cell proliferation," BMC Neurosci, 7:77, Nov. 2006, 14 pages.

Portelius et al., "Characterization of Amyloid β Peptides in Cerebrospinal Fluid by an Automated Immunoprecipitation Procedure Followed by Mass Spectrometry," J Proteome Res, 6(11):4433-4439, Nov. 1, 2007, 7 pages.

Portelius et al., "Determination of β-Amyloid Peptide Signatures in Cerebrospinal Fluid Using Immunoprecipitation-Mass Spectrometry," J Proteome Res, 5(4):1535-3893, Apr. 1, 2006, 7 pages.

Priller et al., "Synapse Formation and Function Is Modulated by the Amyloid Precursor Protein," J Neurosci, 26(27):7212-7221, Jul. 2006, 10 pages.

Qiu et al., "Small antibody mimetics comprising two complementarity-determining regions and a framework region for tumor targeting," Nature Biotech 25:921-929, Aug. 2007, 9 pages.

Racke et al., "Exacerbation of Cerebral Amyloid Angiopathy-Associated Micro hemorrhage in Amyloid Precursor Protein Transgenic Mice by Immunotherapy is Dependent on Antibody Recognition of Deposited Forms of Amyloid β," J Neurosci 25:629-636, Jan. 2005, 8 pages.

Robert et al., "Engineered antibody intervention strategies for Alzheimer's disease and related dementias by targeting amyloid and toxic oligomers" Protein Eng Des Sel, 22(3):199-208, 2009, 10 pages.

Rudikoff et al., "Single amino acid substitution altering antigen-binding specificity," Proc Natl Acad Sci, 79:1979-1983, Mar. 1982, 5 pages.

Ruszczycki et al., "Sampling issues in quantitative analysis of dendritic spines morphology," BMC Bioinformatics, 13:213, 2012, 12 pages.

Ryu and Chen, "Development of Alzheimer's disease imaging agents for clinical studies," Front Biosci, 13:777-789, Jan. 2008, 13 pages.

Schenk et al., "Amyloid-β immunotherapy for Alzheimer's disease: the end of the beginning," Nat Rev Neurosci, 3(10):824-828, Oct. 2002, 6 pages.

Schenk et al., "Immunization with amyloid-beta attenuates Alzheimer-disease-like pathology in the PDAPP mouse," Nature, 400:173-177, Jul. 1999, 5 pages.

Seitz et al., "Isolation und Charakterisierung eines physiologisch vorkommenden Autoantikorpers gegen humanes alpha-Synuclein," 35:S86, AbstractP528, Sep. 2008, 6 pages.

Selkoe, "Alzheimer's Disease," Cold Spring Harbor Perspectives in Biology, 2011, 3(7):a004457.

Serrano-Pozo et al., "Neuropathological Alterations in Alzheimer Disease," Cold Spring Harb. Perspect. Med., 1 :a006189, 23 pages, 2011, 23 pages.

Sevigny et al., "Aducanumab (BIIB037), an anti-amyloid beta monoclonal antibody, in patients with prodromal or mild Alzheimer's disease: Interim results of a randomized, double-blind, placebo-controlled, phase 1b study," Alzheimer's & Dementia: The Journal of the Alzheimer's Association, 2015, 11(7):277, 1 page.

Sevigny, et al., "Randomized double-blind, placebo-controlled, phase 1b study of aducanumab (BIIB037), an anit-Ab monoclonal anti-body, in patients with prodromal or mild Alzheimer's disease; interim results by disease stage and ApoE4 status," Neurology 85(4):E44 (2015).

Sevigny et al., "The antibody aducanumab reduces Aβ plaques in Alzheimer's disease," Nature, 2016, 537(7618):50-56.

Sevigney et al., "A Single Ascending Dose Study of BIIB037 in People with Mild to Moderate Alzheimer's Disease", Alzheimer's and Dementia, Jul. 2013, 9(4):P290, Abstract P1-359.

Shankar et al., "Natural oligomers of the Alzheimer amyloid-beta protein induce reversible synapse loss by modulating an NMDA-type glutamate receptor-dependent signaling pathway," J Neurosci, 27(11):2866-2875, Mar. 2007, 10 pages.

Shi et al., "The Class IV Semaphorin CD100 Plays Non redundant Roles in the Immune System: Defective Band T Cell Activation in CD100-Deficient Mice," Immunity, 13:633-642, Nov. 2000, 10 pages.

Sierra et al., "Adult human neurogenesis: from microscopy to magnetic resonance imaging," Front Neurosci, 5(47):1-18, Apr. 2011, 18 pages.

(56) References Cited

OTHER PUBLICATIONS

Sigma-Aldrich, Inc., "Monoclonal Anti-a-Synuclein. Clone Syn211. Purified mouse immunoglobulin. Product No. S 5566," Product Information, updated Jan. 2003, accessed on Mar. 3, 2016, 2 pages.
Sigmund, C., "Viewpoint: Are studies in genetically altered mice out of control?" Arterioscler. Thromb. Vasc. Biology 20:1425-1429 (2000).
Simpson et al., "Antibodies to normal and Alzheimer human brain structures from non-immunized mice of various ages," FEBS Letters 217:62-64, Jun. 1987, 3 pages.
Simpson et al., "Autoantibodies to Alzheimer and Normal Brain Structures from Virus-Transformed Lymphocytes," J Neuroimmunol, 13:1-8, 1986, 4 pages.
Skovronsky et al., "Neurodegenerative Diseases: New Concepts of Pathogenesis and Their Therapeutic Implications," Annu. Rev. Pathol. Mech. Disease, 1:151-170 (2006).
SNP Cluster Report: rs6946211, [accessed: Apr. 19, 2017], retrieved from the internet: URL <https://www.ncbi.nlm.nih.gov/SNP/snp_ref.cgi?rs=6946211&pt=1V7XNyo5DVBB_0NHALSkRXG4eofetRo6uOUrVB6VklwEM4a5d>, 3 pages.
Sorra and Harris, "Overview on the Structure, Composition, Function, Development and Plasticity of Hippocampal Dendritic Spines," Hippocampus 10:501-511, 2000, 11 pages.
Supplementary European Search Report in European Application No. 13860755, dated Sep. 20, 2016, 13 pages.
Supplementary European Search Report in European Application No. 14822788, dated Dec. 16, 2016, 8 pages.
Thakker et al., "Intracerebroventricular amyloid-β antibodies reduce cerebral amyloid angiopathy and associated micro-hemorrhages in aged Tg2576 mice" Proc Natl Acad Sci USA, 106(11):4501-4506, Mar. 2009, 6 pages.
Traggiai et al., "An efficient method to make human monoclonal antibodies from memory B cells: potent neutralization of SARS coronavirus," Nat Med, 10:871-875, Aug. 2004, 5 pages.
Turner et al., "Roles of amyloid precursor protein and its fragments in regulating neural activity, plasticity and memory," Prog Neurobiol 70(1):1-32, 2003, 32 pages.
Ueda et al., "Molecular cloning of cDNA encoding an unrecognized component of amyloid in Alzheimer's disease," Proc Natl Acad Sci, 90:11282-11286, Dec. 1993, 5 pages.
United States Office Action in U.S. Appl. No. 12/522,031, dated Dec. 10, 2012, 20 pages.
United States Office Action Summary in U.S. Appl. No. 12/522,031, dated May 23, 2012, 10 pages.
United States Office Action in U.S. Appl. No. 12/522,031, dated Jun. 26, 2013, 6 pages.
United States Office Action in U.S. Appl. No. 13/003,245, dated Apr. 23, 2013, 13 pages.
United States Office Action in U.S. Appl. No. 13/003,245, dated Aug. 28, 2012, 33 pages.
U.S. Appl. No. 09/724,319, filed Nov. 27, 2012, 111 pages.
Vajdos et al., "Comprehensive Functional Maps of the Antigen-binding Site of an Anti-ErbB2 Antibody Obtained with Shotgun Scanning Mutagenesis," J Mol Biol 320:415-428, 2002, 14 pages.
Van Der Putten et al., "Neuropathology in Mice Expressing Human a-Synuclein," J Neurosci, 20(16):6021-6029, Aug. 2000, 9 pages.
Van Muiswinkel et al., "The amino-terminus of the amyloid-β protein is critical for the cellular binding and consequent activation of the respiratory burst of human macrophages," Journal of neuroimmunology, 1999, 96(1):121-130.
VanPraag et al., "Functional neurogenesis in the adult hippocampus," Nature 415:1030-1034, Feb. 2002, 5 pages.
Wall, RJ, "Transgenic livestock: Progress and prospects for the future," Theriogenology 45:57-68 (1996).
Wang et al., "A subpopulation of precursor cells in the mouse dentate gyrus receives synaptic GABAergic input," Mol Cell Neurosci, 29:181-189, Jun. 2005, 9 pages.
Wang et al., "Clearance of amyloid-beta in Alzheimer's disease: progress, problems and perspectives," Drug Disc. Today, 11 (19-20):931-938, Oct. 2006, 9 pages.
Wang et al., "Functional soluble CD1 OO/Sema4D released from activated lymphocytes: possible role in normal and pathologic immune responses," Blood, 97(11):3498-3504, Jun. 2001, 7 pages.
Watanabe et al., "Enhanced Immune Responses in Transgenic Mice Expressing a Truncated Form of the Lymphocyte Semaphorin CD100," J Immunol, 167(8):4321-4328, Oct. 2001, 9 pages.
Waxman and Giasson, "Characterization of antibodies that selectively detect a-synuclein in pathological inclusions," Acta Neuropathol, 116(1):37-46, Jul. 2008, 17 pages.
Webster et al., "Antibody-mediated phagocytosis of the amyloid β-peptide in microglia is differentially modulated by C1q," The Journal of Immunology, 2001, 166(12):7496-7503.
Weksler et al., "Patients with Alzheimer disease have lower levels of serum anti-amyloid peptide antibodies than healthy elderly individuals," Experimental Gerontology, 37:43-948, 2002, 8 pages.
Wilcock et al., "Amyloid-β vaccination, but Not Nitro-Nonsteroidal Anti-Inflammatory Drug Treatment, Increases Vascular Amyloid and Micro hemorrhage While Both Reduce Parenchymal Amyloid," Neuroscience 144:950-960, Feb. 2007, 11 pages.
Wilcock et al., "Intracranially Administered Anti-A13 Antibodies Reduce β-Amyloid Deposition by Mechanisms Both Independent of and Associated with Microglial Activation," J Neurosci, 23(9):3745-3751, May 2003, 7 pages.
Wilcock et al., "Passive immunotherapy against Aβ in aged APP= transgenic mice reverses cognitive deficits and depletes parenchymal amyloid deposits in spite of increased vascular amyloid and microhemorrhage," J Neuroinflammation, 1:24, Dec. 8, 2004, 11 pages.
Wilcock et al., "Quantification of cerebral amyloid angiopathy and parenchymal amyloid plaques with Congo red histochemical stain," Nat Protoc 1(3):1591-1595, 2006, 5 pages.
Wittnam et al., "Pyroglutamate amyloid β (Aβ) aggravates behavioral deficits in transgenic amyloid mouse model for Alzheimer disease," J Biol Chem, 287(11):8154-8162, Mar. 9, 2012, 15 pages.
Woulfe et al., "Absence of elevated anti-a-synuclein and anti-EBV latent membrane protein antibodies in PD," Neurology, 58: 1435-1436, May 2002, 4 pages.
Wu et al., "Humanization of a Murine Monoclonal Antibody by Simultaneous Optimization of Framework and CDR Residues," J Mol Biol 294:151-162, 1999, 12 pages.
Zago et al., "Vascular alterations in PDAPP mice after anti-Aβ immunotherapy: Implications for amyloid-related imaging abnormalities," Alzheimer's & Dementia, 2013, 9(5):S105-S115.
Zhang et al., "Semi-quantitative analysis of a-synuclein in subcellular pools of rat brain neurons: An immunogold electron microscopic study using a C-terminal specific monoclonal antibody," Brain Res, 1244:40-52, 2008, 13 pages.
Zhao et al., "Distinct Morphological Stages of Dentate Granule Neuron Maturation in the Adult Mouse Hippocampus," J Neurosci. 26(1):3-11, Society for Neuroscience, Jan. 2006, 9 pages.
Zlokovic "The Blood-Brain Barrier in Health and Chronic Neurodegenerative Disorders," Neuron 57: 178-201, 2008, 24 pages.
"Biogen plans regulatory filing for aducanumab in Alzheimer's disease based on new analysis of larger dataset from phase 3 studies", Biogen News Release, Oct. 22, 2019, 12 pages.
"Biogen and Eisai to discontinue phase 3 engage and emerge trials of aducanumab in Alzheimer's disease", Biogen News Release, Mar. 21, 2019, 8 pages.
"Biogen Idec Presents Positive Interim Results from Phase 1B Study of Investigational Alzheimer's Disease Treatment Aducanumab", European Pharmaceutical Review, 6 pages.
"Biogen Presents New Data from Phase 1B Study of Investigational Alzheimer's Disease Treatment Aducanumab (BIIB037) at Alzheimer's Association International Conference", FierceBiotech, 2015, 6 pages.
Arrighi et al., "Amyloid-related imaging abnormalities-haemosiderin (ARIA-H) in patients with Alzheimer's disease treated with bapineuzumab: a historical, prospective secondary analysis", Journal of Neurosurg Psychiatry, 2016, 7 pages.
Atwood et al., "A unified Hypothesis of Early- and Late-Onset Alzheimer's Disease Pathogenesis", Journal of Alzheimer's Disease, 2015, 47:33-47.

(56) References Cited

OTHER PUBLICATIONS

Barakos et al., "MR Imaging Features of Amyloid-Related Imaging Abnormalities", Am. J. Neuroradiol., 2013, 34:1958-65.

BusinessWire [online], "Biogen Idec Presents Positive Interim Results from Phase 1B Study of Investigational Alzheimer's Disease Treatment Aducanumab (BIIB037) at 2015 AD/PD Conference", published on Mar. 20, 2015, [retrieved on Jan. 11, 2021], retrieved from URL<www.businesswire.com/news/home/20150320005170/en/Biogen-Idec-Presents-Positive-Interim-Results-Phase#.VS5GktysXE1>, 4 pages.

Gleason et al., "Unblinded by the light: amyloid-related imaging abnormalities in Alzheimer's clinical trials", Eur. Acad. Neurol., 2020, 1 pages.

Henstridge et al., "Beyond the neuron-cellular interactions early in Alzheimer disease pathogenesis", Nat. Rev. Neurosci., 2019, 20:94-107.

Sperling et al., "Amyloid related abnormalities in patients with Alzheimer's disease treated with bapineuzumab: a retrospective analysis", The Lancet Neurology, 2012, 11(3):241-249.

Sperling et al., "Amyloid related imaging abnormalities (ARIA) in amyloid modifying therapeutic trials: recommendations from the Alzheimer's association research roundtable workgroup", Alzheimer's & Dementia, Jul. 2011, 7(4):367-385.

Swerdlow, Russell, "Pathogenesis of Alzheimer's Disease", Clin. Interv. Ageing, 2007, 2:347-359.

\* cited by examiner

```
                        SEQUENCE LISTING

<160> NUMBER OF SEQ ID NOS: 12

<210> SEQ ID NO 1
<211> LENGTH: 5
<212> TYPE: PRT
<213> ORGANISM: Homo sapiens

<400> SEQUENCE: 1

Ser Tyr Gly Met His
1               5

<210> SEQ ID NO 2
<211> LENGTH: 17
<212> TYPE: PRT
<213> ORGANISM: Homo sapiens

<400> SEQUENCE: 2

Val Ile Trp Phe Asp Gly Thr Lys Lys Tyr Tyr Thr Asp Ser Val Lys
1               5                   10                  15

Gly

<210> SEQ ID NO 3
<211> LENGTH: 15
<212> TYPE: PRT
<213> ORGANISM: Homo sapiens

<400> SEQUENCE: 3

Asp Arg Gly Ile Gly Ala Arg Arg Gly Pro Tyr Tyr Met Asp Val
1               5                   10                  15

<210> SEQ ID NO 4
<211> LENGTH: 11
<212> TYPE: PRT
<213> ORGANISM: Homo sapiens

<400> SEQUENCE: 4

Arg Ala Ser Gln Ser Ile Ser Ser Tyr Leu Asn
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Homo sapiens

<400> SEQUENCE: 6

Gln Gln Ser Tyr Ser Thr Pro Leu Thr
1               5

<210> SEQ ID NO 7
<211> LENGTH: 124
<212> TYPE: PRT
<213> ORGANISM: Homo sapiens
```

-continued

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Arg Asp Arg Gly Ile Gly Ala Arg Arg Gly Pro Tyr Tyr Met Asp
            100                 105                 110

Val Trp Gly Lys Gly Thr Thr Val Thr Val Ser Ser
        115                 120

<210> SEQ ID NO 8
<211> LENGTH: 108
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105

<210> SEQ ID NO 9
<211> LENGTH: 453
<212> TYPE: PRT
<213> ORGANISM: Homo sapiens

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys 85                  90                  95
Ala Arg Asp Arg Gly Ile Gly Ala Arg Arg Gly Pro Tyr Tyr Met Asp
                100                 105                 110

Val Trp Gly Lys Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 10
<211> LENGTH: 214
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 11
<211> LENGTH: 40
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 12
<211> LENGTH: 42
<212> TYPE: PRT
<213> ORGANISM: Homo sapiens

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

PHARMACEUTICAL COMPOSITIONS CONTAINING ANTI-BETA AMYLOID ANTIBODIES

CROSS-REFERENCE TO RELATED APPLICATION

This application is the US National Stage of International Application No. PCT/US2018/047508, filed on Aug. 22, 2018, which claims the benefit of priority of U.S. Provisional Application No. 62/548,583, filed Aug. 22, 2017. The contents of each of these prior applications is incorporated by reference herein.

FIELD

The present application relates generally to pharmaceutical compositions comprising anti-beta amyloid (Aβ) antibodies and uses thereof.

BACKGROUND

Aβ is a peptide generated from the metabolism of amyloid precursor protein (APP). Several Aβ peptide alloforms exist (e.g., Aβ40 and Aβ42). These monomeric peptides have a variable tendency to aggregate into higher order dimers and oligomers. Through a process of fibrillogenesis, soluble oligomers may transition into insoluble deposits having a β pleated sheet structure. These deposits are also referred to as amyloid plaques and are composed of predominantly fibrillar amyloid (Hampel et al., *Exp Neurol.*, 223(2):334-46 (2010); Gregory and Halliday, *Neurotox Res.*, 7(1-2):29-41 (2005)). Both soluble and fibrillar forms of Aβ appear to contribute to disease process in disorders characterized by deposition of Aβ such as Alzheimer's disease (AD) (Meyer-Luehmann, *J Neurosci.*, 29(40):12636-40 (2009); Hock, *Dialogues Clin Neurosci.*, 5(1):27-33 (2003); Selkoe, *Cold Spring Harb Perspect Biol.*, 3(7). pii: a004457 (2011)).

AD patients having high serum titers of anti-Aβ antibodies that recognize amyloid plaques have slower rates of cognitive decline and disability as compared to patients that do not have anti-Aβ antibodies. Moreover, patients who develop high titers of anti-Aβ antibodies show reduced numbers of brain Aβ plaques and improved cognitive performance assessed after long-term follow up. These clinical data suggest that AD patients treated with anti-Aβ antibodies in a passive immunotherapy paradigm are likely to show reduced cognitive impairment, a lower density of brain Aβ deposits, and reduced rates of cognitive deterioration.

The anti-Aβ antibody, BIIB037, is a fully human antibody comprising a glycosylated human IgG1 heavy chain and a human kappa light chain. Recombinantly expressed BIIB037 binds with high apparent affinity to high molecular weight aggregates, presumably fibrils, of human Aβ. By immunohistochemistry, BIIB037 shows high affinity binding to Aβ plaques in human AD brain and in brain tissues derived from human APP-expressing transgenic mice. The affinity and specificity of BIIB037 for high molecular weight aggregates of human Aβ was confirmed by immunoprecipitation, immunoblotting, and immunohistochemistry. In Tg2576 AD transgenic mice, BIIB037 treatment results in measurable drug levels in brain as assessed by ELISA. Following administration of BIIB037 in Tg2576 mice, immunoreactivity for BIIB037 was observed in association with brain parenchymal and vascular amyloid deposits, suggesting that BIIB037 enters brain parenchyma and binds to its target. It is believed that systemically administered anti-Aβ antibodies such as BIIB037 enter the brain, bind to deposits of Aβ, and trigger their clearance from the brain by Fc receptor dependent mechanisms. Antibody-mediated removal of Aβ from the brain is hypothesized to decrease Aβ burden, thereby preventing neuronal dysfunction, slowing the progression of pathology and reducing the rate of cognitive decline in AD.

SUMMARY

This disclosure relates, in part, to pharmaceutical compositions containing anti-Aβ antibody or Aβ-binding fragments thereof and their use in the treatment of abnormal accumulation or deposition of Aβ in the central nervous system, mild cognitive impairment, and Aβ-associated disorders such as Alzheimer's disease.

In one aspect, the disclosure features a pharmaceutical composition comprising an anti-Aβ antibody or Aβ-binding fragment thereof and arginine hydrochloride (Arg.HCl).

In some embodiments, the anti-Aβ antibody or Aβ-binding fragment thereof comprises an immunoglobulin heavy chain variable domain (VH) and an immunoglobulin light chain variable domain (VL), the VH and VL comprising the CDRs of BIIB037. In some instances, the six CDRs of BIIB037 comprise or consist of the amino acid sequences set forth in SEQ ID NO:1; SEQ ID NO:2; SEQ ID NO:3; SEQ ID NO:4; SEQ ID NO:5; and SEQ ID NO:6.

In some embodiments, the composition comprises the anti-Aβ antibody or Aβ-binding fragment thereof at a concentration of 50 mg/ml to 250 mg/ml. In other embodiments, the composition comprises the anti-Aβ antibody or Aβ-binding fragment thereof at a concentration of 75 mg/ml to 165 mg/ml. In certain embodiments, the composition comprises the anti-Aβ antibody or Aβ-binding fragment thereof at a concentration of 150 mg/ml. In certain embodiments, the composition comprises the anti-Aβ antibody or Aβ-binding fragment thereof at a concentration of 100 mg/ml.

In some embodiments, the composition comprises Arg.HCl at a concentration of 50 mM to 250 mM. In other embodiments, the composition comprises Arg.HCl at a concentration of 75 mM to 175 mM. In certain embodiments, the composition comprises Arg.HCl at a concentration of 150 mM.

In some embodiments, the composition further comprises Polysorbate-80 (PS80). In some embodiments, the composition comprises PS80 at a concentration of 0.01% to 0.1%. In other embodiments, the composition comprises PS80 at a concentration of 0.03% to 0.08%. In certain embodiments, the composition comprises PS80 at a concentration of 0.05%.

In some embodiments, the composition further comprises a buffer selected from the group consisting of histidine, acetate, succinate, and citrate. In certain instances, the buffer is histidine. In certain instances, the buffer is acetate. In certain instances, the buffer is succinate. In certain instances, the buffer is citrate. In certain embodiments, the composition comprises histidine, acetate, succinate, or citrate at a concentration of 10 mM to 30 mM. In certain embodiments, the composition comprises histidine, acetate, succinate, or citrate at a concentration of 20 mM. In certain embodiments, the composition comprises histidine at a concentration of 10 mM to 30 mM. In certain embodiments, the composition comprises histidine at a concentration of 20 mM.

In some embodiments, the composition further comprises methionine. In some embodiments, the composition comprises methionine at a concentration of 0.01 mM to 150 mM. In some embodiments, the composition comprises methionine at a concentration of 0.01 mM to 125 mM. In some embodiments, the composition comprises methionine at a concentration of 0.01 mM to 100 mM. In some embodiments, the composition comprises methionine at a concentration of 0.01 mM to 75 mM. In some embodiments, the composition comprises methionine at a concentration of 0.01 mM to 50 mM. In some embodiments, the composition comprises methionine at a concentration of 0.01 mM to 20 mM. In other embodiments, the composition comprises methionine at a concentration of 5 mM to 15 mM. In other embodiments, the composition comprises methionine at a concentration of 5 mM to 50 mM. In other embodiments, the composition comprises methionine at a concentration of 5 mM to 75 mM. In other embodiments, the composition comprises methionine at a concentration of 5 mM to 100 mM. In other embodiments, the composition comprises methionine at a concentration of 5 mM to 125 mM. In other embodiments, the composition comprises methionine at a concentration of 5 mM to 150 mM. In certain embodiments, the composition comprises methionine at a concentration of 10 mM. In certain embodiments, the composition comprises methionine at a concentration of 50 mM. In certain embodiments, the composition comprises methionine at a concentration of 75 mM. In certain embodiments, the composition comprises methionine at a concentration of 100 mM. In certain embodiments, the composition comprises methionine at a concentration of 125 mM. In certain embodiments, the composition comprises methionine at a concentration of 150 mM.

In some embodiments, the composition further comprises sucrose. In some embodiments, the composition comprises sucrose at a concentration of 0.01% to 5%. In other embodiments, the composition comprises sucrose at a concentration of 1% to 4%. In certain embodiments, the composition comprises sucrose at a concentration of 3%.

In some embodiments, the composition has a pH of 5.2 to 6.2. In certain embodiments, the composition has a pH of 5.2 to 6.0. In certain embodiments, the composition has a pH of 5.3 to 5.7. In other embodiments, the composition has a pH of 5.5.

In certain embodiments, the pharmaceutical composition comprises the anti-Aβ antibody or the Aβ-binding fragment thereof at a concentration of 50 mg/ml to 250 mg/ml; Arg.HCl at a concentration of 50 mM to 200 mM; methionine at a concentration of 0 mM to 20 mM; histidine at a concentration of 10 mM to 30 mM; PS80 at a concentration of 0.01% to 0.1%; and sucrose at a concentration of 0 to 3%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5.

In certain embodiments, the pharmaceutical composition comprises the anti-Aβ antibody or the Aβ-binding fragment thereof at a concentration of 150 mg/ml; Arg.HCl at a concentration of 150 mM; methionine at a concentration of 10 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5.

In certain embodiments, the pharmaceutical composition comprises the anti-Aβ antibody or the Aβ-binding fragment thereof at a concentration of 100 mg/ml; Arg.HCl at a concentration of 150 mM; methionine at a concentration of 10 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5.

In some embodiments, the VH comprises or consists of a sequence at least 80% identical to SEQ ID NO:7 and the VL comprises or consists of a sequence at least 80% identical to SEQ ID NO:8. In some embodiments, the VH comprises or consists of a sequence at least 90% identical to SEQ ID NO:7 and the VL comprises or consists of a sequence at least 90% identical to SEQ ID NO:8. In some embodiments, the VH comprises or consists of the sequence of SEQ ID NO:7 and the VL comprises or consists of the sequence of SEQ ID NO:8.

In some embodiments, the anti-Aβ antibody comprises an immunoglobulin heavy chain and an immunoglobulin light chain. In certain instances, the heavy chain comprises or consists of a sequence at least 80% identical to SEQ ID NO:9 and the light chain comprises or consists of a sequence at least 80% identical to SEQ ID NO:10. In other instances, the heavy chain comprises or consists of a sequence at least 90% identical to SEQ ID NO:9 and the light chain comprises or consists of a sequence at least 90% identical to SEQ ID NO:10. In yet other instances, the heavy chain comprises or consists of the sequence of SEQ ID NO:9 and the light chain comprises or consists of the sequence of SEQ ID NO:10.

In another aspect, the disclosure features a method of treating abnormal accumulation or deposition of Aβ in the central nervous system in a human subject in need thereof. The method comprises administering to the human subject a pharmaceutical composition described herein.

In another aspect, the disclosure features a method of treating mild cognitive impairment in a human subject in need thereof. The method comprises administering to the human subject a pharmaceutical composition described herein.

In another aspect, the disclosure features a method of treating Alzheimer's disease in a human subject in need thereof. The method comprises administering to the human subject a pharmaceutical composition described herein.

In some embodiments, of these aspects, the pharmaceutical composition is administered subcutaneously to the human subject. In some embodiments, of these aspects, the pharmaceutical composition is administered intravenously to the human subject.

In another aspect, the disclosure provides a pharmaceutical composition comprising an anti-Aβ antibody or Aβ-binding fragment thereof, a thiol-containing antioxidant, and arginine hydrochloride (Arg.HCl).

In some embodiments, the anti-Aβ antibody or Aβ-binding fragment thereof comprises an immunoglobulin heavy chain variable domain (VH) and an immunoglobulin light chain variable domain (VL), the VH and VL comprising the CDRs of BIIB037. In some instances, the six CDRs of BIIB037 comprise or consist of the amino acid sequences set forth in SEQ ID NO:1; SEQ ID NO:2; SEQ ID NO:3; SEQ ID NO:4; SEQ ID NO:5; and SEQ ID NO:6.

In some embodiments, the composition comprises the anti-Aβ antibody or Aβ-binding fragment thereof at a concentration of 50 mg/ml to 250 mg/ml. In other embodiments, the composition comprises the anti-Aβ antibody or Aβ-binding fragment thereof at a concentration of 75 mg/ml to 165 mg/ml. In certain embodiments, the composition comprises the anti-Aβ antibody or Aβ-binding fragment thereof at a concentration of 150 mg/ml. In certain embodiments, the composition comprises the anti-Aβ antibody or Aβ-binding fragment thereof at a concentration of 100 mg/ml.

In some embodiments, the thiol-containing antioxidant in the composition is selected from the group consisting of GSH, GSSG, the combination of GSH and GSSG, cystine, cysteine, and the combination of cysteine and cystine. In certain instances, the thiol-containing antioxidant is GSH. In certain instances, the thiol-containing antioxidant is GSSG. In certain instances, the thiol-containing antioxidant is GSH and GSSG. In certain embodiments, the thiol-containing antioxidant is at a concentration of 0.02 mM to 4 mM. In certain embodiments, the thiol-containing antioxidant is at a concentration of 0.02 mM to 2 mM. In certain embodiments, the thiol-containing antioxidant is at a concentration of 0.2 mM. In certain embodiments, the thiol-containing antioxidant is at a concentration of 0.4 mM. In certain embodiments, the thiol-containing antioxidant is at a concentration of 1 mM. In certain embodiments, the thiol-containing antioxidant is at a concentration of 2 mM. In certain embodiments, the thiol-containing antioxidant is at a concentration of 4 mM. In certain instances, the thiol-containing antioxidant in the composition is GSH at a concentration of 0.4 mM and GSSG at a concentration of 0.2 mM. In certain instances, the thiol-containing antioxidant in the composition is GSH at a concentration of 4 mM and GSSG at a concentration of 2 mM. In certain instances, the thiol-containing antioxidant in the composition is GSH at a concentration of 2 mM and GSSG at a concentration of 1 mM. In certain instances, the thiol-containing antioxidant in the composition is cysteine at a concentration of 0.4 mM and cystine at a concentration of 0.2 mM.

In some embodiments, the composition comprises Arg.HCl at a concentration of 50 mM to 250 mM. In other embodiments, the composition comprises Arg.HCl at a concentration of 75 mM to 175 mM. In certain embodiments, the composition comprises Arg.HCl at a concentration of 150 mM.

In some embodiments, the composition further comprises Polysorbate-80 (PS80). In some embodiments, the composition comprises PS80 at a concentration of 0.01% to 0.1%. In other embodiments, the composition comprises PS80 at a concentration of 0.03% to 0.08%. In certain embodiments, the composition comprises PS80 at a concentration of 0.05%.

In some embodiments, the composition further comprises a buffer selected from the group consisting of histidine, acetate, succinate, and citrate. In certain instances, the buffer is histidine. In certain instances, the buffer is acetate. In certain instances, the buffer is succinate. In certain instances, the buffer is citrate. In certain embodiments, the composition comprises histidine, acetate, succinate, or citrate at a concentration of 10 mM to 30 mM. In certain embodiments, the composition comprises histidine, acetate, succinate, or citrate at a concentration of 20 mM. In certain embodiments, the composition comprises histidine at a concentration of 10 mM to 30 mM. In certain embodiments, the composition comprises histidine at a concentration of 20 mM.

In some embodiments, the composition further comprises sucrose. In some embodiments, the composition comprises sucrose at a concentration of 0.01% to 5%. In other embodiments, the composition comprises sucrose at a concentration of 1% to 4%. In certain embodiments, the composition comprises sucrose at a concentration of 3%.

In some embodiments, the composition further comprises methionine. In some embodiments, the composition comprises methionine at a concentration of 0.01 mM to 150 mM. In some embodiments, the composition comprises methionine at a concentration of 0.01 mM to 125 mM. In some embodiments, the composition comprises methionine at a concentration of 0.01 mM to 100 mM. In some embodiments, the composition comprises methionine at a concentration of 0.01 mM to 75 mM. In some embodiments, the composition comprises methionine at a concentration of 0.01 mM to 50 mM. In some embodiments, the composition comprises methionine at a concentration of 0.01 mM to 20 mM. In other embodiments, the composition comprises methionine at a concentration of 5 mM to 15 mM. In other embodiments, the composition comprises methionine at a concentration of 5 mM to 50 mM. In other embodiments, the composition comprises methionine at a concentration of 5 mM to 75 mM. In other embodiments, the composition comprises methionine at a concentration of 5 mM to 100 mM. In other embodiments, the composition comprises methionine at a concentration of 5 mM to 125 mM. In other embodiments, the composition comprises methionine at a concentration of 5 mM to 150 mM. In certain embodiments, the composition comprises methionine at a concentration of 10 mM. In certain embodiments, the composition comprises methionine at a concentration of 50 mM. In certain embodiments, the composition comprises methionine at a concentration of 75 mM. In certain embodiments, the composition comprises methionine at a concentration of 100 mM. In certain embodiments, the composition comprises methionine at a concentration of 125 mM. In certain embodiments, the composition comprises methionine at a concentration of 150 mM. In some embodiments, the composition has a pH of 5.2 to 6.2. In certain embodiments, the composition has a pH of 5.2 to 6.0. In certain embodiments, the composition has a pH of 5.3 to 5.7. In other embodiments, the composition has a pH of 5.5.

In certain embodiments, the pharmaceutical composition comprises the anti-Aβ antibody or the Aβ-binding fragment thereof at a concentration of 50 mg/ml to 250 mg/ml; a thiol-containing antioxidant at a concentration of 0.02 mM to 4 mM; Arg.HCl at a concentration of 50 mM to 200 mM; histidine at a concentration of 10 mM to 30 mM; PS80 at a concentration of 0.01% to 0.1%; and sucrose at a concentration of 0 to 3%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 150 mg/ml; Arg.HCl at a concentration of 150 mM; a thiol-containing antioxidant at a concentration of 0.02 mM to 4 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 100 mg/ml; Arg.HCl at a concentration of 150 mM; a thiol-containing antioxidant at a concentration of 0.02 mM to 4 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In some embodiments, the VH comprises or consists of a sequence at least 80% identical to SEQ ID NO:7 and the VL comprises or consists of a sequence at least 80% identical to SEQ ID NO:8. In some embodiments, the VH comprises or consists of a sequence at least 90% identical to SEQ ID NO:7 and the VL comprises or consists of a sequence at least 90% identical to SEQ ID NO:8. In some embodiments, the VH comprises or consists of the sequence of SEQ ID NO:7 and the VL comprises or consists of the sequence of SEQ ID NO:8.

In some embodiments, the anti-Aβ antibody comprises an immunoglobulin heavy chain and an immunoglobulin light chain. In certain instances, the heavy chain comprises or consists of a sequence at least 80% identical to SEQ ID NO:9 and the light chain comprises or consists of a sequence at least 80% identical to SEQ ID NO:10. In other instances, the heavy chain comprises or consists of a sequence at least 90% identical to SEQ ID NO:9 and the light chain comprises or consists of a sequence at least 90% identical to SEQ ID NO:10. In yet other instances, the heavy chain comprises or consists of the sequence of SEQ ID NO:9 and the light chain comprises or consists of the sequence of SEQ ID NO:10.

In another aspect, the disclosure provides a pharmaceutical composition comprising an anti-Aβ antibody or Aβ-binding fragment thereof, a thiol-containing antioxidant, methionine, and arginine hydrochloride (Arg.HCl).

In some embodiments, the anti-Aβ antibody or Aβ-binding fragment thereof comprises an immunoglobulin heavy chain variable domain (VH) and an immunoglobulin light chain variable domain (VL), the VH and VL comprising the CDRs of BIIB037. In some instances, the six CDRs of BIIB037 comprise or consist of the amino acid sequences set forth in SEQ ID NO:1; SEQ ID NO:2; SEQ ID NO:3; SEQ ID NO:4; SEQ ID NO:5; and SEQ ID NO:6.

In some embodiments, the composition comprises the anti-Aβ antibody or Aβ-binding fragment thereof at a concentration of 50 mg/ml to 250 mg/ml. In other embodiments, the composition comprises the anti-Aβ antibody or Aβ-binding fragment thereof at a concentration of 75 mg/ml to 165 mg/ml. In certain embodiments, the composition comprises the anti-Aβ antibody or Aβ-binding fragment thereof at a concentration of 150 mg/ml. In certain embodiments, the composition comprises the anti-Aβ antibody or Aβ-binding fragment thereof at a concentration of 100 mg/ml.

In some embodiments, the thiol-containing antioxidant in the composition is selected from the group consisting of GSH, GSSG, the combination of GSH and GSSG, cystine, cysteine, and the combination of cysteine and cystine. In certain instances, the thiol-containing antioxidant is GSH. In certain instances, the thiol-containing antioxidant is GSSG. In certain instances, the thiol-containing antioxidant is GSH and GSSG. In certain embodiments, the thiol-containing antioxidant is at a concentration of 0.02 mM to 4 mM. In certain embodiments, the thiol-containing antioxidant is at a concentration of 0.02 mM to 2 mM. In certain embodiments, the thiol-containing antioxidant is at a concentration of 0.2 mM. In certain embodiments, the thiol-containing antioxidant is at a concentration of 0.4 mM. In certain embodiments, the thiol-containing antioxidant is at a concentration of 1 mM. In certain embodiments, the thiol-containing antioxidant is at a concentration of 2 mM. In certain embodiments, the thiol-containing antioxidant is at a concentration of 4 mM. In certain instances, the thiol-containing antioxidant in the composition is GSH at a concentration of 0.4 mM and GSSG at a concentration of 0.2 mM. In certain instances, the thiol-containing antioxidant in the composition is GSH at a concentration of 4 mM and GSSG at a concentration of 2 mM. In certain instances, the thiol-containing antioxidant in the composition is GSH at a concentration of 2 mM and GSSG at a concentration of 1 mM. In certain instances, the thiol-containing antioxidant in the composition is cysteine at a concentration of 0.4 mM and cystine at a concentration of 0.2 mM.

In some embodiments, the composition comprises methionine at a concentration of 0.01 mM to 150 mM. In some embodiments, the composition comprises methionine at a concentration of 0.01 mM to 125 mM. In some embodiments, the composition comprises methionine at a concentration of 0.01 mM to 100 mM. In some embodiments, the composition comprises methionine at a concentration of 0.01 mM to 75 mM. In some embodiments, the composition comprises methionine at a concentration of 0.01 mM to 50 mM. In some embodiments, the composition comprises methionine at a concentration of 0.01 mM to 20 mM. In other embodiments, the composition comprises methionine at a concentration of 5 mM to 15 mM. In other embodiments, the composition comprises methionine at a concentration of 5 mM to 50 mM. In other embodiments, the composition comprises methionine at a concentration of 5 mM to 75 mM. In other embodiments, the composition comprises methionine at a concentration of 5 mM to 100 mM. In other embodiments, the composition comprises methionine at a concentration of 5 mM to 125 mM. In other embodiments, the composition comprises methionine at a concentration of 5 mM to 150 mM. In certain embodiments, the composition comprises methionine at a concentration of 10 mM. In certain embodiments, the composition comprises methionine at a concentration of 50 mM. In certain embodiments, the composition comprises methionine at a concentration of 75 mM. In certain embodiments, the composition comprises methionine at a concentration of 100 mM. In certain embodiments, the composition comprises methionine at a concentration of 125 mM. In certain embodiments, the composition comprises methionine at a concentration of 150 mM.

In some embodiments, the composition comprises Arg.HCl at a concentration of 50 mM to 250 mM. In other embodiments, the composition comprises Arg.HCl at a concentration of 75 mM to 175 mM. In certain embodiments, the composition comprises Arg.HCl at a concentration of 150 mM.

In some embodiments, the composition further comprises Polysorbate-80 (PS80). In some embodiments, the composition comprises PS80 at a concentration of 0.01% to 0.1%. In other embodiments, the composition comprises PS80 at a concentration of 0.03% to 0.08%. In certain embodiments, the composition comprises PS80 at a concentration of 0.05%.

In some embodiments, the composition further comprises a buffer selected from the group consisting of histidine, acetate, succinate, and citrate. In certain instances, the buffer is histidine. In certain instances, the buffer is acetate. In certain instances, the buffer is succinate. In certain instances, the buffer is citrate. In certain embodiments, the composition comprises histidine, acetate, succinate, or citrate at a concentration of 10 mM to 30 mM. In certain embodiments, the composition comprises histidine, acetate, succinate, or citrate at a concentration of 20 mM. In certain embodiments, the composition comprises histidine at a concentration of 10 mM to 30 mM. In certain embodiments, the composition comprises histidine at a concentration of 20 mM.

In some embodiments, the composition further comprises sucrose. In some embodiments, the composition comprises sucrose at a concentration of 0.01% to 5%. In other embodiments, the composition comprises sucrose at a concentration of 1% to 4%. In certain embodiments, the composition comprises sucrose at a concentration of 3%.

In some embodiments, the composition has a pH of 5.2 to 6.2. In certain embodiments, the composition has a pH of 5.2 to 6.0. In certain embodiments, the composition has a pH of 5.3 to 5.7. In other embodiments, the composition has a pH of 5.5.

In certain embodiments, the pharmaceutical composition comprises the anti-Aβ antibody or the Aβ-binding fragment thereof at a concentration of 50 mg/ml to 250 mg/ml; a thiol-containing antioxidant at a concentration of 0.02 mM to 4 mM; methionine at a concentration of 5 mM to 150 mM; Arg.HCl at a concentration of 50 mM to 200 mM; histidine at a concentration of 10 mM to 30 mM; PS80 at a concentration of 0.01% to 0.1%; and sucrose at a concentration of 0 to 3%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 150 mg/ml; Arg.HCl at a concentration of 150 mM; a thiol-containing antioxidant at a concentration of 0.02 mM to 4 mM; methionine at a concentration of 10 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 150 mg/ml; Arg.HCl at a concentration of 150 mM; a thiol-containing antioxidant at a concentration of 0.02 mM to 4 mM; methionine at a concentration of 150 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 100 mg/ml; Arg.HCl at a concentration of 150 mM; a thiol-containing antioxidant at a concentration of 0.02 mM to 4 mM; methionine at a concentration of 10 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In certain embodiments, the pharmaceutical composition comprises the anti-Aβ antibody or the Aβ-binding fragment thereof at a concentration of 100 mg/ml; Arg.HCl at a concentration of 150 mM; a thiol-containing antioxidant at a concentration of 0.02 mM to 4 mM; methionine at a concentration of 150 mM; histidine at a concentration of 20 mM; and PS80 at a concentration of 0.05%. In some cases, this composition has a pH of 5.2 to 6.2. In some cases, this composition has a pH of 5.2 to 6.0. In certain embodiments, the composition has a pH of 5.3 to 5.7. In other embodiments, the composition has a pH of 5.5. In some instances, the thiol-containing antioxidant is selected from the group consisting of GSH, GSSG, the combination of GSH and GSSG, cystine, cysteine, and the combination of cysteine and cystine. In some instances, the thiol-containing antioxidant is GSH. In some instances, the thiol-containing antioxidant is GSSG. In some instances, the thiol-containing antioxidant is the combination of GSH and GSSG.

In some embodiments, the VH comprises or consists of a sequence at least 80% identical to SEQ ID NO:7 and the VL comprises or consists of a sequence at least 80% identical to SEQ ID NO:8. In some embodiments, the VH comprises or consists of a sequence at least 90% identical to SEQ ID NO:7 and the VL comprises or consists of a sequence at least 90% identical to SEQ ID NO:8. In some embodiments, the VH comprises or consists of the sequence of SEQ ID NO:7 and the VL comprises or consists of the sequence of SEQ ID NO:8.

In some embodiments, the anti-Aβ antibody comprises an immunoglobulin heavy chain and an immunoglobulin light chain. In certain instances, the heavy chain comprises or consists of a sequence at least 80% identical to SEQ ID NO:9 and the light chain comprises or consists of a sequence at least 80% identical to SEQ ID NO:10. In other instances, the heavy chain comprises or consists of a sequence at least 90% identical to SEQ ID NO:9 and the light chain comprises or consists of a sequence at least 90% identical to SEQ ID NO:10. In yet other instances, the heavy chain comprises or consists of the sequence of SEQ ID NO:9 and the light chain comprises or consists of the sequence of SEQ ID NO:10.

In another aspect, the disclosure features a method of treating abnormal accumulation or deposition of Aβ in the central nervous system in a human subject in need thereof. The method comprises administering to the human subject a pharmaceutical composition described herein.

In another aspect, the disclosure features a method of treating mild cognitive impairment in a human subject in need thereof. The method comprises administering to the human subject a pharmaceutical composition described herein.

In another aspect, the disclosure features a method of treating Alzheimer's disease in a human subject in need thereof. The method comprises administering to the human subject a pharmaceutical composition described herein.

In some embodiments, of these aspects, the pharmaceutical composition is administered subcutaneously to the human subject. In some embodiments, of these aspects, the pharmaceutical composition is administered intravenously to the human subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DETAILED DESCRIPTION

Figure 1:
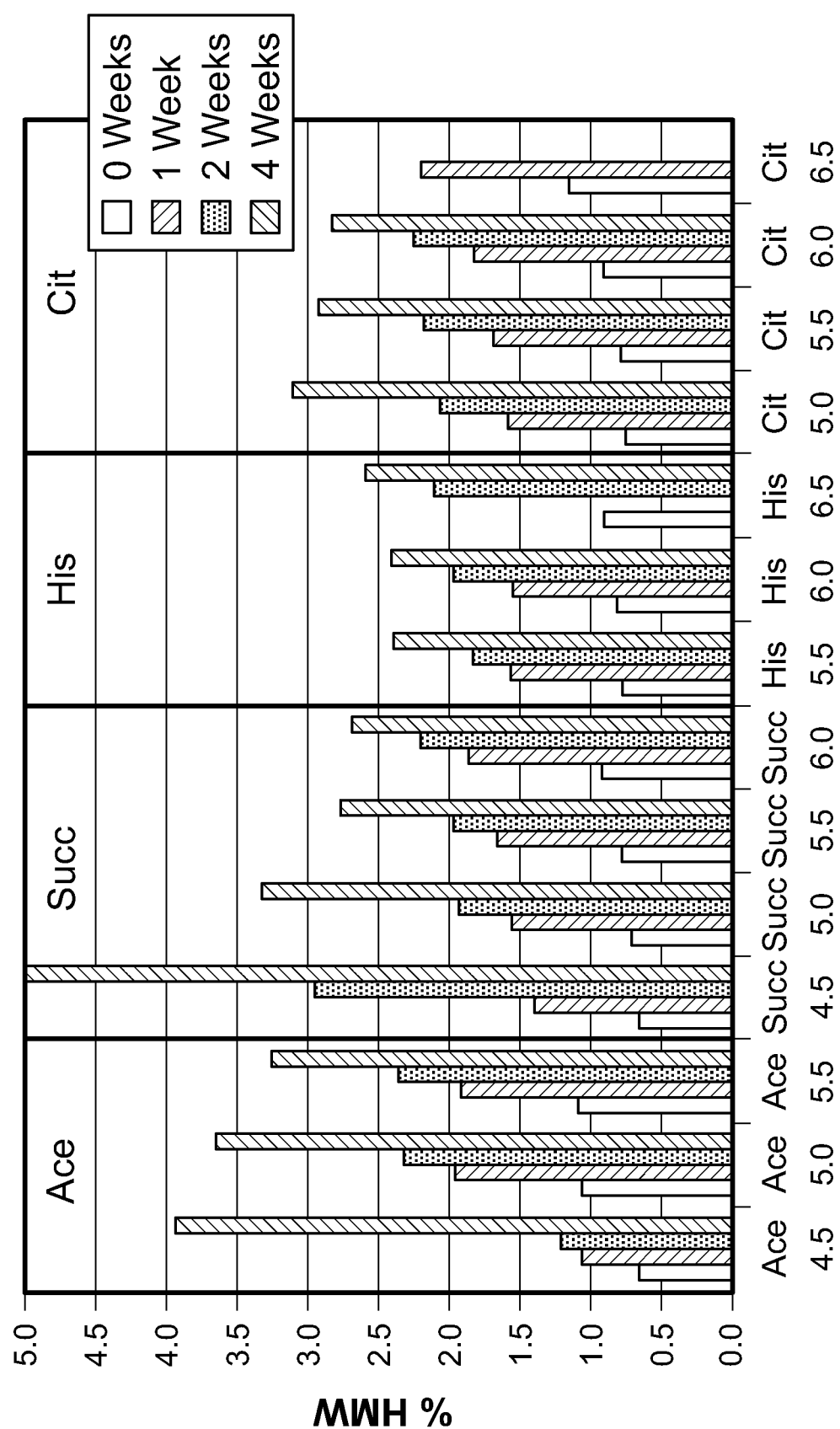
FIG. 1 is a bar graph depicting the % HMW for the indicated formulations stored at 40° C. over 4 weeks.

This application provides pharmaceutical compositions containing anti-Aβ antibodies and Aβ-binding fragments thereof and their use in the treatment of abnormal accumulation or deposition of Aβ in the central nervous system, mild cognitive impairment, and Aβ-associated disorders (e.g., Alzheimer's disease).

Amyloid Beta (Aβ or Abeta)

The Aβ peptide is an important risk factor and has a central role in the onset and progression of Alzheimer's disease. Aβ is produced in normal individuals, but under some circumstances, this molecule aggregates leading to disease progression.

Aβ denotes peptides of 36 to 43 amino acids that are involved in forming amyloid plaques found in the brains of patients with Alzheimer's disease. Similar plaques appear in some variants of Lewy body dementia and in inclusion body myositis. Aβ also forms the aggregates that coat cerebral blood vessels in cerebral amyloid angiopathy.

The Aβ peptides are formed by cleavage of the amyloid precursor protein (APP) by the enzymes beta secretase and gamma secretase. Aβ molecules can aggregate to form flexible soluble oligomers which may exist in several forms. Several Aβ peptide alloforms exist, Aβ40 and Aβ42. The amino acid sequence of human Amyloid β Peptide (1-40) is provided below:

```
                                              (SEQ ID NO: 11)
DAEFRHDSGYEVHHQKLVFFAEDVGSNKGAIIGLMVGGVV
```

The amino acid sequence of human Amyloid 13 Peptide (1-42) is provided below:

```
                                              (SEQ ID NO: 12)
DAEFRHDSGYEVHHQKLVFFAEDVGSNKGAIIGLMVGGVVIA
```

Soluble oligomeric forms of the Aβ peptide are thought to be causative agents in the development of Alzheimer's disease.

Anti-Aβ Antibodies

In some embodiments, the anti-Aβ antibody or Aβ-binding fragment thereof used in the compositions and methods described herein comprises the three heavy chain variable domain complementarity determining regions (CDRs) of an antibody referred to as "BIIB037" or as aducanumab. In some embodiments, the anti-Aβ antibody or Aβ-binding fragment thereof comprises the three light chain variable domain CDRs of BIIB037. In still other embodiments, the anti-Aβ antibody or Aβ-binding fragment thereof comprises the three heavy chain variable domain CDRs and the three light chain variable domain CDRs of BIIB037.

BIIB037 is a fully human antibody comprising a glycosylated human IgG1 heavy chain and a human kappa light chain. BIIB037 consists of the mature heavy chain amino acid sequence depicted in SEQ ID NO:9 and the mature light chain amino acid sequence depicted in SEQ ID NO:10.

The VH and VL of BIIB037 have amino acid sequences that are identical to the amino acid sequence of the VH and VL of antibody NI-101.12F6A described in U.S. Pat. No. 8,906,367 (see, Tables 2-4; incorporated by reference in its entirety herein). Specifically, antibody BIIB037 has an antigen binding domain comprising VH and VL variable regions depicted in Table 1 (VH) and Table 2 (VL), corresponding complementarity determining regions (CDRs) depicted in Table 3, and heavy and light chains depicted in Table 4 (H) and Table 5 (L).

TABLE 1

Amino acid sequences of the V$_H$ region of
anti-Aβ antibody BIIB037
(VH CDRs (Kabat definition) underlined).

Variable heavy chain sequence

QVQLVESGGG VVQPGRSLRL SCAASGFAFS SYGMHWVRQA

PGKGLEWVAV IWFDGTKKYY TDSVKGRFTI SRDNSKNTLY

LQMNTLRAED TAVYYCARDR GIGARRGPYY MDVWGKGTTV

TVSS (SEQ ID NO: 7)

TABLE 2

Amino acid sequences of the V$_L$ region of
anti-Aβ antibody BIIB037
(VL CDRs (Kabat definition) underlined).

Variable light chain sequence (kappa or lambda)

DIQMTQSPSS LSASVGDRVT ITCRASQSIS SYLNWYQQKP

GKAPKLLIYA ASSLQSGVPS RFSGSGSGTD FTLTISSLQP

EDFATYYCQQ SYSTPLTFGG GTKVEIKR (SEQ ID NO: 8)

TABLE 3

Denomination of CDR protein sequences in
Kabat Nomenclature of V$_H$ and V$_L$ regions of
anti-Aβ antibody BIIB037.

| CDR | Variable heavy chain | Variable light chain |
|---|---|---|
| CDR1 | SYGMH (SEQ ID NO: 1) | RASQSISSYLN (SEQ ID NO: 4) |
| CDR2 | VIWFDGTKKYYTDSVKG (SEQ ID NO: 2) | AASSLQS (SEQ ID NO: 5) |
| CDR3 | DRGIGARRGPYYMDV (SEQ ID NO: 3) | QQSYSTPLT (SEQ ID NO: 6) |

The amino acid sequence of the mature heavy chain of BIIB037 is provided in Table 4 below.

TABLE 4

Amino acid sequences of the heavy chain of
anti-Aβ antibody BIIB037
(heavy chain CDRs (Kabat definition) underlined).

Heavy chain sequence

QVQLVESGGG VVQPGRSLRL SCAASGFAFS SYGMHWVRQA

PGKGLEWVAV IWFDGTKKYY TDSVKGRFTI SRDNSKNTLY

LQMNTLRAED TAVYYCARDR GIGARRGPYY MDVWGKGTTV

TVSSASTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK RVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SREEMTKNQV SLTCLVKGFY PSDIAVEWES NGQPENNYKT

TPPVLDSDGS FFLYSKLTVD KSRWQQGNVF SCSVMHEALH

NHYTQKSLSL SPG (SEQ ID NO: 9)

The amino acid sequence of the mature light chain of BIIB037 is provided in Table 5 below.

TABLE 5

Amino acid sequences of the light chain of
anti-Aβ antibody BIIB037
(light chain CDRs (Kabat definition) underlined).

Light chain sequence

DIQMTQSPSS LSASVGDRVT ITCRASQSIS SYLNWYQQKP

GKAPKLLIYA ASSLQSGVPS RFSGSGSGTD FTLTISSLQP

EDFATYYCQQ SYSTPLTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC (SEQ ID NO: 10)

In some aspects, the anti-Aβ antibody or Aβ-binding fragment thereof comprises of a VH CDR1 comprising or consisting of the amino acid sequence set forth in SEQ ID NO.:1, a VH CDR2 comprising or consisting of the amino acid sequence set forth in SEQ ID NO.:2; and a VH CDR3 comprising or consisting of the amino acid sequence set forth in SEQ ID NO.:3. In some embodiments, the anti-Aβ antibody or Aβ-binding fragment thereof comprises a VL CDR1 comprising or consisting of the amino acid sequence set forth in SEQ ID NO.:4, a VL CDR2 comprising or consisting of the amino acid sequence set forth in SEQ ID NO.:5; and a VL CDR3 comprising or consisting of the amino acid sequence set forth in SEQ ID NO.:6.

In certain aspects, the anti-Aβ antibody or Aβ-binding fragment thereof comprises the CDRs comprising or consisting of the amino acid sequences set forth in SEQ ID NOs.:1 to 6.

In certain embodiments, the anti-Aβ antibody or Aβ-binding fragment thereof comprises a VH comprising or consisting of the amino acid sequence set forth in SEQ ID NO:7. In some embodiments, the anti-Aβ antibody or Aβ-binding fragment thereof selectively binds to a peptide comprising or consisting of amino acids 1-16 of human Aβ and comprises a VH domain that is at least 70%, 75%, 80%, 85%, 90%, 91%, 92%, 93%, 94%, 95%, 96%, 97%, 98%, 99% or more identical to the amino acid sequence of the VH domain of BIIB037 (SEQ ID NO:7), or differs at least at 1 to 5 amino acid residues, but at fewer than 40, 30, 20, 15, or 10, residues, from SEQ ID NO:7. In some embodiments, these anti-Aβ antibody or Aβ-binding fragments thereof selectively binds to a peptide comprising or consisting of amino acids 3-6 of human Aβ.

In certain embodiments, the anti-Aβ antibody or Aβ-binding fragment thereof comprises a VL comprising or consisting of the amino acid sequence set forth in SEQ ID NO:8. In some embodiments, the anti-Aβ antibody or Aβ-binding fragment thereof selectively binds to a peptide comprising or consisting of amino acids 1-16 of human Aβ and comprises a VL domain that is at least 70%, 75%, 80%, 85%, 90%, 91%, 92%, 93%, 94%, 95%, 96%, 97%, 98%, 99% or more identical to the amino acid sequence of the VL domain of BIIB037 (SEQ ID NO:8), or differs at least at 1 to 5 amino acid residues, but at fewer than 40, 30, 20, 15, or 10, residues, from SEQ ID NO:8. In some embodiments, these anti-Aβ antibody or Aβ-binding fragments thereof selectively binds to a peptide comprising or consisting of amino acids 3-6 of human Aβ.

In some embodiments, the anti-Aβ antibody or Aβ-binding fragment thereof comprises a VH having the amino acid sequence set forth in SEQ ID NO:7 and a VL having the amino acid sequence set forth in SEQ ID NO:8. In some embodiments, the anti-Aβ antibody or Aβ-binding fragment thereof selectively binds to a peptide comprising or consisting of amino acids 1-16 of human Aβ and comprises (i) a VH domain that is at least 70%, 75%, 80%, 85%, 90%, 91%, 92%, 93%, 94%, 95%, 96%, 97%, 98%, 99% or more identical to the amino acid sequence of the VH domain of BIIB037 (SEQ ID NO:7), and (ii) a VL domain that is at least 70%, 75%, 80%, 85%, 90%, 91%, 92%, 93%, 94%, 95%, 96%, 97%, 98%, 99% or more identical to the amino acid sequence of the VL domain of BIIB037 (SEQ ID NO:8); or differs at least at 1 to 5 amino acid residues, but at fewer than 40, 30, 20, 15, or 10, residues, from SEQ ID NO:7 and/or SEQ ID NO:8. In some embodiments, these anti-Aβ antibody or Aβ-binding fragments thereof selectively binds to a peptide comprising or consisting of amino acids 3-6 of human Aβ.

In certain embodiments, the anti-Aβ antibody or Aβ-binding fragment thereof comprises a heavy chain (HC) having the amino acid sequence set forth in SEQ ID NO:9. In some embodiments, the anti-Aβ antibody or Aβ-binding fragment thereof selectively binds to a peptide comprising or consisting of amino acids 1-16 of human Aβ and comprises a HC that is at least 70%, 75%, 80%, 85%, 90%, 91%, 92%, 93%, 94%, 95%, 96%, 97%, 98%, 99% or more identical to the amino acid sequence of SEQ ID NO:9, or differs at least at 1 to 5 amino acid residues, but at fewer than 40, 30, 20, 15, or 10, residues, from SEQ ID NO:9. In some embodiments, these anti-Aβ antibody or Aβ-binding fragments thereof selectively binds to a peptide comprising or consisting of amino acids 3-6 of human Aβ.

In certain embodiments, the anti-Aβ antibody or Aβ-binding fragment thereof comprises a light chain (LC) having the amino acid sequence set forth in SEQ ID NO:10. In some embodiments, the anti-Aβ antibody or Aβ-binding fragment thereof selectively binds to a peptide comprising or consisting of amino acids 1-16 of human Aβ and comprises a LC that is at least 70%, 75%, 80%, 85%, 90%, 91%, 92%, 93%, 94%, 95%, 96%, 97%, 98%, 99% or more identical to the amino acid sequence of SEQ ID NO:10, or differs at least at 1 to 5 amino acid residues, but at fewer than 40, 30, 20, 15, or 10, residues, from SEQ ID NO:10. In some embodiments, these anti-Aβ antibody or Aβ-binding fragments thereof selectively binds to a peptide comprising or consisting of amino acids 3-6 of human Aft In certain embodiments, the anti-Aβ antibody or Aβ-binding fragment thereof comprises a HC having the amino acid sequence set forth in SEQ ID NO:9 and a LC having the amino acid sequence set forth in SEQ ID NO:10. In some embodiments, the anti-Aβ antibody or Aβ-binding fragment thereof selectively binds to a peptide comprising or consisting of amino acids 1-16 of human Aβ and comprises (i) a HC that is at least 70%, 75%, 80%, 85%, 90%, 91%, 92%, 93%, 94%, 95%, 96%, 97%, 98%, 99% or more identical to the amino acid sequence of SEQ ID NO:9, or differs at least at 1 to 5 amino acid residues, but at fewer than 40, 30, 20, 15, or 10, residues, from SEQ ID NO:9; and (ii) a LC that is at least 70%, 75%, 80%, 85%, 90%, 91%, 92%, 93%, 94%, 95%, 96%, 97%, 98%, 99% or more identical to the amino acid sequence of SEQ ID NO:10, or differs at least at 1 to 5 amino acid residues, but at fewer than 40, 30, 20, 15, or 10, residues, from SEQ ID NO:10. In some embodiments, these anti-Aβ antibody or Aβ-binding fragments thereof selectively binds to a peptide comprising or consisting of amino acids 3-6 of human Aβ.

In certain embodiments, the anti-Aβ antibody is an IgG antibody. In specific embodiments, the anti-Aβ antibody has heavy chain constant region chosen from, e.g., IgG1, IgG2, IgG3, IgG4, IgM, IgA1, IgA2, IgD, and IgE. In one embodiment, the anti-Aβ antibody is of the human IgG1 isotype. In another embodiment, the anti-Aβ antibody is of the human IgG2 isotype. In yet another embodiment, the anti-Aβ antibody is of the human IgG3 isotype. In yet another embodiment, the anti-Aβ antibody is of the human IgG4 isotype. In further embodiments, the antibody has a light chain constant region chosen from, e.g., a human kappa or human lambda light chain. In a certain embodiment, the anti-Aβ antibody is a human IgG1/human kappa antibody. In some cases, the heavy chain constant region is human or a modified form of a human constant region. In certain instances the human constant region may include at least 1 and up to 2, 3, 4, 5, 6, 7, 8, 9, 10, 11, 12, 13, 14, 15, 16, 17, 18, 19, or 20 substitutions. In a particular embodiment, the modified human Fc region is a modified human IgG1 Fc region. In some cases, the constant region of an anti-Aβ antibody is modified by mutation of one or more amino acid residues to impart a desired functional property (e.g., altered effector function or half-life, reduced glycosylation). For example, the N-linked glycosylation site may be substituted to prevent or reduce N-linked glycosylation of Fc region (e.g., human IgG1 Fc region).

In some embodiments, the anti-Aβ antibody is a full-length (whole) antibody or substantially full-length. The protein can include at least one, and preferably two, complete heavy chains, and at least one, and preferably two, complete light chains. In some embodiments, the anti-Aβ antibody is a Aβ-binding fragment. In some instances, the Aβ-binding fragment is a Fab, a Fab', an F(ab')2, a Facb, an Fv, a single chain Fv (scFv), a sc(Fv)2, or a diabody.

Antibodies, such as BIIB037, or Aβ-binding fragments thereof can be made, for example, by preparing and expressing synthetic genes that encode the recited amino acid sequences or by mutating human germline genes to provide a gene that encodes the recited amino acid sequences. Moreover, this antibody and other anti-Aβ antibodies can be produced, e.g., using one or more of the following methods.
Methods of Producing Antibodies Anti-Aβ antibodies or Aβ-binding fragments may be produced in bacterial or eukaryotic cells. Some antibodies, e.g., Fab's, can be produced in bacterial cells, e.g., *E. coli* cells. Antibodies can also be produced in eukaryotic cells such as transformed cell lines (e.g., CHO, 293E, COS). In addition, antibodies (e.g., scFv's) can be expressed in a yeast cell such as *Pichia* (see, e.g., Powers et al., *J Immunol Methods*. 251:123-35 (2001)), *Hanseula*, or *Saccharomyces*. To produce the antibody of interest, a polynucleotide encoding the antibody is constructed, introduced into an expression vector, and then expressed in suitable host cells. Polynucleotides encoding an anti-Aβ antibody comprising the VH and/or VL, HC and/or LC of the Aβ antibodies described herein would be readily envisioned by the ordinarily skilled artisan. Standard molecular biology techniques are used to prepare the recombinant expression vector, transfect the host cells, select for transformants, culture the host cells and recover the antibody.

If the anti-Aβ antibodies or Aβ-binding fragments is to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341:544-546 (1989), araB promoter (Better et al., *Science*, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., *J. Bacteriol.*, 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, and NIH3T3 cells, the expression vector includes a promoter necessary for expression in these cells, for example, an SV40 promoter (Mulligan et al., *Nature*, 277:108 (1979)), MMLV-LTR promoter, EF1α promoter (Mizushima et al., *Nucleic Acids Res.*, 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, antibodies are produced in mammalian cells. Exemplary mammalian host cells for expressing an antibody include Chinese Hamster Ovary (CHO cells) (including dhfr CHO cells, described in Urlaub and Chasin (1980) *Proc. Natl. Acad. Sci. USA* 77:4216-4220, used with a DHFR selectable marker, e.g., as described in Kaufman and Sharp (1982)*Mol. Biol.* 159:601-621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

In an exemplary system for antibody expression, a recombinant expression vector encoding both the antibody heavy chain and the antibody light chain of an anti-Aβ antibody (e.g., BIIB037) is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and the antibody is recovered from the culture medium.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. Animals are also provided comprising one or more of the nucleic acids described herein.

The antibodies of the present disclosure can be isolated from inside or outside (such as medium) of the host cell and purified as substantially pure and homogenous antibodies. Methods for isolation and purification commonly used for antibody purification may be used for the isolation and purification of antibodies, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

Anti-Aβ Antibody Compositions

This disclosure also provides compositions (e.g., pharmaceutical compositions) comprising the anti-Aβ antibodies or Aβ-binding fragments thereof described herein. For example, the anti-Aβ antibody compositions comprises an anti-Aβ antibody or Aβ-binding fragment thereof comprising an immunoglobulin heavy chain variable domain (VH) and an immunoglobulin light chain variable domain (VL), wherein the VH comprises the H-CDRs and the VL comprises the L-CDRs of BIIB037. In certain instances, the heavy chain CDRs (H-CDRs) comprise or consist of the amino acid sequences set forth in SEQ ID NO:1, SEQ ID NO:2, and SEQ ID NO:3; and the light chain CDRs (L-CDRs) comprise or consist of the amino acid sequences set forth in SEQ ID NO:4, SEQ ID NO:5, and SEQ ID NO:6. In some embodiments, the anti-Aβ antibody compositions comprises an anti-Aβ antibody or Aβ-binding fragment thereof comprising (i) a VH comprising or consisting of an amino acid sequence that is at least 85%, 90%, 91%, 92%, 93%, 94%, 95%, 96%, 97%, 98%, 99%, or 100% identical to the amino acid sequence set forth in SEQ ID NO:7; and (ii) a VL comprising or consisting of an amino acid sequence that is at least 85%, 90%, 91%, 92%, 93%, 94%, 95%, 96%, 97%, 98%, 99%, or 100% identical to the amino acid sequence set forth in SEQ ID NO:8. In certain embodiments, the anti-Aβ antibody compositions comprises an anti-Aβ antibody comprising (i) a heavy chain comprising or consisting of an amino acid sequence that is at least 85%, 90%, 91%, 92%, 93%, 94%, 95%, 96%, 97%, 98%, 99%, or 100% identical to the amino acid sequence set forth in SEQ ID NO:9; and (ii) a light chain comprising or consisting of an amino acid sequence that is at least 85%, 90%, 91%, 92%, 93%, 94%, 95%, 96%, 97%, 98%, 99%, or 100% identical to the amino acid sequence set forth in SEQ ID NO:10. In some embodiments, the anti-Aβ antibodies selectively bind to a peptide comprising or consisting of amino acids 1-16 of human Aβ. In some embodiments, the anti-Aβ antibodies selectively bind to a peptide comprising or consisting of amino acids 3-6 of human Aβ.

In certain embodiments, these compositions are high concentration anti-Aβ antibody compositions. By "high concentration anti-Aβ antibody composition" is meant a composition comprising anti-Aβ antibodies or Aβ-binding fragments thereof at a concentration of greater than 50 mg/ml and less than 300 mg/ml. In certain instances, the anti-Aβ antibody composition comprises anti-Aβ antibodies or Aβ-binding fragments thereof at a concentration of 50 mg/ml to 250 mg/ml. In certain instances, the anti-Aβ antibody composition comprises anti-Aβ antibodies or Aβ-binding fragments thereof at a concentration of 50 mg/ml to 225 mg/ml. In other instances, the anti-Aβ antibody composition comprises anti-Aβ antibodies or Aβ-binding fragments thereof at a concentration of 75 mg/ml to 225 mg/ml. In other instances, the anti-Aβ antibody composition comprises anti-Aβ antibodies or Aβ-binding fragments thereof at a concentration of 75 mg/ml to 165 mg/ml. In other instances, the anti-Aβ antibody composition comprises anti-Aβ antibodies or Aβ-binding fragments thereof at a concentration of 100 mg/ml to 225 mg/ml. In yet other instances, the anti-Aβ antibody composition comprises anti-Aβ antibodies or Aβ-binding fragments thereof at a concentration of 125 mg/ml to 225 mg/ml. In other instances, the anti-Aβ antibody composition comprises anti-Aβ antibodies or Aβ-binding fragments thereof at a concentration of 125 mg/ml to 175 mg/ml. In certain instances, the anti-Aβ antibody composition comprises anti-Aβ antibodies or Aβ-binding fragments thereof at a concentration of 240 mg/ml. In certain instances, the anti-Aβ antibody composition comprises anti-Aβ antibodies or Aβ-binding fragments thereof at a concentration of 225 mg/ml. In certain instances, the anti-Aβ antibody composition comprises anti-Aβ antibodies or Aβ-binding fragments thereof at a concentration of 200 mg/ml. In certain instances, the anti-Aβ antibody composition comprises anti-Aβ antibodies or Aβ-binding fragments thereof at a concentration of 175 mg/ml. In certain instances, the anti-Aβ antibody composition comprises anti-Aβ antibodies or Aβ-binding fragments thereof at a concentration of 150 mg/ml. In other instances, the anti-Aβ antibody composition comprises anti-Aβ antibodies or Aβ-binding fragments thereof at a concentration of 125 mg/ml. In some instances, the anti-Mantibody composition comprises anti-Aβ antibodies or Aβ-binding fragments thereof at a concentration of 100 mg/ml.

A composition (e.g., a pharmaceutical composition) comprising an anti-Aβ antibody or Aβ-binding fragment thereof described herein may be in any one of a variety of forms. These include, for example, liquid solutions (e.g., injectable and infusible solutions), dispersions, or suspensions. The preferred form can depend on the intended mode of administration and therapeutic application. In certain embodiments, a pharmaceutical composition described herein is in the form of a sterile injectable or infusible solution.

Sterile injectable solutions can be prepared by incorporating an antibody described herein in the required amount with one or a combination of ingredients, followed by filtered sterilization. Generally, dispersions are prepared by incorporating an antibody described herein into a sterile vehicle that contains a basic dispersion medium and the required other ingredients. In the case of sterile powders for the preparation of sterile injectable solutions, an exemplary method of preparation is vacuum drying and freeze drying that yields a powder of an antibody described herein plus any additional desired ingredient from a previously sterile-filtered solution thereof. The proper fluidity of a solution can be maintained, for example, by the use of a coating such as lecithin, by the maintenance of the required particle size in the case of dispersion, and by the use of surfactants.

The anti-Aβ antibody compositions (e.g., pharmaceutical compositions) may additionally comprise one or more excipients.

In one embodiment, the excipient lowers/reduces the aggregation and/or viscosity of the antibody in the composition compared to aggregation and/or viscosity of the antibody in the pharmaceutical composition without that excipient. In certain embodiments, such an excipient is arginine. In one instance, the excipient is L-arginine hydrochloride. Arginine (e.g., L-arginine hydrochloride) can be included in the composition at a concentration of 40 mM to 260 mM, 50 mM to 250 mM, 50 mM to 200 mM, 50 mM to 150 mM, 50 mM to 125 mM, 50 mM to 100 mM, 75 mM to 250 mM, 75 mM to 200 mM, 75 mM to 150 mM, or 75 mM to 100 mM. In certain embodiments arginine (e.g., Arg.HCl) is present in the composition at a concentration of 50 mM to 250 mM. In other embodiments, arginine (e.g., Arg.HCl) is present in the composition at a concentration of 50 mM to 200 mM. In certain instances, arginine (e.g., arginine hydrochloride) can be included in the composition at a concentration of 80 mM, 100 mM, 120 mM, 125 mM, 130 mM, 135 mM, 140 mM, 145 mM, 150 mM, 220 mM, or 260 mM. In a specific instance, arginine (e.g., arginine hydrochloride) can be included in the composition at a concentration of 100 mM. In another specific instance, arginine (e.g., arginine hydrochloride) can be included in the composition at a concentration of 150 mM.

Sometimes, solutions containing arginine develop visible particles after incubation at room temperature or higher temperatures (e.g., 40° C.). Addition of sucrose can reduce or prevent the formation of visible particles. Furthermore, sucrose can lower the counts of sub visible particulates. In some embodiments, the anti-Aβ antibody composition comprises sucrose at a concentration of 0.05% to 5%, 0.05% to 4%, 0.05% to 3%, 1% to 5%, 1% to 4%, 1% to 3%, 2% to 5%, 2% to 4%, or 2% to 3%. In certain embodiments, the anti-Aβ antibody composition comprises sucrose at a concentration of 0.5%, 1%, 1.5%, 2%, 2.5%, 3%, 3.5%, 4%, 4.5%, or 5%. In a particular embodiment, the anti-Aβ antibody composition comprises sucrose at a concentration of 3%. In another particular embodiment, the anti-Aβ antibody composition comprises sucrose at a concentration of 1%.

In one embodiment, the anti-Aβ antibody compositions comprise methionine. In one instance, methionine is included in the composition at a concentration from 0.5 mM to 150 mM. In another instance, methionine is included in the composition at a concentration from 0.5 mM to 25 mM. In yet another instance, methionine is included in the composition at a concentration from 5 mM to 150 mM. In one instance, methionine is included in the composition at a concentration of 5 mM, 10 mM, 15 mM, 20 mM or 25 mM, 50 mM, 75 mM, 100 mM, 125 mM, or 150 mM. In a particular instance, methionine is included in the composition at a concentration of 10 mM. In another particular instance, methionine is included in the composition at a concentration of 150 mM.

Antibody product manufacturing is a complex process that can involve several steps such as, e.g., drug substance and bulk formulation, filtration, shipping, pooling, filling, lyophilization, inspections, packaging, and storage. During these steps, antibodies may be subjected to many different forms of stresses, e.g., agitation, temperature, light exposure, and oxidation. These types of stresses can lead to denaturation and aggregation of the antibody, which compromise the product quality and can even lead to loss of a production batch. Agitation is one of the common physical stresses that antibody therapeutics are subjected to during the course of the manufacturing process. Agitation occurs, e.g., during mixing, ultrafiltration/diafiltration, pumping, shipping, and filling. To protect the antibody composition against agitation-induced stress, the composition may include a polysorbate. In certain embodiments, the composition comprises polysorbate-80 at a concentration of 0.01% to 0.5%, 0.01% to 0.1%, 0.01% to 0.09%, 0.01% to 0.08%, 0.01% to 0.07%, 0.01% to 0.06%, 0.01% to 0.05%, 0.01% to 0.04%, or 0.01% to 0.03%. In certain embodiments, the composition comprises polysorbate-80 at a concentration of 0.02% to 0.08%. In some embodiments, the composition comprises polysorbate-80 at a concentration of 0.01%, 0.02%, 0.03%, 0.04%, 0.05%, 0.06%, 0.07%, 0.08%, 0.09%, or 0.1%. In a particular embodiment, the composition comprises polysorbate-80 at a concentration of 0.05%.

Any antibody composition benefits from a buffer that provides good buffering capacity. In certain embodiments, the antibody composition comprises histidine as the buffering agent. In certain embodiments, the composition comprises histidine at a concentration of 5 mM to 50 mM, 5 mM to 40 mM, 5 mM to 35 mM, 5 mM to 30 mM, 5 mM to 25 mM, 10 mM to 50 mM, 10 mM to 40 mM, 10 mM to 30 mM, 10 mM to 25 mM, 15 mM to 50 mM, 15 mM to 40 mM, 15 mM to 30 mM, or 15 mM to 25 mM. In certain embodiments, the composition comprises histidine at a concentration of 5 mM to 35 mM. In certain embodiments, the composition comprises histidine at a concentration of 10 mM to 30 mM. In some embodiments, the composition comprises histidine at a concentration of 5 mM, 10 mM, 15 mM, 20 mM, 25 mM, 30 mM, or 35 mM. In a particular embodiment, the composition comprises histidine at a concentration of 20 mM. In certain embodiments, the antibody composition comprises acetate as the buffering agent. In certain embodiments, the composition comprises acetate at a concentration of 5 mM to 50 mM, 5 mM to 40 mM, 5 mM to 35 mM, 5 mM to 30 mM, 5 mM to 25 mM, 10 mM to 50 mM, 10 mM to 40 mM, 10 mM to 30 mM, 10 mM to 25 mM, 15 mM to 50 mM, 15 mM to 40 mM, 15 mM to 30 mM, or 15 mM to 25 mM. In certain embodiments, the composition comprises acetate at a concentration of 5 mM to 35 mM. In certain embodiments, the composition comprises acetate at a concentration of 10 mM to 30 mM. In some embodiments, the composition comprises acetate at a concentration of 5 mM, 10 mM, 15 mM, 20 mM, 25 mM, 30 mM, or 35 mM. In a particular embodiment, the composition comprises acetate at a concentration of 20 mM. In certain embodiments, the antibody composition comprises succinate as the buffering agent. In certain embodiments, the composition comprises succinate at a concentration of 5 mM to 50 mM, 5 mM to 40 mM, 5 mM to 35 mM, 5 mM to 30 mM, 5 mM to 25 mM, 10 mM to 50 mM, 10 mM to 40 mM, 10 mM to 30 mM, 10 mM to 25 mM, 15 mM to 50 mM, 15 mM to 40 mM, 15 mM to 30 mM, or 15 mM to 25 mM. In certain embodiments, the composition comprises succinate at a concentration of 5 mM to 35 mM. In certain embodiments, the composition comprises succinate at a concentration of 10 mM to 30 mM. In some embodiments, the composition comprises succinate at a concentration of 5 mM, 10 mM, 15 mM, 20 mM, 25 mM, 30 mM, or 35 mM. In a particular embodiment, the composition comprises succinate at a concentration of 20 mM. In certain embodiments, the antibody composition comprises citrate as the buffering agent. In certain embodiments, the composition comprises citrate at a concentration of 5 mM to 50 mM, 5 mM to 40 mM, 5 mM to 35 mM, 5 mM to 30 mM, 5 mM to 25 mM, 10 mM to 50 mM, 10 mM to 40 mM, 10 mM to 30 mM, 10 mM to 25 mM, 15 mM to 50 mM, 15 mM to 40 mM, 15 mM to 30 mM, or 15 mM to 25 mM. In certain embodiments, the composition comprises citrate at a concentration of 5 mM to 35 mM. In certain embodiments, the composition comprises citrate at a concentration of 10 mM to 30 mM. In some embodiments, the composition comprises citrate at a concentration of 5 mM, 10 mM, 15 mM, 20 mM, 25 mM, 30 mM, or 35 mM. In a particular embodiment, the composition comprises citrate at a concentration of 20 mM.

The pH of the antibody composition can be from 5.0 to 6.5. In certain cases, the pH of the antibody composition can be 5.2 to 6.2. In certain instances, the pH of the antibody composition is 5.0, 5.1, 5.2, 5.3, 5.4, 5.5, 5.6, 5.7, 5.8, 5.9, 6.0, 6.1, 6.2, 6.3, 6.4, or 6.5. In a particular embodiment, the pH of the antibody composition is 5.5.

In certain instances, the Aβ compositions comprise arginine (e.g., Arg. HCl). In other instances, the Aβ compositions comprise arginine (e.g., Arg. HCl) and methionine.

In certain embodiments, the Aβ compositions comprise L-arginine hydrochloride (e.g., 150 mM), methionine (e.g., 10 mM), histidine (e.g., 20 mM), and PS80 (e.g., 0.05%), and has a pH of 5.2 to 6.2. In some embodiments, the Aβ compositions comprise L-arginine hydrochloride (e.g., 150 mM), methionine (e.g., 10 mM, 150 mM), histidine (e.g., 20 mM), and PS80 (e.g., 0.05%), and has a pH of 5.5. In certain embodiments, the Aβ compositions comprise L-arginine hydrochloride (e.g., 150 mM), methionine (e.g., 10 mM, 150 mM), histidine (e.g., 20 mM), PS80 (e.g., 0.05%), and sucrose (up to 3%), and has a pH of 5.2 to 6.2. In some embodiments, the Aβ compositions comprise L-arginine hydrochloride, methionine, histidine, PS80, and sucrose, and has a pH of 5.5. In all of these embodiments, the anti-Aβ antibody is present at a concentration of 100 mg/ml to 165 mg/ml. In one instance, the anti-Aβ antibody is present at a concentration of 150 mg/ml. In one instance, the anti-Aβ antibody is present at a concentration of 100 mg/ml.

In some cases, the anti-Aβ composition comprises a thiol-containing antioxidant (e.g., reduced glutathione (GSH), oxidized glutathione (GSSG), GSH+GSSG, cysteine, cystine, cysteine+cystine) at a concentration of 0.02 mM to 4 mM (e.g., 0.02, 0.03, 0.05, 0.06, 0.08, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 mM). Such thiol-containing antioxidants can cleave unfavorable or mis-bridged disulfide bonds and promote the formation of favorable or properly bridged disulfide bonds. This would result in the stabilization of the native confirmation of the antibody or fragment thereof and slow down aggregation rates. The antioxidant properties of these molecules may slow down oxidative processes that lead to aggregation. In some cases, the composition comprises GSH at a concentration of 0.4 mM. In some cases, the composition comprises GSSG at a concentration of 0.2 mM. In some cases, the composition comprises GSH at a concentration of 0.4 mM and GSSG at a concentration of 0.2 mM. In some cases, the composition comprises GSH at a concentration of 4 mM and GSSG at a concentration of 2 mM. In some cases, the composition comprises GSH at a concentration of 2 mM and GSSG at a concentration of 1 mM. In some cases, the composition comprises cysteine at a concentration of 0.4 mM. In some cases, the composition comprises cystine at a concentration of 0.2 mM. In some cases, the composition comprises cysteine at a concentration of 0.4 mM and cystine at a concentration of 0.2 mM.

In certain embodiments, the Aβ compositions comprise arginine (e.g., Arg.HCl), a thiol-containing antioxidant, and methionine.

In certain embodiments, the Aβ compositions comprise L-arginine hydrochloride (e.g., 150 mM), methionine (e.g., 10 mM), histidine (e.g., 20 mM), a thiol-containing antioxidant such as GSH, GSSG, GSH and GSSG, cysteine, cystine, or cysteine and cystine (e.g., 0.02 mM to 4 mM), and PS80 (e.g., 0.05%), and has a pH of 5.2 to 6.2. In some embodiments, the Aβ compositions comprise L-arginine hydrochloride (e.g., 150 mM), methionine (e.g., 10 mM, 150 mM), histidine (e.g., 20 mM), a thiol-containing antioxidant such as GSH, GSSG, GSH and GSSG, cysteine, cystine, or cysteine and cystine (e.g., 0.02 mM to 4 mM), and PS80 (e.g., 0.05%), and has a pH of 5.5. In certain embodiments, the AP compositions comprise L-arginine hydrochloride (e.g., 150 mM), methionine (e.g., 10 mM, 150 mM), histidine (e.g., 20 mM), PS80 (e.g., 0.05%), a thiol-containing antioxidant such as GSH, GSSG, GSH and GSSG, cysteine, cystine, or cysteine and cystine (e.g., 0.02 mM to 4 mM), and sucrose (up to 3%), and has a pH of 5.2 to 6.2. In some embodiments, the AP compositions comprise L-arginine hydrochloride, methionine, histidine, PS80, a thiol-containing antioxidant such as GSH, GSSG, GSH and GSSG, cysteine, cystine, or cysteine and cystine, and sucrose, and has a pH of 5.5. In all of these embodiments, the anti-Aβ antibody is present at a concentration of 100 mg/ml to 165 mg/ml. In one instance, the anti-Aβ antibody is present at a concentration of 150 mg/ml. In one instance, the anti-Aβ antibody is present at a concentration of 100 mg/ml.

In certain embodiments, the composition (e.g., a pharmaceutical composition) comprises an anti-Aβ antibody or a Aβ-binding fragment thereof at a concentration of 50 mg/ml to 250 mg/ml, arginine (e.g., L-arginine hydrochloride) at a concentration of 50 mM to 200 mM, methionine at a concentration of 1 mM to 150 mM (e.g., 1 mM to 20 mM); polysorbate-80 at a concentration of 0.01% to 0.1%, histidine at a concentration of 10 mM to 30 mM, and sucrose at a concentration of 0% to 3%. In some cases, the composition has a pH of 5.2 to 6.2. In other cases, the composition has a pH of 5.2 to 6.0. In certain embodiments, the anti-Aβ antibody or a Aβ-binding fragment thereof of the composition comprises a VH and a VL comprising the CDRs of BIIB037 (e.g., SEQ ID NOs.: 1, 2, 3, 4, 5, and 6). In certain embodiments, the anti-Aβ antibody or a Aβ-binding fragment thereof of the composition comprises a VH and a VL comprising SEQ ID NOs: 7 and 8, respectively. In some embodiments, the anti-Aβ antibody or a Aβ-binding fragment thereof of the composition comprises a heavy chain and a light chain comprising SEQ ID NOs: 9 and 10, respectively. In one embodiment, the composition has a pH of 5.5 and comprises BIIB037 or a BIIB037-binding fragment thereof at a concentration of 150 mg/ml, L-arginine hydrochloride at a concentration of 150 mM, methionine at a concentration of 10 mM or 150,mM, polysorbate-80 at a concentration of 0.05%, and histidine at a concentration of 20 mM (16.2 mM L-histidine HCl monohydrate, 3.8 mM L-Histidine free base). In certain embodiments, the composition further comprises a thiol-containing antioxidant (e.g., GSH, GSSG, GSH+GSSG, cysteine, cystine, cysteine+cystine) at a concentration of 0.02 mM to 4 mM. In some embodiments, the composition further comprises sucrose at a concentration of 0.01% to 3%. In certain embodiments, the anti-Aβ antibody or Aβ-binding fragment thereof of the composition comprises a VH and a VL comprising the CDRs of BIIB037 (e.g., SEQ ID NOs.: 1, 2, 3, 4, 5, and 6). In certain embodiments, the anti-Aβ antibody or Aβ-binding fragment thereof of the composition comprises a VH and a VL comprising SEQ ID NOs: 7 and 8, respectively. In some embodiments, the anti-Aβ antibody or Aβ-binding fragment thereof of the composition comprises a heavy chain and a light chain comprising SEQ ID NOs: 9 and 10, respectively.

In one embodiment, the composition has a pH of 5.5 and comprises BIIB037 or a BIIB037-binding fragment thereof at a concentration of 150 mg/ml, L-arginine hydrochloride at a concentration of 150 mM, a thiol-containing antioxidant (e.g., GSH, GSSG, GSH+GSSG, cysteine, cystine, cysteine+cystine) at a concentration of 0.02 mM to 4 mM, polysorbate-80 at a concentration of 0.05%, and histidine at a concentration of 20 mM. In one embodiment, the thiol-containing antioxidant is GSH at a concentration of 0.4 mM. In one embodiment, the thiol-containing antioxidant is GSH at a concentration of 0.4 mM and GSSG at a concentration of 0.2 mM. In one embodiment, the thiol-containing antioxidant is GSH at a concentration of 4 mM and GSSG at a concentration of 2 mM. In one embodiment, the thiol-containing antioxidant is GSH at a concentration of 2 mM and GSSG at a concentration of 1 mM. In another embodiment, the thiol-containing antioxidant is cysteine at a concentration of 0.4 mM. In another embodiment, the thiol-containing antioxidant is cysteine at a concentration of 0.4 mM and cystine at a concentration of 0.2 mM.

Methods of Treatment

BIIB037 recognizes aggregated forms of Aβ, including plaques. In vitro characterization studies have established that antibody BIIB037 recognizes a conformational epitope present in Aβ aggregates, the accumulation of which is believed to underlie the development and progression of Alzheimer's disease (AD). In vivo pharmacology studies indicate that a murine IgG2a chimeric version of the antibody (ch12F6A) with similar properties significantly reduces amyloid plaque burden in the brains of aged Tg2576 mice, a mouse model of AD. The reduction in parenchymal amyloid was not accompanied by a change in vascular amyloid, as has been reported for certain anti-Aβ antibodies.

The compositions disclosed herein are useful in treating abnormal accumulation or deposition of Aβ in the central nervous system of a human subject in need thereof. The compositions disclosed herein are also useful in treating mild cognitive impairment in a human subject in need thereof. As used herein, the terms "treat", "treating", or "treatment" generally mean obtaining a desired pharmacological and/or physiological effect.

In certain embodiments, the compositions disclosed herein are useful in treating AD in a human subject in need thereof. In other embodiments, the compositions disclosed herein are useful in preventing AD in a human subject in need thereof.

The compositions disclosed herein can be used to: (a) prevent AD from occurring in a subject who may be predisposed to AD, but has not yet been diagnosed as having it; (b) inhibiting AD, e.g. arresting its development; (c) relieving AD, e.g. causing regression of AD; or (d) prolonging survival as compared to expected survival if not receiving treatment.

A human subject in need thereof is administered a therapeutically effective amount or dose of the anti-Aβ antibody or Aβ-binding fragment thereof. A therapeutically effective amount refers to the amount of the antibody sufficient to ameliorate a symptom or condition associated with AD. Therapeutic efficacy and toxicity of the antibody can be determined by standard pharmaceutical procedures. Ideally, the antibody is employed in an amount sufficient to restore normal behavior and/or cognitive properties in case of Alzheimer's disease, or at least delay or prevent the progression of AD in the patient.

In some embodiments, the composition comprising the anti-Aβ antibody or Aβ-binding fragment thereof is administered intravenously to the human subject. In certain embodiments, the composition comprising the anti-Aβ antibody or Aβ-binding fragment thereof is administered subcutaneously to the human subject.

The following are examples of the practice of the invention. They are not to be construed as limiting the scope of the invention in any way.

EXAMPLES

Example 1: pH and Buffer Screened for Optimal Formulation

The following formulations were prepared and screened to determine the optimal buffer and pH.

TABLE 6 pH and buffer screen formulations

| Buffer | pH | Excipients | Protein Concentration |
|---|---|---|---|
| 20 mM Acetate | 4.5 | 150 mM L-Arginine HCl | 155-165 mg/mL |
|  | 5.0 | 0.05% Polysorbate-80 |  |
|  | 5.5 |  |  |
| 20 mM Succinate | 4.5 |  |  |
|  | 5.0 |  |  |
|  | 5.5 |  |  |
|  | 6.0 |  |  |

TABLE 6-continued pH and buffer screen formulations

| Buffer | pH | Excipients | Protein Concentration |
|---|---|---|---|
| 20 mM Histidine | 5.5 |  |  |
|  | 6.0 |  |  |
|  | 6.5 |  |  |
| 20 mM Citrate | 5.0 |  |  |
|  | 5.5 |  |  |
|  | 6.0 |  |  |
|  | 6.5 |  |  |

Formulations were stored at 40° C.+75% relative humidity (RH) for 4 weeks (FIG. 1).

Conclusions:

1) Histidine buffer showed the lowest change in percentage high molecular weight species (% HMW) compared to Acetate, Succinate, and Citrate buffers.

2) The trend was consistent across the pH range of 5.5 to 6.5.

Example 2: Arginine as an Optimal Excipient for Controlling HMW

The following formulations were prepared to determine the optimal stabilizing excipient(s). Most contain L-Arginine HCl, either alone or combined with another excipient. Two formulations did not contain Arginine and only contained a sugar (sucrose or trehalose).

TABLE 7

Excipient screen formulations

| Excipient (all contain 20 mM Histidine and 0.05% Polysorbate-80) | pH | Protein concentration |
|---|---|---|
| 150 mM L-Arginine HCl | 6.0 | 220-230 mg/mL |
| 150 mM L-Arginine HCl | 5.5 |  |
| 100 mM L-Arginine HCl | 5.5 |  |
| 100 mM L-Arginine HCl + 3% Sucrose | 5.5 |  |
| 100 mM L-Arginine HCl + 3% Sucrose | 6.0 |  |
| 100 mM L-Arginine HCl + 50 mM NaCl | 5.5 |  |
| 75 mM L-Arginine HCl + 75 mM glutamate | 5.5 |  |
| 150 mM L-Arginine HCl + 10 mM Methionine | 5.5 |  |
| 150 mM L-Arginine HCl + 10 mM Methionine | 6.0 |  |
| 300 mM Sucrose | 5.5 |  |
| 300 mM Trehalose | 5.5 |  |
| 50 mM L-Arginine HCl + 4.5% Sucrose | 5.5 |  |

Figure 2:
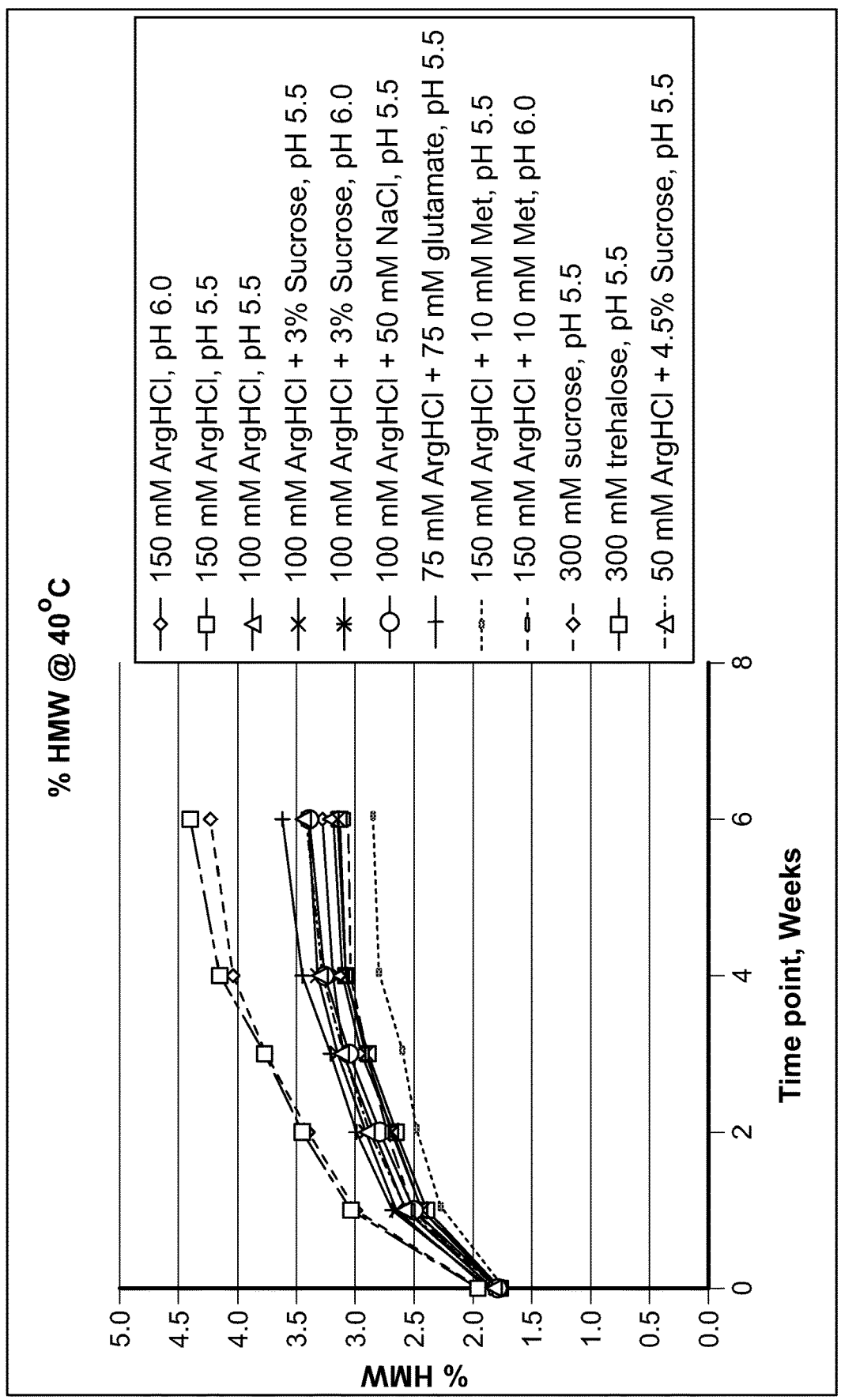
FIG. 2 is a graph showing the % HMW for the indicated formulations stored at 40° C. for 6 weeks.

The formulations were stored at 40° C.+75% RH and tested for % HMW over 6 weeks (FIG. 2).

Conclusions:

1) Formulations containing Arginine (solid lines) performed better than the formulations without Arginine (dashed lines).

2) The Arginine+Methionine combination (lowest two solid lines in the plot) performed better than Arginine alone and Arginine in combination with other excipients.

3) Formulations prepared at both pH 5.5 and 6.0 always performed better at pH 5.5.

Example 3: Robustness of the Formulation for pH and Protein Concentration

Further formulation optimization was performed by preparing various formulations based around a central formulation (Table 8) and screening for various quality attributes.

TABLE 8

Optimization screen formulations.

| Formulation Variation | [Protein] mg/mL | pH | Buffer (20 mM) | Arginine (mM) | Methionine (mM) | Sucrose (%) | PS-80 (%) |
|---|---|---|---|---|---|---|---|
| Center formulation | 220 | 5.7 | His | 150 | 10 | | 0.05 |
| Center @ 165 mg/mL | 165 | 5.7 | His | 150 | 10 | | 0.05 |
| Center @ 280 mg/mL | 280 | 5.7 | His | 150 | 10 | | 0.05 |
| Center @ pH 5.2 | 220 | 5.2 | His | 150 | 10 | | 0.05 |
| Center @ pH 6.2 | 220 | 6.2 | His | 150 | 10 | | 0.05 |
| Center with 100 mM Arginine | 220 | 5.7 | His | 100 | 10 | | 0.05 |
| Center without Methionine | 220 | 5.7 | His | 150 | 0 | | 0.05 |
| Center with 100 mM Arginine + 3% Sucrose | 220 | 5.7 | His | 100 | 0 | 3 | 0.05 |
| Center with 20 mM Citrate | 220 | 5.7 | Citrate | 150 | 10 | | 0.05 |

Figure 3:
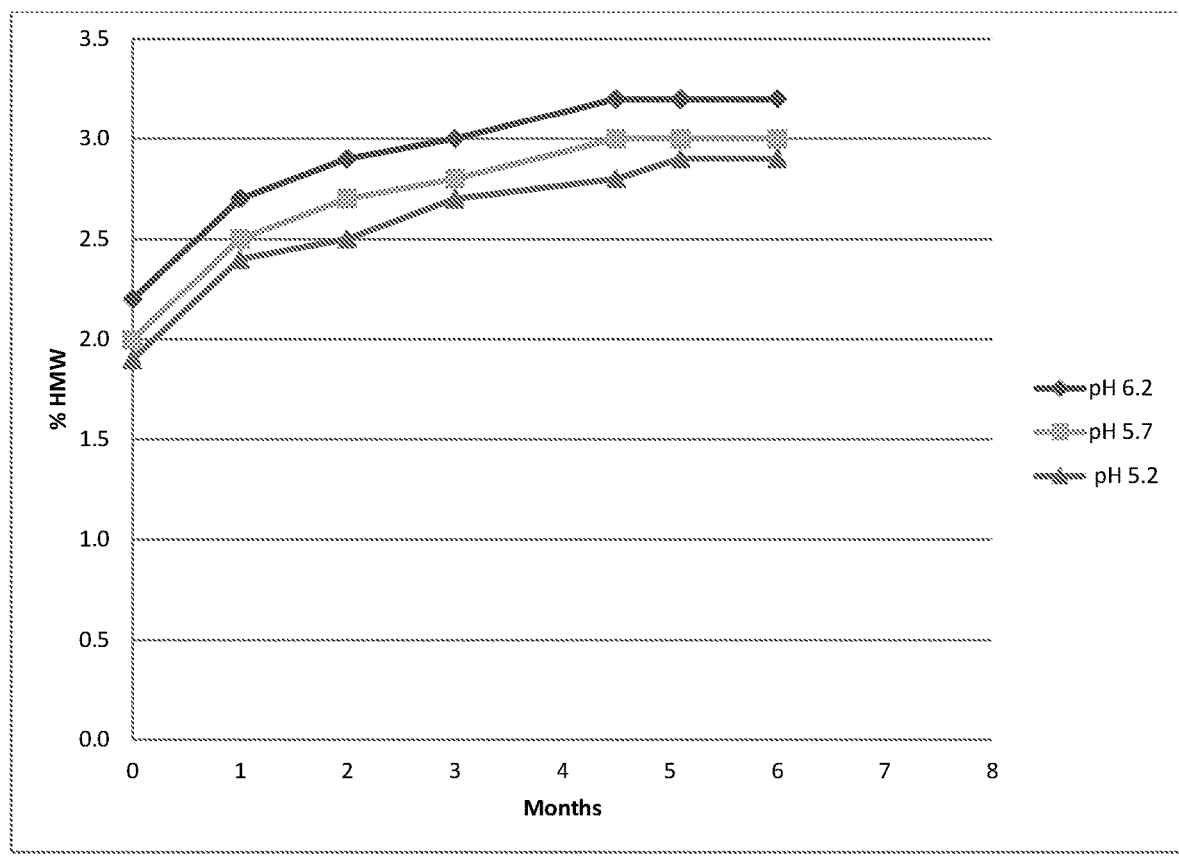
FIG. 3 is a graph showing the % HMW trends at varying pH when stored at 25° C.+60% relative humidity.

FIG. 3 shows the % HMW trends at varying pH when stored at 25° C.+60% relative humidity. The rate of increase of % HMW over time is consistent across this pH range.

Figure 4:
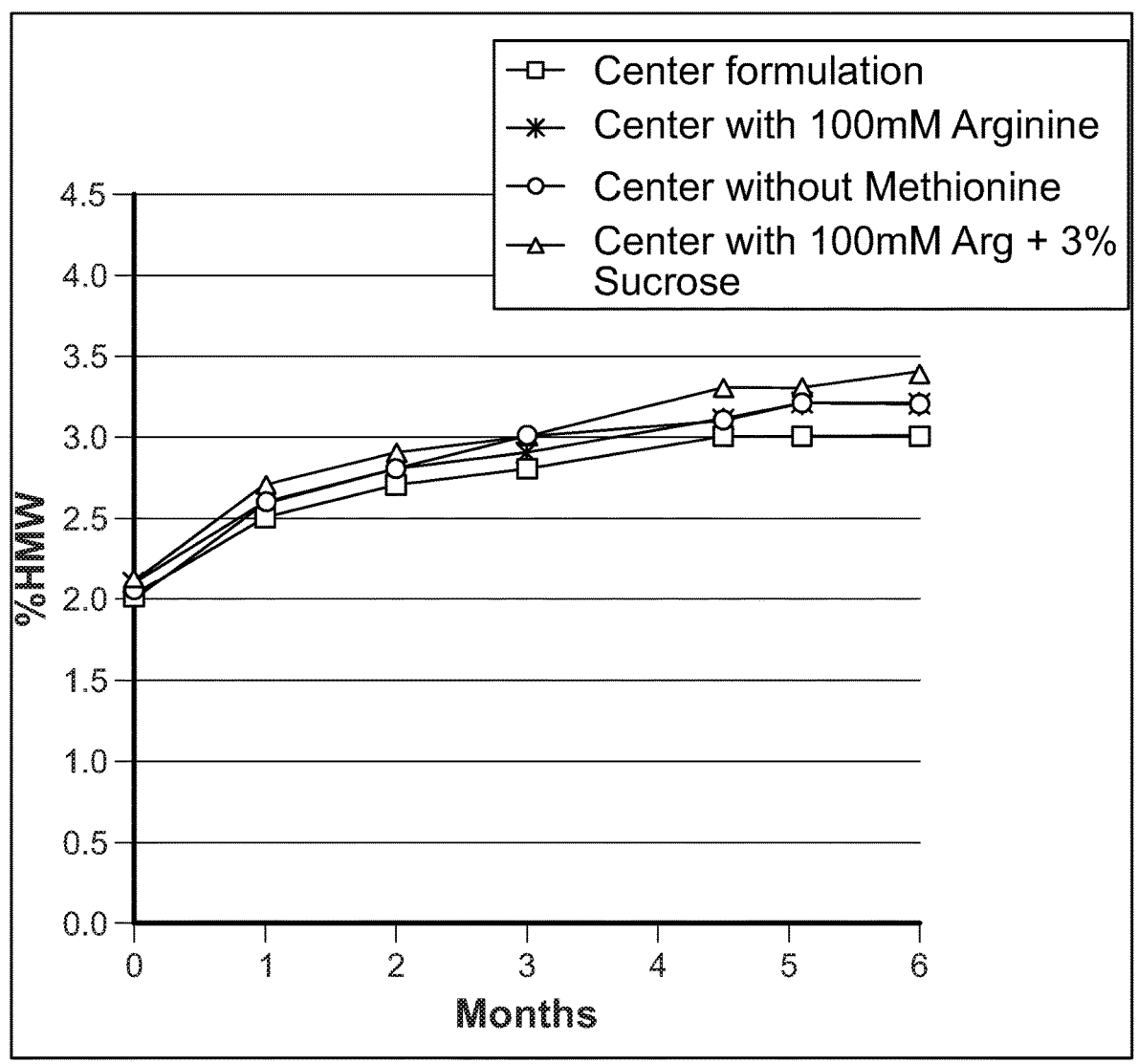
FIG. 4 is a graph showing the % HMW trends for varying excipients when stored at 25° C.+60% relative humidity.

FIG. 4 shows the % HMW trends for varying excipients when stored at 25° C.+60% relative humidity. The rate of increase of % HMW is consistent whether the stabilizing excipient is 150 mM L-Arginine HCl+10 mM Methionine, 100 mM L-Arginine HCl+10 mM Methionine, 150 mM L-Arginine HCl without Methionine, or 100 mM L-Arginine HCl+3% Sucrose.

Example 4: Arginine Lowers Viscosity of the Formulations

Figure 5:
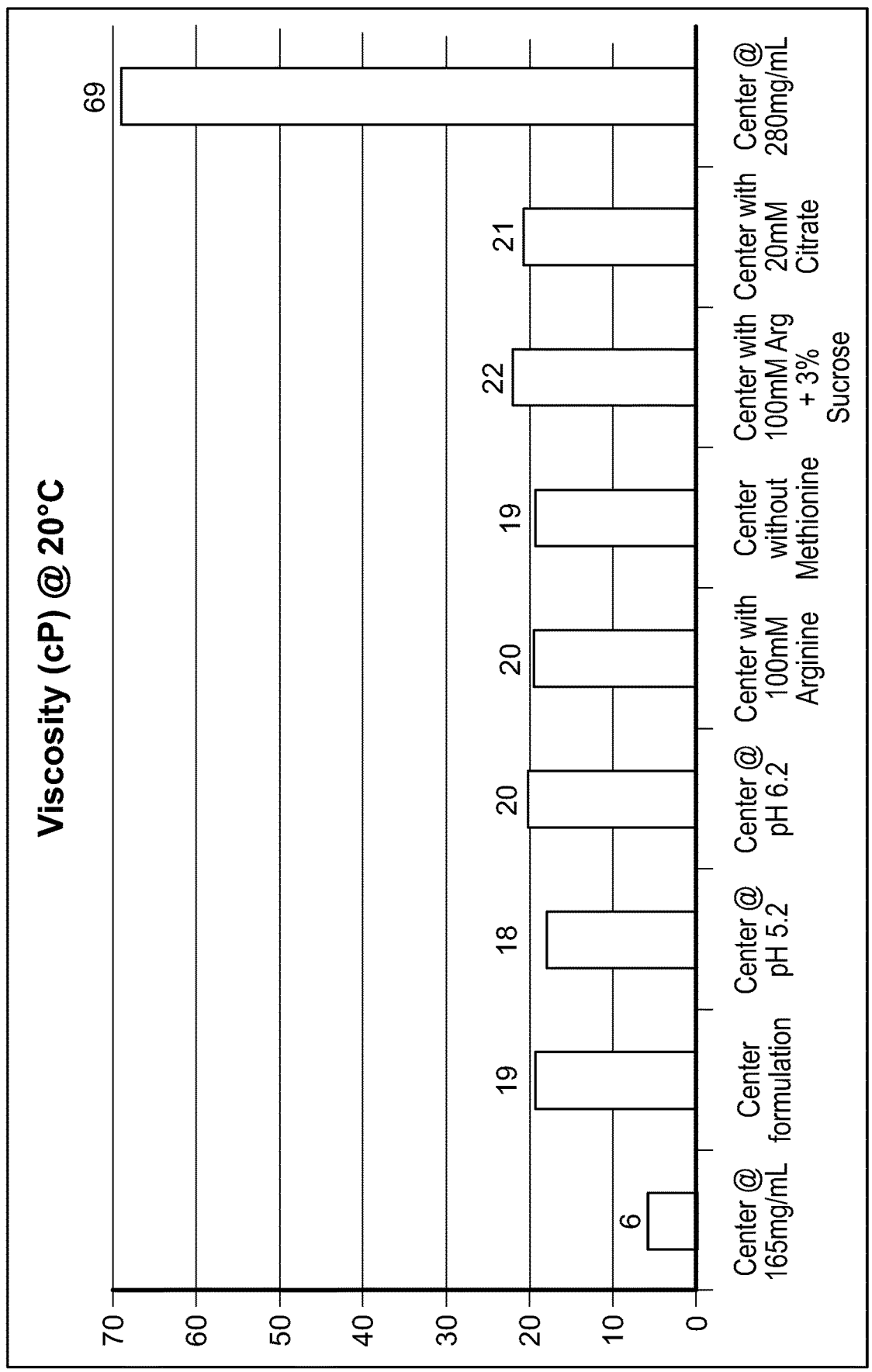
FIG. 5 is a bar graph showing the viscosity at 20° C. for formulations.

The viscosity of each formulation was measured at ambient temperature (20° C.). The protein concentration has a significant impact on viscosity, while other variations in the formulation recipe did not have impact. Viscosities <50 cP are optimal for manufacturing processes and route of administration options. The Arginine-based formulations provide consistently low viscosity (~20 cP) at high protein concentration (~220 mg/mL) (FIG. 5).

Example 5: Robustness of Formulation to Polysorbate-80 Concentration

The following formulations were prepared to assess the optimal level of surfactant (Polysorabate-80) in the formulation.

TABLE 9

Surfactant screen formulations

| Protein Concentration (mg/mL) | pH | Buffer | Excipients | % Polysorbate-80 |
|---|---|---|---|---|
| 160 | 5.7 | 20 mM Histidine | 150 mM L-Arginine HCl + 10 mM Methionine | 0.00% |
| | | | | 0.005% |
| | | | | 0.01% |
| | | | | 0.03% |
| | | | | 0.05% |
| | | | | 0.075% |
| | | | | 0.10% |

An agitation study was performed to determine the appropriate level of surfactant necessary to maintain product stability during physical stress. The formulations in Table 9 were dispensed into 3 mL glass vials and 1 mL glass staked-needle syringes, then agitated at 650 rpm for 72 hours at room temperature. Unagitated controls were stored in glass vials for the same time and temperature.

Figure 6:
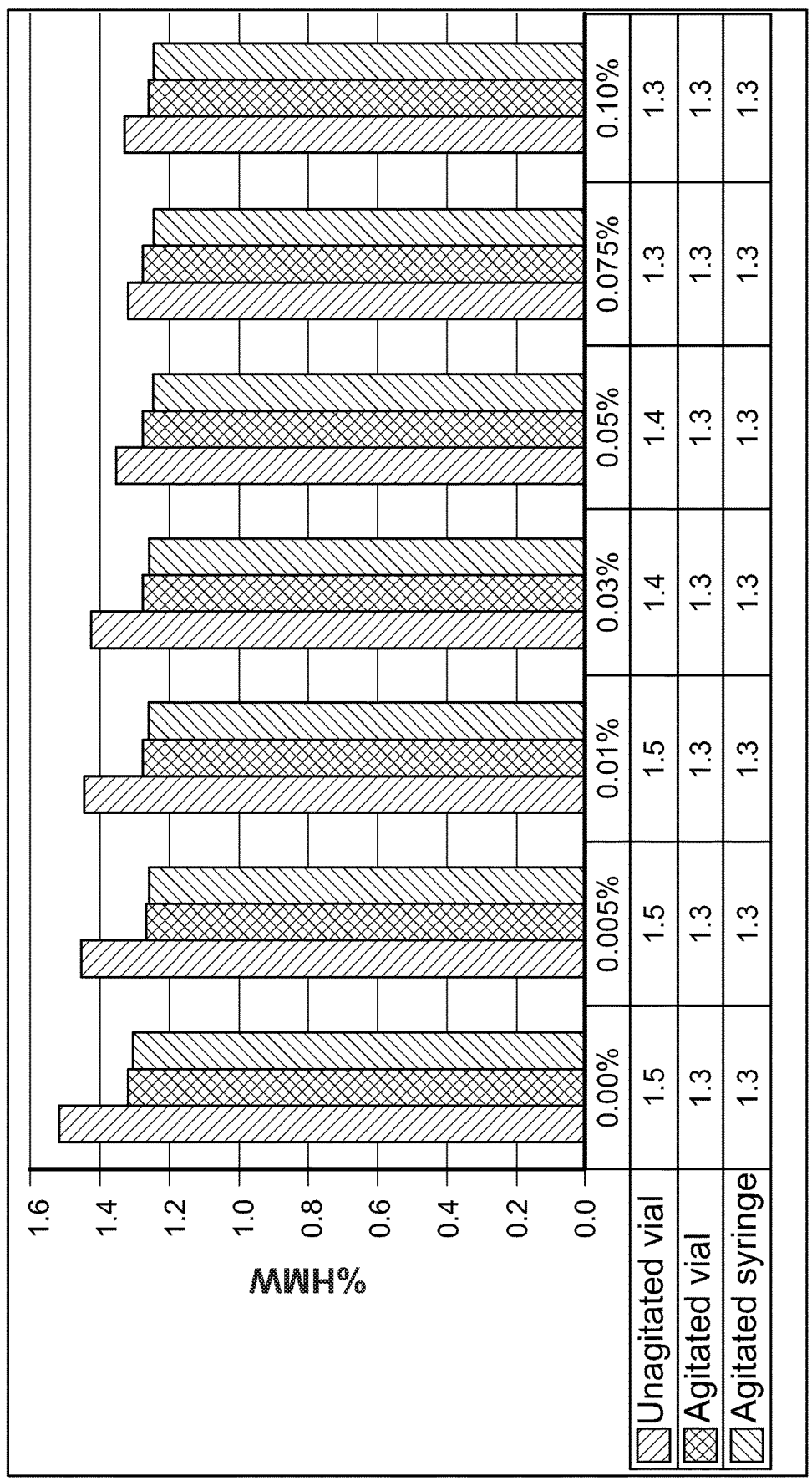
FIG. 6 is a bar graph depicting the % HMW results for polysorbate-80 formulations after 72 hours at room temperature.

% HMW results were consistent across all agitated formulations (FIG. 6). The unagitated control vials show a gradual increase in HMW as the % polysorbate-80 drops from 0.05% to 0.00%. All results are within the variability (noise) of the method (±0.2%) and may not be real differences. Stability is comparable across a broad range of % Polysorbate-80.

Example 6: Thiol Group Containing Excipients Improve Aggregation Stability of Aducanumab Formulation The addition of thiol group containing excipients to an Aducanumab formulation reduces aggregation as determined by the development of high molecular weight species during storage.

Figure 7:
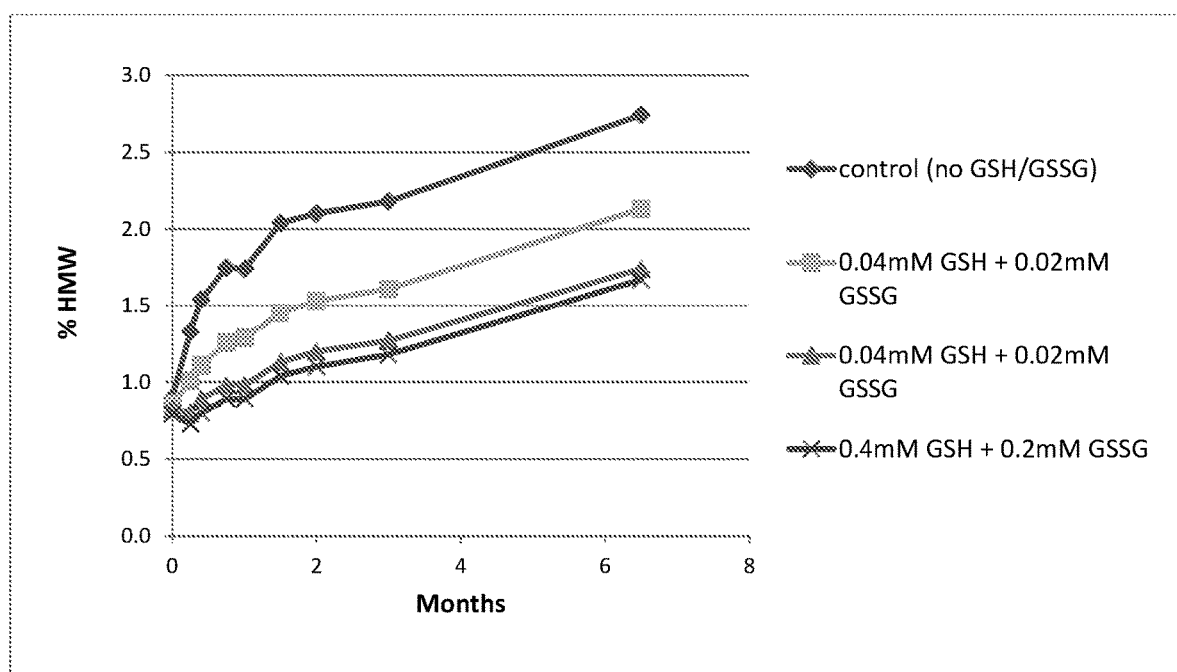
FIG. 7 is a graph showing the effect of the combination of GSH and GSSG on the stability of Aducanumab formulations at 25° C. and 60% relative humidity.

The control Aducanumab formulation has 165 mg/mL Aducanumab, 20 mM Histidine, 150 mM L-Arginine HCl, 10 mM Methionine, 0.05% Polysorbate-80, pH 5.5. The control formulation was spiked with thiol group containing excipients: GSH and GSSG. The formulations were stored at 25° C. at 60% relative humidity. As shown in FIG. 7, the addition of GSH and GSSG reduces the development of HMW species during storage.

Figure 8:
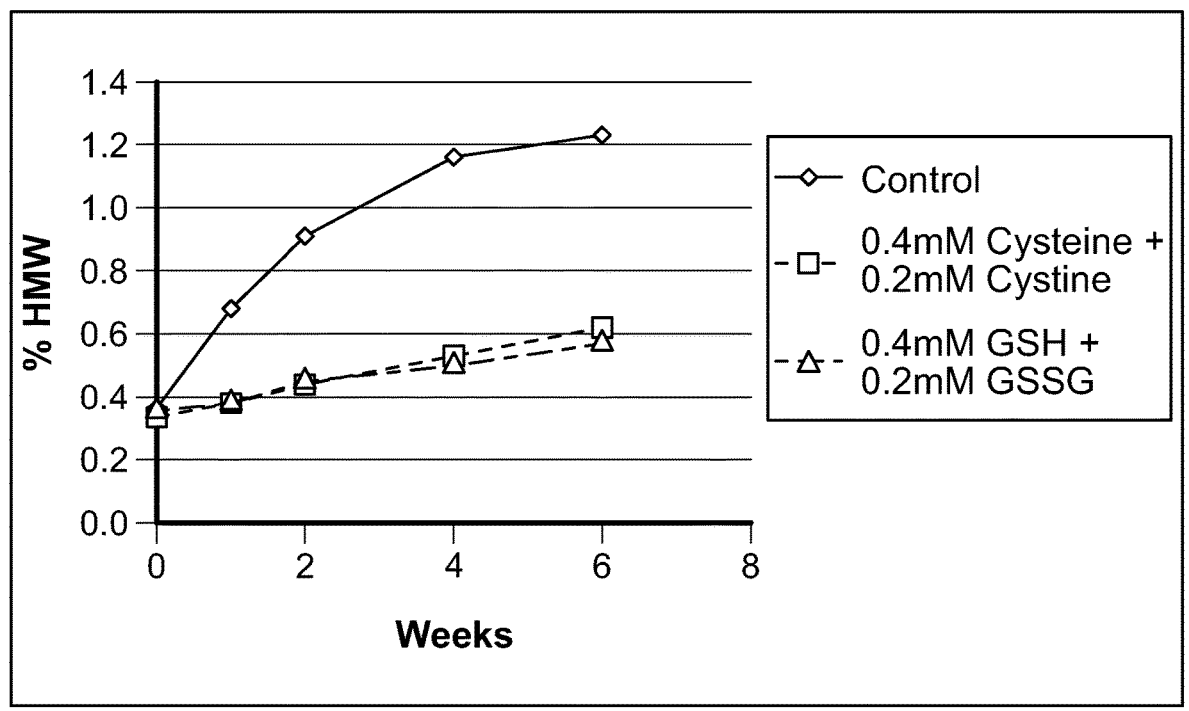
FIG. 8 is a graph showing the effect of the combination of Cysteine and Cystine on the stability of Aducanumab formulations at 25° C. and 60% relative humidity.

The same control formulation of Aducanumab was spiked with Cysteine and Cystine. These formulations were also stored at 25° C. at 60% relative humidity. As was the case for GSH and GSGG, the addition of Cysteine and Cystine suppresses the development of HMW species during storage (FIG. 8).

Example 7: Reduced Form of Thiol Group Containing Excipient is as Effective as Redox Pair in Controlling HMW The addition of the reduced form of a thiol group containing excipient alone has the same impact as the addition of the redox pair.

Figure 9:
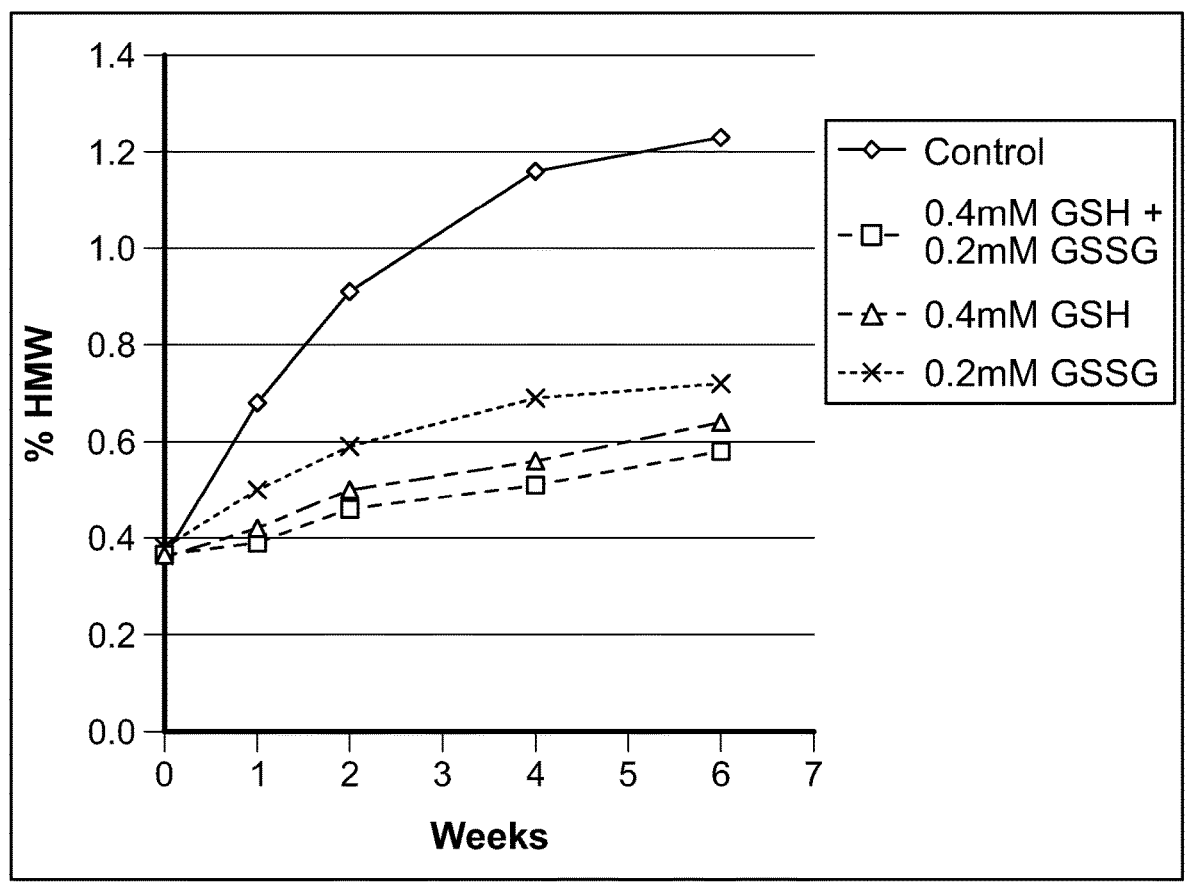
FIG. 9 is a graph showing that the reduced form of a thiol-containing excipient has the same impact on stability at 25° C. and 60% relative humidity as the redox pair.

A control Aducanumab formulation contains 165 mg/mL Aducanumab, 20 mM Histidine, 150 mM L-Arginine HCl, 10 mM Methionine, 0.05% Polysorbate-80, pH 5.5. This formulation was spiked with GSH+GSSG, GSH alone, or GSSG alone. The formulations were stored at 25° C. at 60% relative humidity. As shown in FIG. 9, the addition of GSH, GSSG, and GSH+GSSG all reduced the formation of HMW species.

Example 8: Thiol Containing Excipients are Better than Methionine in Controlling HMW The addition of methionine does not increase the stability observed with GSH alone.

Figure 10:
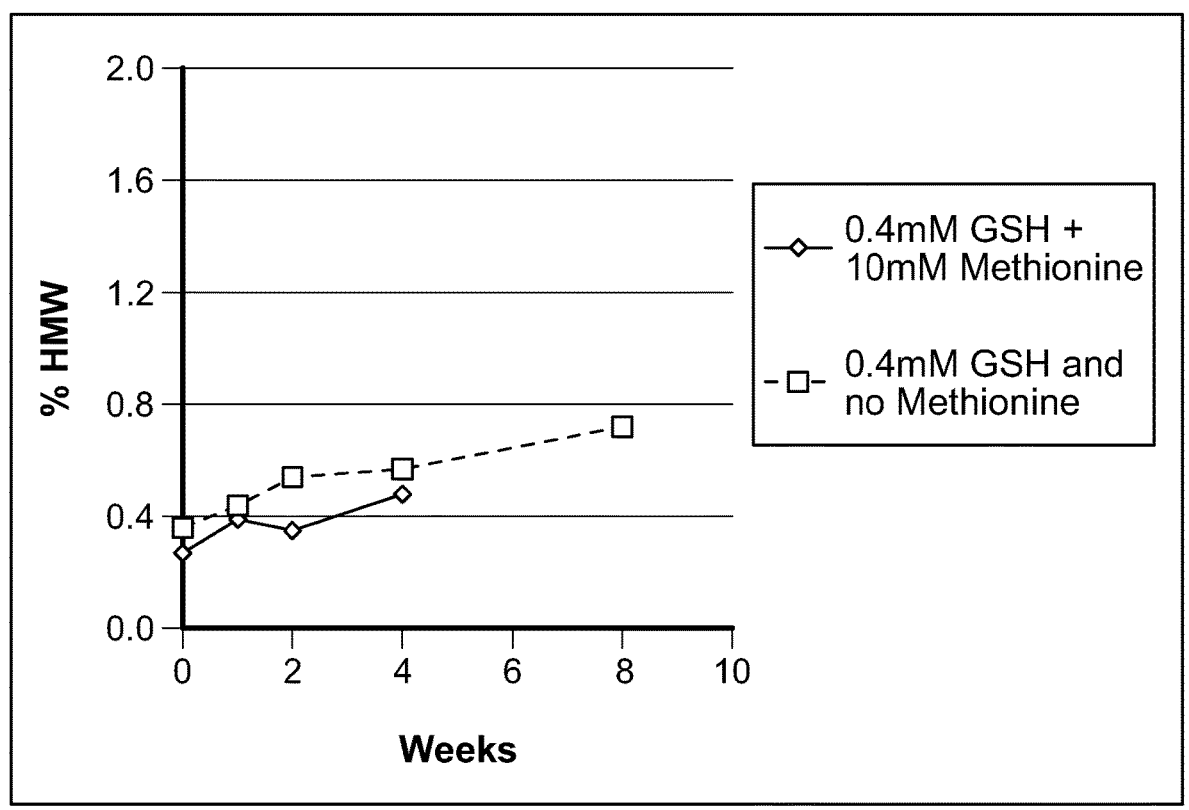
FIG. 10 is a graph illustrating that methionine provides limited benefit when combined with GSH on the stability of Aducanumab formulations at 25° C. and 60% relative humidity.

A control Aducanumab formulation has 165 mg/mL Aducanumab, 20 mM Histidine, 150 mM L-Arginine HCl, pH 5.5. GSH or GSH+Methionine were added to the control formulation. These formulations were stored at 25° C. at 60% relative humidity. The addition of methionine did not provide any additive benefit to the reduction in HMW species observed with GSH alone (FIG. 10).

Example 9: Robustness for Thiol-Containing Excipient Formulation at Multiple Protein and GSH Concentrations Reduction in HMW species with the addition of GSH was observed at multiple concentrations of protein and multiple concentrations of GSH.

Figure 11:
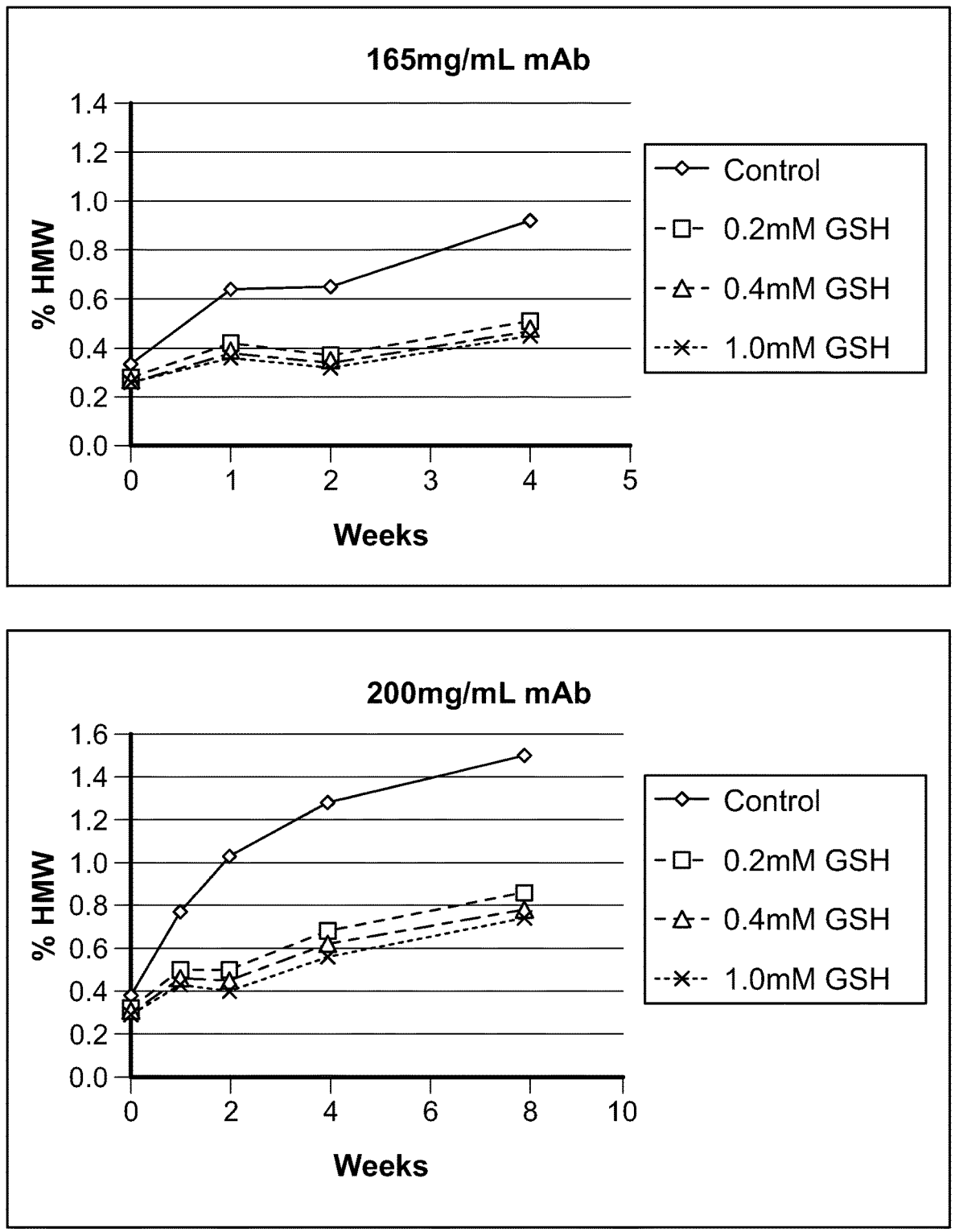
FIG. 11 is a pair of graphs showing the effect of different antibody concentrations and GSH on stability at 25° C. and 60% relative humidity.

Aducanumab (165 or 200 mg/mL Aducanumab, 20 mM Histidine, 150 mM L-Arginine HCl, 10 mM Methionine, 0.05% Polysorbate-80, pH 5.5) was stored at 25° C. at 60% relative humidity with various concentrations of GSH. As shown in FIG. 11, GSH suppresses HMW species formation at concentrations from 0.2 mM to 1.0 mM, at protein concentrations up to 200 mg/ml.

Example 10: Thiol-Containing Excipient is Effective in Controlling HMW at Very Low Concentrations Concentrations of a thiol-containing excipient as low as 0.02 mM improved the stability of Aducanumab at various concentrations.

Figure 12:
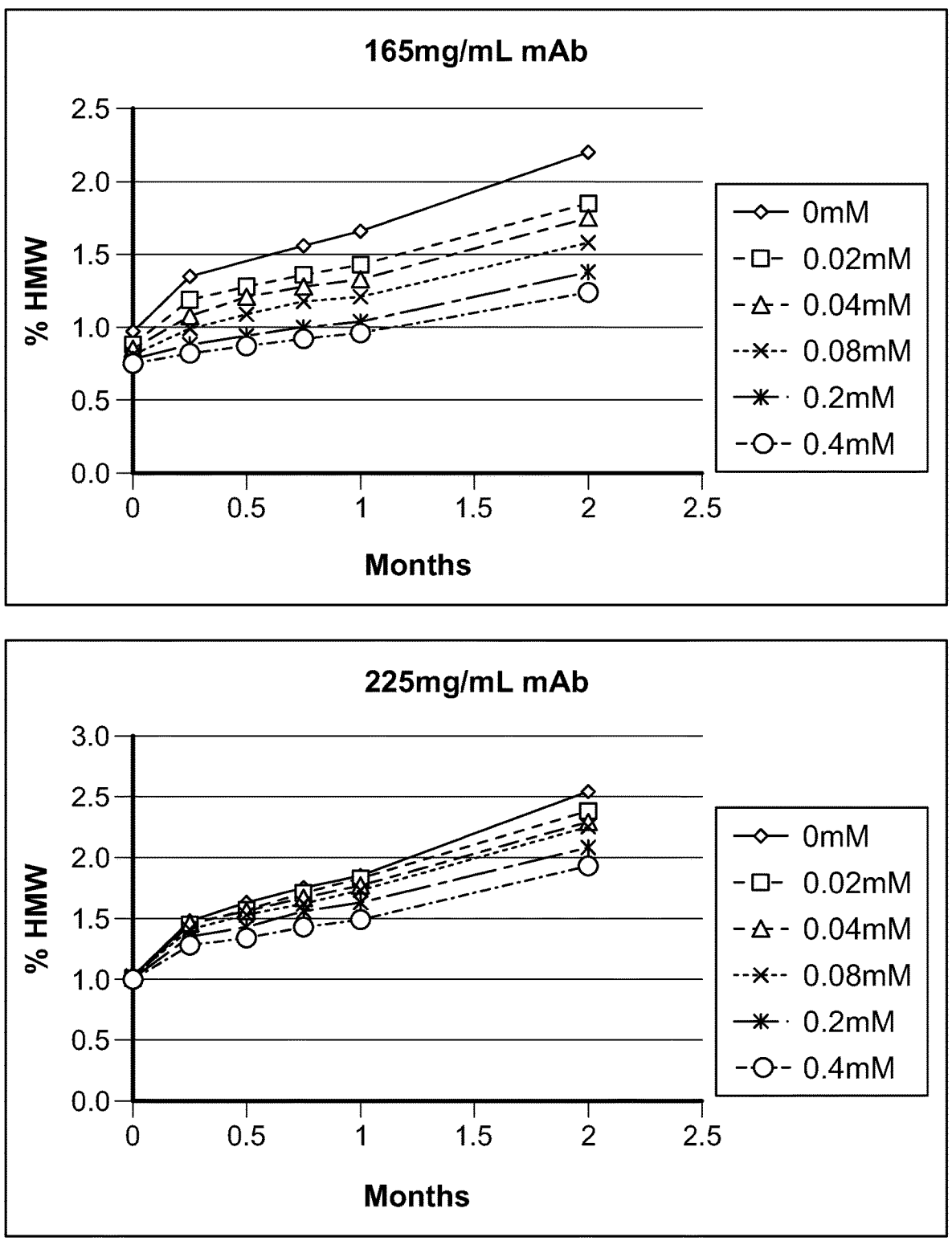
FIG. 12 is a pair of graphs showing that even low concentrations of GSH can improve HMW stability.

Aducanumab (165 or 225 mg/mL Aducanumab, 20 mM Histidine, 150 mM L-Arginine HCl, 10 mM Methionine, 0.05% Polysorbate-80, pH 5.5) was stored at 25° C. at 60% relative humidity with various concentrations of GSH. As shown in FIG. 12, GSH suppresses HMW species formation at concentrations as low as 0.02 mM in formulations containing up to 225 mg/ml Aducanumab.

Example 11: Effect of Increasing Thiol-Containing Excipient on HMW

This experiment was performed to assess the impact of increasing the concentration of GSH on HMW reduction.

All tested formulations contained 210 mg/mL aducanumab, 20 mM histidine, 150 mM arginine, 10 mM methionine, and 0.05% polysorbate-80, and only differed by the GSH concentration. The GSH concentrations tested were 0 mM, 0.5 mM, 1 mM, 2 mM, and 4 mM. Samples were stored at 25° C., 60% relative humidity for up to 4.5 months.

Figure 13:
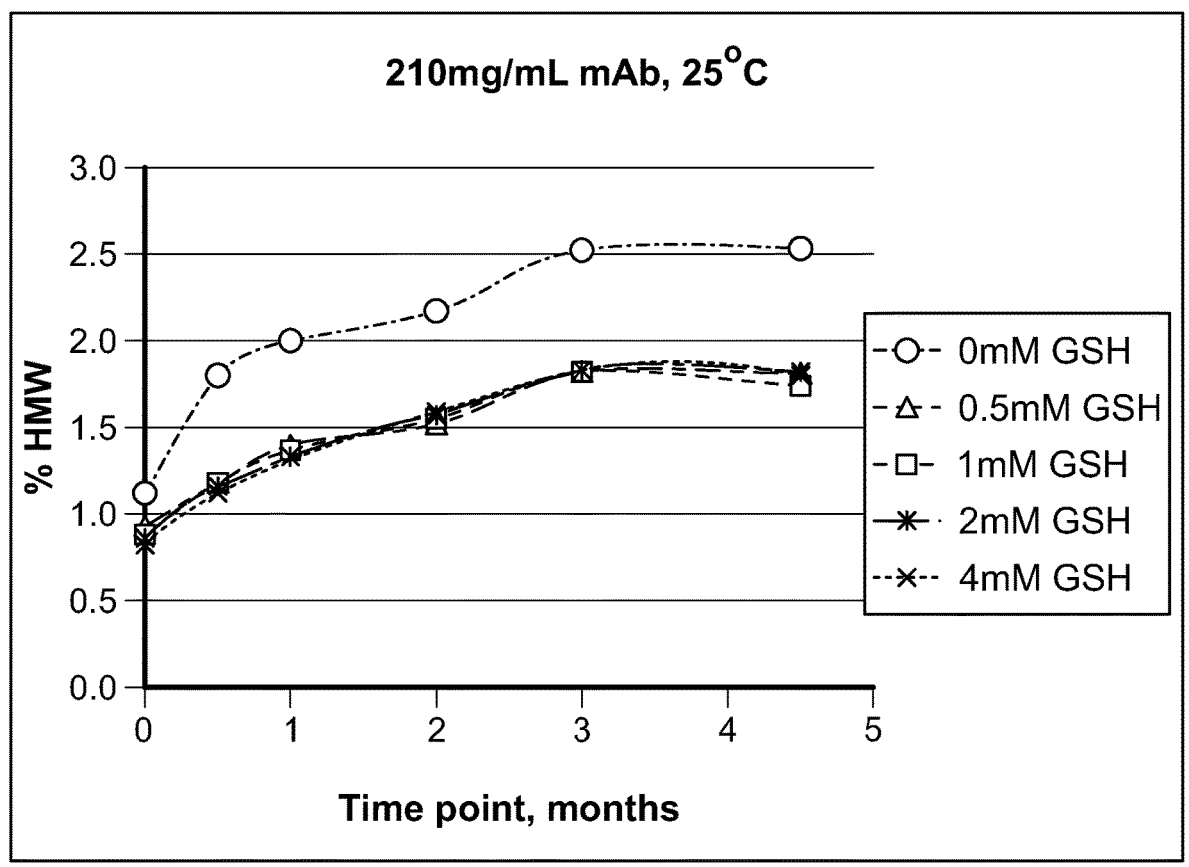
FIG. 13 is a graph showing that GSH at 4 mM has the same impact on HMW reduction as GSH from 0.5 mM to 2 mM.

The data showed that GSH at 4 mM has same impact on HMW reduction as GSH from 0.5 mM to 2 mM (see, FIG. 13).

Example 12: Effect of Increasing Methionine Concentrations on HMW

This experiment was performed to assess the impact of increasing the concentration of methionine on HMW reduction.

Figure 14:
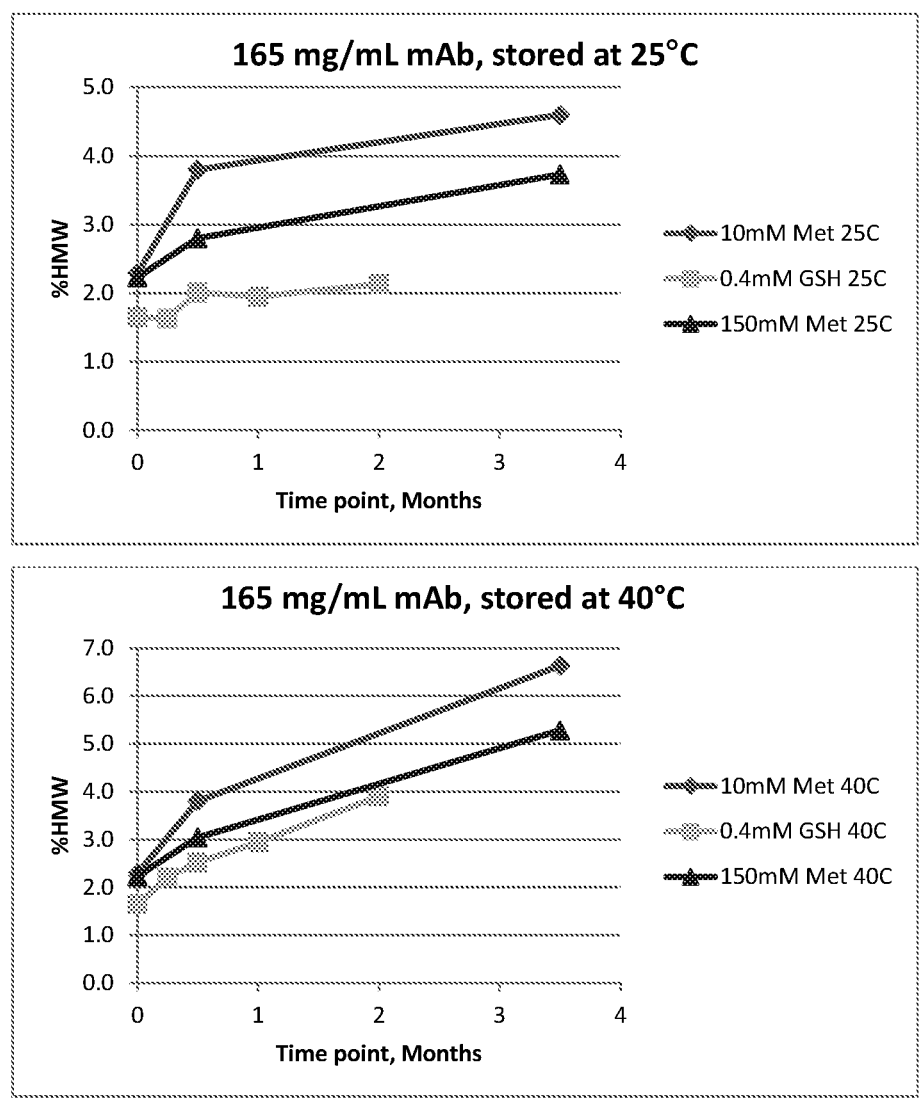
FIG. 14 is a pair of graphs showing the effect of increasing methionine on HMW levels at 25° C. (top) and 40° C. (bottom).

All tested formulations contained 165 mg/mL aducanumab, 20 mM histidine, 150 mM arginine, and 0.05% polysorbate-80, and only differed by the concentration of methionine or GSH as shown in FIG. 14. Samples were stored at 25° C., 60% relative humidity (top) and 40° C., 75% relative humidity (bottom) for up to 3.5 months.

This experiment showed that that increasing the methionine concentration to 150 mM helped reduce HMW compared to 10 mM methionine.

Example 13: A 4-Week Tolerability and Toxicokinetic Study of BIIB037 when Administered by Intravenous and Subcutaneous Injection to Cynomolgus Monkeys The objective of this study was to determine the tolerability of BIIB037 (150 mg/mL strength in 20 mM histidine buffer [16.2 mM L-histidine monohydrate, 3.8 mM L-histidine free base], 150 mM L-arginine hydrochloride (HCl), 10 mM methionine, and 0.05% polysorbate 80 pH 5.5) when given by intravenous (IV) or subcutaneous (SC) injection once a week for 4 weeks to 3 cynomolgus monkeys per group. In addition, the toxicokinetic characteristics of the test article were determined.

Both IV and SC administration of BIIB037 at 300 mg/kg/dose once a week for 4 weeks (Day 22 area under the concentration-time curve from time 0 to time t [AUC0–t]: 324,000 μg·h/mL and 243,000 μg·h/mL for IV and SC, respectively) resulted in no clinical observations, or adverse effects on body weight or food consumption. The SC injection site observations were limited to one SC injected animal following the third and fourth week administrations that consisted of non-adverse, very slight erythema and/or edema, accompanied by likely procedure-related mild focal neutrophilic and mononuclear cellular infiltration and hemorrhage (associated with the fourth injection site only). The absolute % bioavailability ranged from 56.7% to 75.1% for AUCτ on SD 1 and SD 22 indicating good absorption kinetics following aducanumab SC administration. The summary of mean TK parameters is presented in Table 10.

TABLE 10

Summary of Mean Toxicokinetic Parameters in the 4-Week IV and SC Male Cynomolgus Monkey Study

| | Dose | |
| --- | --- | --- |
| Number of Animals | 300 mg/kg IV M (3) | 300 mg/kg SC M (3) |
| Day 1 | | |
| $C_{max}$ (μg/mL) | 6,930 | 1,180 |
| $AUC_\tau$ (μg*h/mL) | 236,000 | 134,000 |
| $T_{max}$ (h) | 0.083 | 12 or 24 |
| Day 22 | | |
| $C_{max}$ (μg/mL) | 7,070 | 2,490 |
| $AUC_\tau$ (μg*h/mL) | 324,000 | 243,000 |
| $T_{max}$(h) | 0.083 to 2 | 12 to 24 |

$AUC_\tau = AUC_{0-t}$ (TK parameter used in P037-16-01 study report) = area under the concentration-time curve from time 0 to last concentration;
$C_{max}$ = maximum observed concentration, occurring at $T_{max}$;
SD = Study Day;
$T_{max}$ = time of maximum observed concentration

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A pharmaceutical composition comprising:
   (i) an anti-beta amyloid (Aβ) antibody or Aβ-binding fragment thereof at a concentration of 100 mg/ml to 200 mg/ml;
   (ii) arginine hydrochloride (Arg.HCl) at a concentration of 75 mM to 175 mM;
   (iii) methionine at a concentration of 5 mM to 15 mM;
   (iv) histidine at a concentration of 10 mM to 30 mM;
   (v) polysorbate-80 (PS80) at a concentration (w/v) of 0.03% to 0.08%; and
   (vi) a thiol-containing antioxidant selected from the group consisting of GSH, GSSG, the combination of GSH and GSSG, cystine, cysteine, and the combination of cystine and cysteine, wherein the thiol-containing antioxidant is at a concentration of 0.02 mM to 4 mM, wherein the anti-Aβ antibody or Aβ-binding fragment thereof comprises an immunoglobulin heavy chain variable domain (VH) and an immunoglobulin light chain variable domain (VL), wherein
   (a) the VH comprises
       a VH-CDR1 that consists of the amino acid sequence set forth in SEQ ID NO:1;
       a VH-CDR2 that consists of the amino acid sequence set forth in SEQ ID NO:2; and
       a VH-CDR3 that consists of the amino acid sequence set forth in SEQ ID NO:3; and
   (b) the VL comprises
       a VL-CDR1 that consists of the amino acid sequence set forth in SEQ ID NO:4;
       a VL-CDR2 that consists of the amino acid sequence set forth in SEQ ID NO:5; and
       a VL-CDR3 that consists of the amino acid sequence set forth in SEQ ID NO:6, and
   wherein the composition has a pH of 5.2 to 6.2.

2. The pharmaceutical composition of claim 1, wherein the composition comprises the anti-Aβ antibody or Aβ-binding fragment thereof at a concentration of 175 mg/ml.

3. The pharmaceutical composition of claim 1, wherein the thiol-containing antioxidant is at a concentration of 0.4 mM.

4. The pharmaceutical composition of claim 1, wherein the composition comprises Arg.HCl at a concentration of 150 mM.

5. The pharmaceutical composition of claim 1, wherein the composition comprises PS80 at a concentration (w/v) of 0.05%.

6. The pharmaceutical composition of claim 1, wherein the composition comprises histidine at a concentration of 20 mM.

7. The pharmaceutical composition of claim 1, wherein the composition comprises sucrose at a concentration (w/v) of 0.01% to 3%.

8. The pharmaceutical composition of claim 1, wherein the composition has a pH of 5.5.

9. The pharmaceutical composition of claim 1, comprising:
   the anti-Aβ antibody or the Aβ-binding fragment thereof at a concentration of 175 mg/ml;
   Arg.HCl at a concentration of 150 mM;
   methionine at a concentration of 10 mM;
   histidine at a concentration of 10 mM to 30 mM;
   thiol-containing antioxidant at a concentration of 0.02 mM to 4 mM; and
   PS80 at a concentration (w/v) of 0.03% to 0.08%;
   wherein the composition has a pH of 5.2 to 5.8.

10. The pharmaceutical composition of claim 1, comprising:
    the anti-Aβ antibody or the Aβ-binding fragment thereof at a concentration of 175 mg/ml;
    Arg.HCl at a concentration of 150 mM;
    methionine at a concentration of 10 mM;
    histidine at a concentration of 20 mM;
    thiol-containing antioxidant at a concentration of 0.4 mM; and
    PS80 at a concentration (w/v) of 0.05%,
    wherein the composition has a pH of 5.5.

11. The pharmaceutical composition of claim 1, wherein the VH comprises the amino acid sequence set forth in SEQ ID NO:7 and the VL comprises the amino acid sequence set forth in SEQ ID NO:8.

12. The pharmaceutical composition of claim 1, wherein the anti-Aβ antibody comprises an immunoglobulin heavy chain and an immunoglobulin light chain, wherein the heavy chain comprises the amino acid sequence set forth in SEQ ID NO:9 and the light chain comprises the amino acid sequence set forth in SEQ ID NO:10.

13. The pharmaceutical composition of claim 1, wherein the composition comprises methionine at a concentration of 10 mM.

14. The pharmaceutical composition of claim 1, comprising:
    the anti-Aβ antibody or the Aβ-binding fragment thereof at a concentration of 100 mg/ml to 200 mg/ml;
    Arg.HCl at a concentration of 150 mM;
    methionine at a concentration of 10 mM;
    histidine at a concentration of 20 mM;
    thiol-containing antioxidant at a concentration of 0.02 mM to 4 mM; and
    PS80 at a concentration (w/v) of 0.03% to 0.08%;
    wherein the composition has a pH of 5.2 to 5.8.

15. The pharmaceutical composition of claim 1, the anti-Aβ antibody is a human IgG1 antibody.

16. The pharmaceutical composition of claim 14, wherein the VH comprises the amino acid sequence set forth in SEQ ID NO:7 and the VL comprises the amino acid sequence set forth in SEQ ID NO:8.

17. The pharmaceutical composition of claim 16, the anti-Aβ antibody is a human IgG1 antibody.

18. The pharmaceutical composition of claim 17, wherein the anti-Aβ antibody comprises an immunoglobulin heavy chain and an immunoglobulin light chain, wherein the heavy chain comprises the amino acid sequence set forth in SEQ ID NO:9 and the light chain comprises the amino acid sequence set forth in SEQ ID NO:10.

* * * * *